United States Patent
Murakami

(10) Patent No.: US 12,231,165 B2
(45) Date of Patent: Feb. 18, 2025

(54) TRANSMISSION DEVICE, RECEPTION DEVICE, COMMUNICATION SYSTEM, TRANSMISSION METHOD, RECEPTION METHOD, AND COMMUNICATION METHOD

(71) Applicant: Panasonic Intellectual Property Corporation of America, Torrance, CA (US)

(72) Inventor: Yutaka Murakami, Kanagawa (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 0 days.

(21) Appl. No.: 18/093,005

(22) Filed: Jan. 4, 2023

(65) Prior Publication Data

US 2023/0142456 A1 May 11, 2023

Related U.S. Application Data

(60) Continuation of application No. 17/362,017, filed on Jun. 29, 2021, now Pat. No. 11,575,435, which is a
(Continued)

(51) Int. Cl.
*H04B 10/116* (2013.01)
*A61F 5/01* (2006.01)
(Continued)

(52) U.S. Cl.
CPC ............ *H04B 10/116* (2013.01); *A61F 5/013* (2013.01); *H04W 48/08* (2013.01); *H04W 48/16* (2013.01);
(Continued)

(58) Field of Classification Search
CPC .............. H04B 10/116; H04B 10/1141; H04B 10/1149; H04W 48/08; H04W 48/16;
(Continued)

(56) References Cited

U.S. PATENT DOCUMENTS

| 6,424,639 B1 * | 7/2002 | Lioy ................. H04W 36/0011 370/469 |
| 7,447,176 B2 | 11/2008 | Ruan |

(Continued)

FOREIGN PATENT DOCUMENTS

| CA | 2628940 | 10/2008 | |
| CA | 2892923 A1 * | 5/2014 | ........... G01C 21/206 |

(Continued)

OTHER PUBLICATIONS

International Search Report (ISR) issued on Nov. 21, 2017 in International (PCT) Application No. PCT/JP2017/036597.
(Continued)

*Primary Examiner* — Abbas H Alagheband
(74) *Attorney, Agent, or Firm* — Wenderoth, Lind & Ponack, L.L.P.

(57) ABSTRACT

Provided is a device, which is a transmission device that can improve performance, that includes: a light source; and a transmitter that generates a modulated signal based on an input signal and transmits the modulated signal from the light source as visible light by changing a luminance of the light source in accordance with the modulated signal. The transmitter includes, in the modulated signal, a plurality of items of information related to service set identifiers (SSIDs) of a plurality of mutually different access points in a wireless local area network (LAN), and transmits the modulated signal from the light source.

2 Claims, 36 Drawing Sheets

Related U.S. Application Data continuation of application No. 16/916,672, filed on Jun. 30, 2020, now Pat. No. 11,095,368, which is a division of application No. 16/380,458, filed on Apr. 10, 2019, now Pat. No. 10,742,319, which is a continuation of application No. PCT/JP2017/036597, filed on Oct. 10, 2017.

(60) Provisional application No. 63/407,003, filed on Sep. 15, 2022, provisional application No. 62/411,035, filed on Oct. 21, 2016.

(51) Int. Cl.
   *H04B 10/114* (2013.01)
   *H04L 9/40* (2022.01)
   *H04W 48/08* (2009.01)
   *H04W 48/16* (2009.01)
   *H04W 76/11* (2018.01)
   *H04W 84/12* (2009.01)

(52) U.S. Cl.
   CPC ............ *H04W 76/11* (2018.02); *H04W 84/12* (2013.01); *A61F 2230/0063* (2013.01); *H04B 10/1141* (2013.01); *H04B 10/1149* (2013.01); *H04L 63/0823* (2013.01); *H04L 63/083* (2013.01)

(58) Field of Classification Search
   CPC ... H04W 76/11; H04W 84/12; H04L 63/0823; H04L 63/083
   USPC .......................................................... 398/118
   See application file for complete search history.

(56) References Cited

U.S. PATENT DOCUMENTS

| | | | |
|---|---|---|---|
| 9,008,519 B2 * | 4/2015 | Park | H04B 10/1149 398/118 |
| 9,037,001 B2 * | 5/2015 | Jovicic | H04B 10/116 398/118 |
| 9,524,412 B2 | 12/2016 | Kim | |
| 9,800,334 B2 | 10/2017 | Dong | |
| 9,871,587 B2 * | 1/2018 | Aoyama | H04B 10/116 |
| 10,009,099 B2 | 6/2018 | Walma | |
| 10,064,153 B2 | 8/2018 | Yumura | |
| 10,200,933 B2 | 2/2019 | Jeong | |
| 10,206,069 B2 | 2/2019 | Lee | |
| 10,302,734 B2 * | 5/2019 | Ganick | H04N 25/76 |
| 2003/0118015 A1 | 6/2003 | Gunnarsson | |
| 2008/0199184 A1 * | 8/2008 | Takeshita | H04L 63/08 398/115 |
| 2009/0088182 A1 | 4/2009 | Piersol et al. | |
| 2009/0232019 A1 | 9/2009 | Gupta | |
| 2013/0126713 A1 | 5/2013 | Haas | |
| 2014/0036841 A1 | 2/2014 | Gray | |
| 2014/0119734 A1 * | 5/2014 | Lundgren | H04B 10/1149 398/115 |
| 2014/0126911 A1 * | 5/2014 | Jovicic | H04B 10/11 398/116 |
| 2014/0254477 A1 | 9/2014 | Fricke | |
| 2015/0188632 A1 * | 7/2015 | Aoyama | H04B 10/116 398/118 |
| 2015/0200762 A1 | 7/2015 | Kim et al. | |
| 2015/0223277 A1 | 8/2015 | Jovicic et al. | |
| 2015/0280818 A1 | 10/2015 | Walma | |
| 2015/0358825 A1 | 12/2015 | Dinan | |
| 2016/0029244 A1 | 1/2016 | Dinan | |
| 2016/0119761 A1 | 4/2016 | Ryan | |
| 2016/0191158 A1 * | 6/2016 | Aoyama | H04B 10/54 398/172 |
| 2016/0270147 A1 * | 9/2016 | Mathews | H04W 76/10 |
| 2016/0295546 A1 * | 10/2016 | Yumura | H04W 4/029 |
| 2016/0323035 A1 * | 11/2016 | Jovicic | H04B 10/0795 |
| 2017/0026208 A1 | 1/2017 | Milosiu | |
| 2017/0041072 A1 | 2/2017 | Rong | |
| 2017/0061900 A1 | 3/2017 | Ueki et al. | |
| 2017/0163513 A1 | 6/2017 | Kim | |
| 2017/0207851 A1 * | 7/2017 | Zeng | H04B 10/116 |
| 2017/0350962 A1 | 12/2017 | Jovicic et al. | |
| 2018/0220511 A1 * | 8/2018 | Clout | H05B 47/11 |

FOREIGN PATENT DOCUMENTS

| | | | |
|---|---|---|---|
| CN | 108663054 A * | 10/2018 | ............ G01C 21/26 |
| EP | 2 498 550 | 9/2012 | |
| EP | 858 268 A1 | 4/2015 | |
| JP | 2003-259444 A | 9/2003 | |
| JP | WO2003036829 A1 * | 2/2005 | ............ H04B 10/66 |
| JP | 2007-110274 | 4/2007 | |
| JP | 2007-110276 A | 4/2007 | |
| JP | 2008-199503 A | 8/2008 | |
| JP | 2009-89395 A | 4/2009 | |
| JP | 2013-128204 A | 6/2013 | |
| JP | 2014-090413 A | 5/2014 | |
| JP | 2014-116871 | 6/2014 | |
| JP | 2015-233276 | 12/2015 | |
| JP | 2016-504794 A | 2/2016 | |
| JP | 2016-165116 | 9/2016 | |
| KR | 101653902 B1 * | 9/2016 | ............ G08B 21/24 |
| KR | 101657072 B1 * | 9/2016 | ............ G06Q 50/26 |
| TW | I736702 B * | 8/2021 | |
| WO | 2015/161410 | 10/2015 | |
| WO | 2016/047030 | 3/2016 | |
| WO | 2016/049837 | 4/2016 | |
| WO | 2018/057184 | 3/2018 | |
| WO | WO-2022254789 A1 * | 12/2022 | ............ H04N 25/70 |

OTHER PUBLICATIONS

Santosh Pandey, et al., "NGP Use Case Template", IEEE 802.11-16/0137r4, Mar. 12, 2016.
Mitsuaki Oshima, et al., "Image Sensor-based Visible Light Communication Technology", Panasonic Technical Journal, vol. 61, No. 2, Nov. 2015, pp. 40-45 (with English abstract).
Extended European Search Report issued Oct. 4, 2019 in corresponding European Patent Application No. 17860036.7.
Office Action dated May 31, 2024 along with search report for corresponding Chinese patent application No. 202211006223.X, 9 pages.
Extended European Search Report dated Sep. 10, 2024 in corresponding European patent application No. 24175358.1, 11 pages.

* cited by examiner

TRANSMISSION DEVICE, RECEPTION DEVICE, COMMUNICATION SYSTEM, TRANSMISSION METHOD, RECEPTION METHOD, AND COMMUNICATION METHOD

CROSS REFERENCE TO RELATED APPLICATIONS

This application is a continuation of U.S. application Ser. No. 17/362,017, filed Jun. 29, 2021, which is a continuation of U.S. application Ser. No. 16/916,672, filed Jun. 30, 2020, now U.S. Pat. No. 11,095,368, which is a divisional of U.S. application Ser. No. 16/380,458, filed Apr. 10, 2019, now U.S. Pat. No. 10,742,319, which is a U.S. continuation application of PCT International Patent Application Number PCT/JP2017/036597 filed on Oct. 10, 2017, claiming the benefit of priority of U.S. Provisional Patent Application No. 62/407,003 filed on Oct. 12, 2016 and U.S. Provisional Patent Application No. 62/411,035 filed on Oct. 21, 2016. The entire disclosures of the above-identified applications, including the specifications, drawings and claims are incorporated herein by reference in their entirety.

FIELD

The present disclosure relates to a transmission device, a reception device, a communication system, a transmission method, a reception method, and a communication method.

BACKGROUND

Devices can use global positioning system (GPS) as a method for obtaining location information. In such cases, devices receive a modulated signal transmitted from a satellite, and estimate location by positioning calculation. However, it is difficult for the device to estimate location information when the device is indoors, where reception of the radio waves transmitted by the GPS satellite is difficult.

For example, one method for overcoming such a problem is disclosed in non-patent literature (NPTL) 1. As disclosed in NPTL 1, there is a method by which the device uses radio waves transmitted from an access point in a wireless local area network (LAN) to estimate location.

CITATION LIST

Non-Patent Literature

[Non-Patent Literature 1]
Santosh Pandey, "NGP Use Case Template" IEEE802.11-16/0137 r4, 2016 Mar. 12

SUMMARY

Technical Problem

However, the performance of the transmission device and the reception device can be improved upon.

Solution to Problem

A transmission device according to one aspect of the present disclosure includes: a light source; and a transmitter that generates a modulated signal based on an input signal and transmits the modulated signal from the light source as visible light by changing a luminance of the light source in accordance with the modulated signal. The modulated signal includes a plurality of items of information related to service set identifiers (SSIDs) of a plurality of mutually different access points in a wireless local area network (LAN).

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

According to the present disclosure, it is possible to improve upon the performance of a communication device and a reception device.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

DESCRIPTION OF EMBODIMENTS

Underlying Knowledge Forming Basis of the Present Disclosure

Devices can use global positioning system (GPS) as a method for obtaining location information. In such cases, devices receive a modulated signal transmitted from a satellite, and estimate location by positioning calculation. However, it is difficult for the device to estimate location information when the device is indoors, where reception of the radio waves transmitted by the GPS satellite is difficult.

For example, one method for overcoming such a problem is disclosed in NPTL 1 described above. As disclosed in NPTL 1, there is a method by which the device uses radio waves transmitted from an access point in a wireless local area network (LAN) to estimate location. However, since it is not easy to know the service set identifier (SSID) of an access point that can be securely accessed, when the device attempts to obtain location information, there is a possibility that the device will connect to an insecure SSID access point, leading to the possibility of a compromise of information.

In view of this, in the present disclosure, a (optical) modulated signal including information related to a location is transmitted, for example, from, for example, a light emitting diode (LED) lamp, light source, or light that is provided in a room and emits visible light. For example, a terminal (device) receives a (optical) modulated signal via, for example, an image sensor such as a complementary metal oxide semiconductor (CMOS) or organic photoconductive film (OPF) CMOS (i.e., organic CMOS) image sensor, performs demodulation and such, and obtains at least the information related to a location. With this, the terminal can achieve the advantageous effect of being able to securely obtain information related to a location.

Alternatively, in the present disclosure, for example, a (optical) modulated signal including information related to an SSID is transmitted, for example, from, for example, a light emitting diode (LED) lamp, light source, or light that is provided in a room and emits visible light. A terminal (device) receives a (optical) modulated signal via, for example, an image sensor such as a complementary metal oxide semiconductor (CMOS) or organic photoconductive film (OPF) CMOS (i.e., organic CMOS) image sensor, performs demodulation and such, and obtains at least the information related to the SSID. With this, the terminal can achieve the advantageous effect of being able to securely connect to an access point.

Embodiment 1

Figure 1:
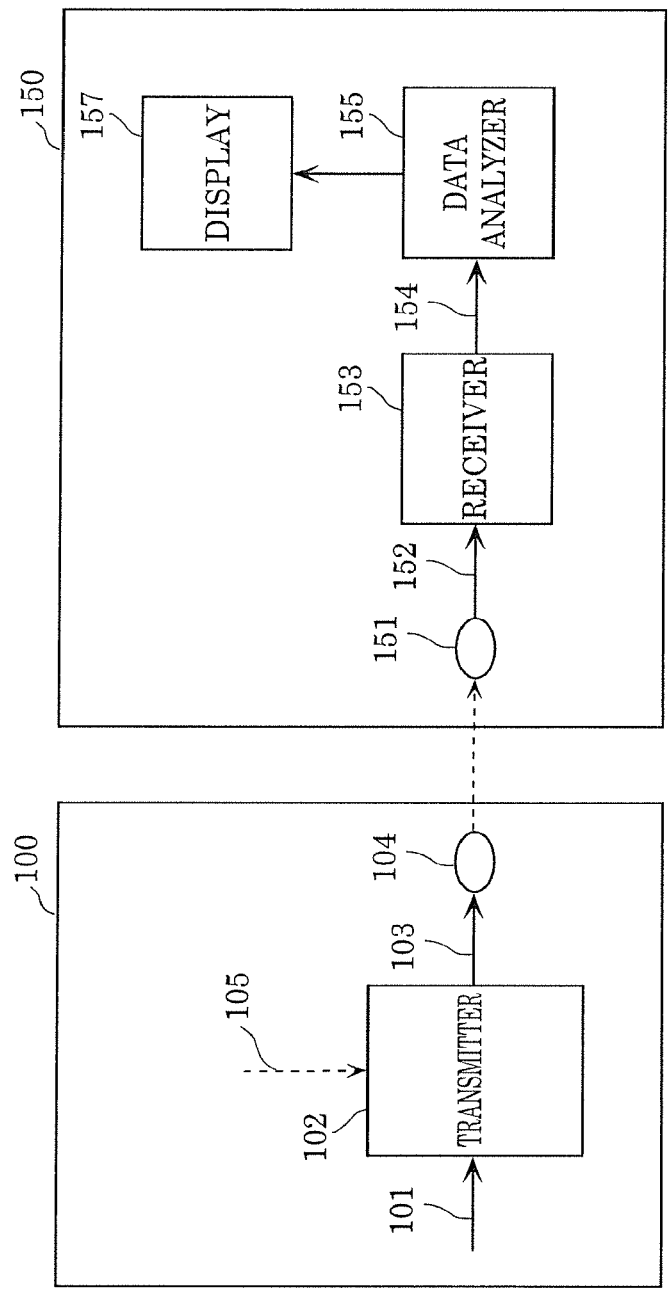
FIG. 1 illustrates one example of a configuration of a device and a terminal according to Embodiment 1.

FIG. 1 illustrates one example of configurations of device 100 including, for example, a light emitting diode (LED) light source, lamp, light source, and/or light that emits visible light, and terminal 150. Device 100 includes, for example, a light emitting diode (LED) lamp, light source, and/or light that emits visible light. Note that this device is referred to as a "first device".

Transmitter 102 receives an input of information related to a location or information 101 related to a position. Moreover, transmitter 102 may receive an input of information 105 related to a time. Moreover, transmitter 102 may receive an input of both (i) the information related to a location or information 101 related to a position and (ii) information 105 related to a time.

Transmitter 102 receives an input of information related to a location or information 101 related to a position and/or information 105 related to a time, and based on the one or more input signals, generates a (optical) modulated signal, and outputs modulated signal 103. For example, modulated signal 103 is transmitted from light source 104.

Next, examples of the information related to a location or information 101 related to a position will be given.

Example 1

Information related to a location or information 101 related to a position may be information indicating the latitude and/or longitude of a location or position. For example, the information related to a location or information 101 related to a position may be information indicating "45 degrees north latitude, 135 degrees east longitude".

Example 2

Information related to a location or information 101 related to a position may be information indicating an address. For example, the information related to a location or information 101 related to a position may be information indicating "1-1-1 XYZ-machi, Chiyoda-ku, Tokyo-to".

Example 3

Information related to a location or information 101 related to a position may be information indicating a building or facility, for example. For example, the information related to a location or information 101 related to a position may be information indicating "Tokyo Tower".

Example 4

Information related to a location or information 101 related to a position may be information indicating a fixed location or position of something at a building or facility, for example.

For example, assume there are five parking spaces for automobiles in a parking lot. Assume the first through fifth parking spaces are named A-1 through A-5, respectively. In this example, the information related to a location or information 101 related to a position may be information indicating, for example, "A-3".

This example is not limited to only parking spaces in a parking lot.

Information related to a location or information 101 related to a position may be for example, information related to a section, a seat, a store, a facility, etc., at, for example, a concert facility, a stadium such as a baseball, soccer, or tennis stadium, an airplane, an airport lounge, a railway, a station, etc.

Note that methods for configuring the information related to a location or information 101 related to a position are not limited to the above examples.

Terminal 150 receives the modulated signal transmitted by first device 100.

Light receiver 151 is, for example, a CMOS or organic CMOS image sensor. Light receiver 151 receives light including the modulated signal output from the first device, and outputs reception signal 152. Receiver 153 receives an input of reception signal 152, performs processing such as demodulation and error correction decoding on the modulated signal included in the reception signal, and outputs reception data 154.

Note that reception signal 152 output from light receiver 151 may be a signal including information on an image or moving picture obtained by the image sensor, and may be an output signal from an element that performs photo-electric conversion (an element that converts light into an electric signal). In the following description, when a reception-side device is described as receiving a modulated signal without giving any further details on the processes performed by light receiver 151, this means that the reception-side device obtains a signal of an image or moving picture and a modulated signal for transmitting information by photo-electric conversion (converting light into an electric signal) of light including the modulated signal by light receiver 151. However, the method described above used to receive the modulated signal by the reception-side device is merely one non-limiting example.

Data analyzer 155 receives an input of reception data 154, estimates, for example, the location or position of terminal 150 from reception data 154, and outputs information 156 including at least information on the location or position of terminal 150.

Display 157 receives an input of information 156, and displays information related to the location or position of terminal 150 based on the location or position of terminal 150 included in information 156.

Figure 2:
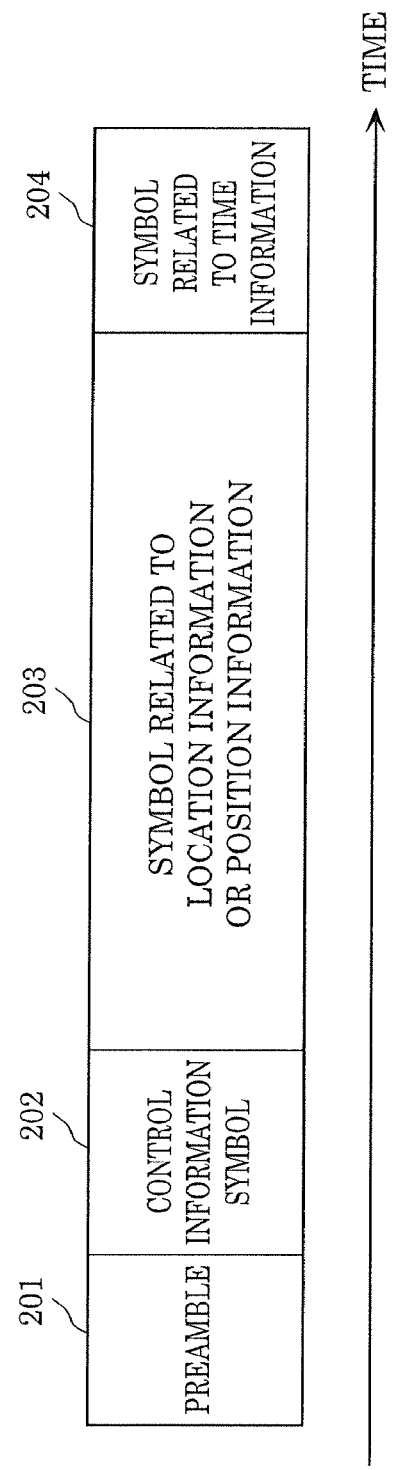
FIG. 2 illustrates one example of a frame configuration transmitted in a modulated signal transmitted by a first device according to Embodiment 1.

FIG. 2 illustrates one example of a configuration of a frame transmitted in a modulated signal transmitted by first device 100. In FIG. 2, time is represented on the horizontal axis. For example, the first device transmits preamble 201 and then transmits control information symbol 202, symbol 203 related to location information or position information, and symbol 204 related to time information.

Here, preamble 201 is a symbol for terminal 150, which receives the modulated signal transmitted by first device 100, to perform, for example, signal detection, temporal synchronization, and/or frame synchronization.

Control information symbol 202 is, for example, a symbol including data on, for example, the configuration method of the modulated signal, the error correction encoding scheme used, and/or the frame configuration method.

Symbol 203 related to location information or position information is a symbol including information related to a location or information related to a position illustrated in FIG. 1.

The frame may include symbols other than symbols 201, 202, and 203. For example, as illustrated in FIG. 2, the frame may include symbol 204 related to time information. Symbol 204 related to time information includes, for example, information indicating a time of transmission of the modulated signal by the first device. Note that the frame configuration of the modulated signal transmitted by the first device is not limited to the frame configuration illustrated in FIG. 2. Moreover, the symbols included in the modulated signal are not limited to the configuration illustrated in FIG. 2 (the modulated signal may include symbols including other data and/or information).

Next, the advantageous effects achieved when the first device transmits a modulated signal and the terminal receives the modulated signal, as described with reference to FIG. 1 and FIG. 2, will be described.

Since the first device transmits the modulated signal via visible light, a terminal capable of receiving the modulated signal is not in a location significantly far from the location of the first device. Accordingly, by the terminal obtaining the location or position information transmitted by the first device, the terminal can achieve an advantageous effect whereby it is possible to easily (i.e., without having to perform complicated signal processing) obtain accurate position information. Moreover, when the first device is disposed in a place where reception of satellite radio waves from a GPS satellite is difficult, it is possible to achieve an advantageous effect whereby it is possible for the terminal to securely obtain accurate position information even in locations in which reception of radio waves from a GPS satellite is difficult, by the terminal receiving the modulated signal transmitted by the first device.

Embodiment 2

In this embodiment, a configuration in which a plurality of the first devices described in Embodiment 1 are provided will be described.

Figure 3:
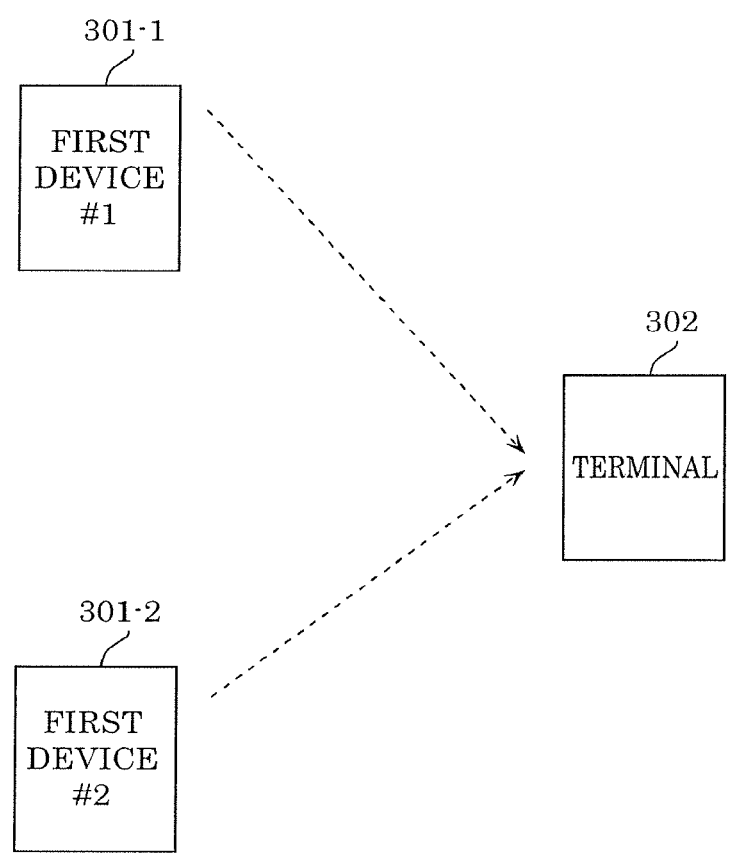
FIG. 3 illustrates one example including a plurality of devices according to Embodiment 2.

In this embodiment, for example, as illustrated in FIG. 3, first device #1 301-1 having the same configuration as first device 100 illustrated in FIG. 1 transmits a modulated signal, and terminal 302 receives the modulated signal. Terminal 302 receives the modulated signal transmitted by first device #1 301-1, and obtains, for example, information related to first location or position #1 and information related to first time #1.

Similarly, first device #2 301-2 having the same configuration as first device 100 illustrated in FIG. 1 transmits a modulated signal, and terminal 302 receives the modulated signal. Terminal 302 receives the modulated signal transmitted by first device #2 301-2, and obtains, for example, information related to first location or position #2 and information related to first time #2.

With this, terminal 302 can know the distance between first device #1 301-1 and first device #2 301-2 illustrated in FIG. 3 from the information related to first location or position #1 and the information related to first location or position #2. Moreover, terminal 302 can know the distance between terminal 302 and first device #1 301-1 based on the information related to first time #1, and, for example, the time at which the terminal receives the modulated signal transmitted by first device #1 301-1. Similarly, terminal 302 can know the distance between terminal 302 and first device #2 301-2 based on the information related to first time #2, and, for example, the time at which the terminal receives the modulated signal transmitted by first device #2 301-2.

Moreover, terminal 302 knows the position of first device #1 from the information related to the first location or position #1. Moreover, terminal 302 knows the position of first device #2 from the information related to the first location or position #2. Terminal 302 knows the geometry of the triangle formed by first device #1 301-1, first device #2 301-2, and terminal 302 from the distance between first device #1 301-1 and first device #2 301-2, the distance between first device #1 301-1 and the terminal, and the distance between first device #2 301-2 and the terminal.

Accordingly, terminal 302 can accurately calculate and obtain the position of terminal 302 from the position of the first device #1, the position of the first device #2, and the geometry of the triangle formed by first device #1 301-1, first device #2 301-2, and terminal 302.

However, the geodetic measurement method used by terminal 302 to obtain the location or position information is not limited to the method described above; any geodetic measurement method may be used. Examines of geodetic measurement methods include triangulation, traverse calculation, leveling, etc.

As described above, the terminal can obtain the above-described information from a plurality of devices including light sources that transmit location information, and as a result, it is possible to achieve an advantageous effect whereby the terminal can accurately estimate position. Moreover, as described in Embodiment 1, when the device including a light source that transmits location information is disposed in a place where reception of satellite radio waves from a GPS satellite is difficult, it is possible to achieve an advantageous effect whereby it is possible for the terminal to securely obtain accurate position information even in locations in which reception of radio waves from a GPS satellite is difficult, by the terminal receiving the modulated signal transmitted by the device.

Note that in the above example, the terminal receives modulated signals transmitted by two devices, but an embodiment in which the terminal receives modulated signals transmitted by more than two devices can be implemented in the same manner. Note that the more devices there are, the more accurately the terminal can calculate the position information, so from this viewpoint, more devices are more beneficial.

Embodiment 3

Figure 4:
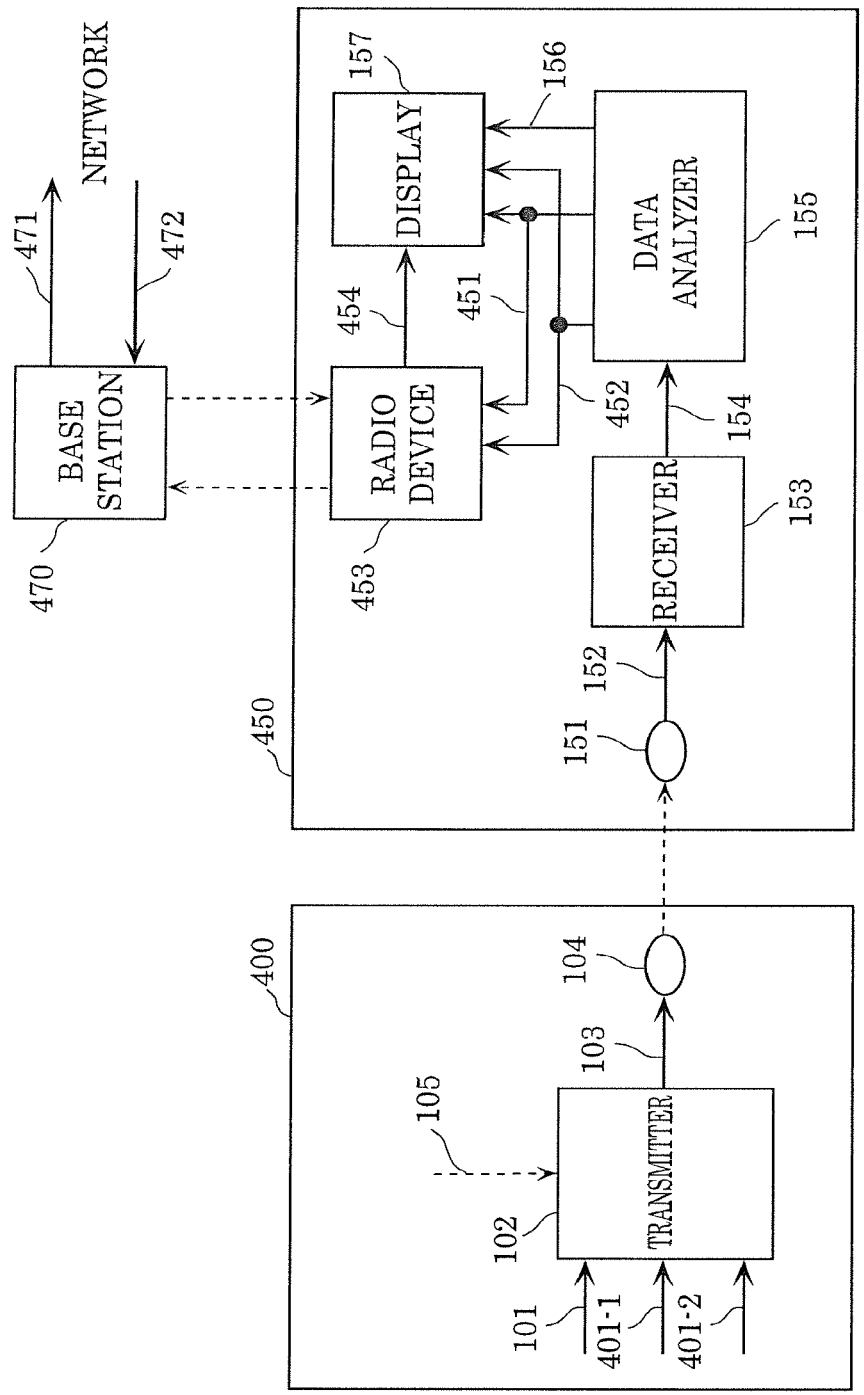
FIG. 4 illustrates one example of a configuration of a device and a terminal according to Embodiment 3.

FIG. 4 illustrates one example of configurations of; a device including, for example, an LED light source, lamp, light source, and/or light that emits visible light; a terminal; and, for example, a base station that communicates with the terminal. Device 400 in FIG. 4 includes, for example, an LED lamp, light source, and/or light that emits visible light. Note that the device is referred to as a "first device". In first device 400 in FIG. 4, elements that operate the same as in first device 100 in FIG. 1 share like reference marks.

Terminal 450 in FIG. 4 indicates the configuration of a terminal, and elements that are the same as in FIG. 1 share like reference marks.

In first device 400 in FIG. 4, transmitter 102 receives inputs of, for example, information related to a location or information 101 related to a position, information 401-1 related to a service set identifier (SSID), and information 401-2 related to an access destination. Moreover, transmitter 102 may receive an input of information 105 related to a time.

Transmitter 102 receives inputs of information related to a location or information 101 related to a position, information 401-1 related to an SSID, information 401-2 related to an access destination, and/or information 105 related to a time, and based on the one or more input signals, generates a (optical) modulated signal, and outputs modulated signal 103. For example, modulated signal 103 is transmitted from light source 104.

Note that since examples of the information related to a location or information 101 related to a position are the same as described in Embodiment 1, repeated description will be omitted.

Next, information 401-1 related to an SSID and information 401-2 related to an access destination will be described.

First, information 401-1 related to an SSID will be described.

Information 401-1 related to an SSID is information indicating the SSID of the base station (or access point (AP)) 470 illustrated in FIG. 4. When processing is performed for determining whether or not the SSID notified via the optical signal is the SSID of a secure base station, first device 400 can provide access to base station 470, which is a secure access destination for terminal 450. With this, terminal 450 in FIG. 4 can achieve the advantageous effect of being able to securely obtain information from base station (or AP) 470. On the other hand, first device 400 can restrict the terminals that access base station 470 to terminals in a space in which it is possible to receive optical signals transmitted (emitted) by first device 400.

Note that when terminal 450 receives an optical signal transmitted via a predetermined scheme, it may be determined that the notified SSID is the SSID of a secure base station, and, alternatively, processing for determining whether the SSID is secure or not may be performed. For example, first device 400 may transmit a predetermined identifier in an optical signal, and the terminal may determine whether the notified SSID is the SSID of a secure base station or not based on the received identifier. Alternatively, the processing for determining whether the base station is secure or not may be omitted by terminal 450, and instead, the user may select a first device 400 that is highly secure utilizing the characteristics of the visible light, and the SSID of the highly secure base station may be obtained by terminal 450 receiving the optical signal from first device 400.

Note that although FIG. 4 only illustrates base station (or AP) 470, for example, when there is a base station (or AP) other than base station (or AP) 470, terminal 450 in FIG. 4 accesses base station (or AP) 470 to obtain information.

Information 401-2 related to an access destination is information related to an access destination for terminal 450 in FIG. 4 to access base station (or AP) 470 and then obtain information (note that a specific example of operations will be given later).

Terminal 450 in FIG. 4 receives the modulated signal transmitted by first device 400. Note that in terminal 450 in FIG. 4, operations that are the same as in terminal 150 in FIG. 1 share like reference marks.

Light receiver 151 included in terminal 450, examples of which include an image sensor such as a CMOS or organic CMOS image sensor, receives the modulated signal transmitted by first device 400. Receiver 153 receives an input of reception signal 152 received by light receiver 151, performs processing such as demodulation and error correction decoding on the reception signal, and outputs reception data 154.

Data analyzer 155 receives an input of reception data 154, estimates, for example, the location or position of the terminal from reception data 154, and outputs information 156 including at least information on the location or position of the terminal, information 451 related to an SSID, and information 452 related to an access destination.

Display 157 receives inputs of information 156 including information on the location or position of the terminal, information 451 related to an SSID, and information 452 related to an access destination, and, for example, displays the location or position of the terminal, the SSID of a communication partner that radio device 453 included in terminal 450 accesses, and the access destination (this display is referred to as a "first display").

For example, after the first display, radio device 453 included in terminal 450 in FIG. 4 receives inputs of information 451 related to an SSID and information 452 related to an access destination. Then, radio device 453 included in terminal 450 in FIG. 4 connects to the communication partner by using, for example, radio waves, based on information 451 related to an SSID. Note that in the example illustrated in FIG. 4, radio device 453 included in terminal 450 in FIG. 4 connects to base station 470.

Then, based on information 452 related to an access destination, radio device 453 included in terminal 450 in FIG. 4 generates a modulated signal from data including the information related to an access destination, and transmits the generated modulated signal to base station 470 over, for example, radio waves.

Base station (or AP) 470, which is the communication partner of the terminal in FIG. 4, receives the modulated signal transmitted by radio device 453 included in terminal 450 in FIG. 4. Then, base station (or AP) 470 performs processing such as demodulation and error correction decoding on the received modulated signal, outputs reception data 471 including information on the access destination transmitted by terminal 450 in FIG. 4, and based on the information on the access destination, base station (or AP) 470 accesses a desired access destination over a network and, for example, obtains desired information 472 from the access destination.

Then, base station 470 receives an input of the desired information 472, generates a modulated signal from the desired information 472, and transmits the modulated signal to terminal 450 in FIG. 4 over, for example, radio waves.

Radio device 453 in terminal 450 in FIG. 4 receives the modulated signal transmitted by base station 470, performs processing such as demodulation and error correction decoding, and obtains the desired information 472.

For example, assume the desired information 472 is information related to a section, a seat, a store, a facility, etc., on/at, for example, a map, a map or floor guide for a building, a map or floor guide for a facility, a map or floor guide for a parking lot, a concert facility, a stadium such as a baseball, soccer, or tennis stadium, an airplane, an airport lounge, a railway, a station, etc.

Display 157 receives inputs of the desired information 472, information 156 including, at least information on the location or position of the terminal, information 451 related to an SSID, and after the first display, displays a result of mapping the position of the terminal on the display of the map, floor guide, facility information, seat information, or store information, based on the desired information 472 and information 156 including at least information on the location or position of the terminal.

Figure 5:
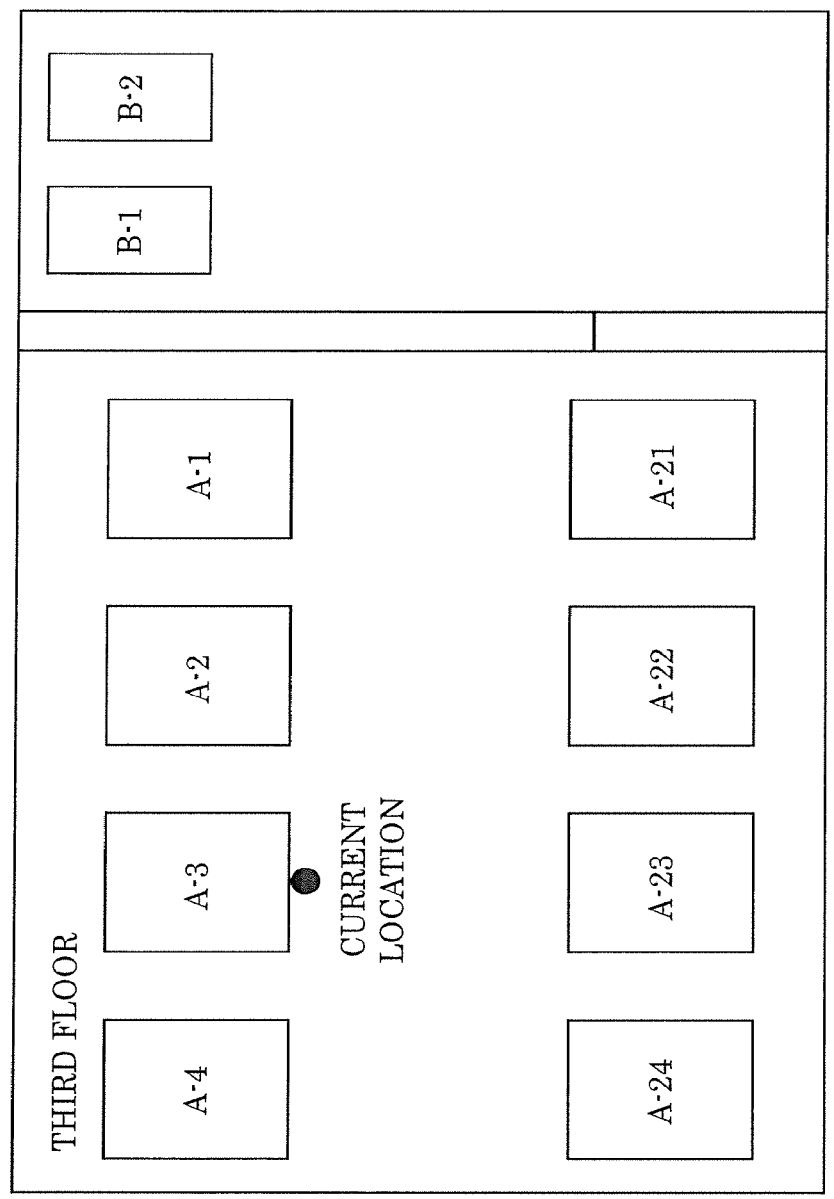
FIG. 5 illustrates one detailed example of a screen of a display according to Embodiment 3.

A specific example will be given. FIG. 5 illustrates one example of a display displayed by display 157. The display in FIG. 5 indicates that this is the third floor of a building. Each of A-1, A-2, A-3, A-4, A-21, A-22, A-23, and A-24 indicates a position of a parking space for an automobile. B-1 and B-2 indicate positions of elevators. The information on this map is the desired information 472. As illustrated in FIG. 5, the "current location" is mapped on the map. Here, the current location is information obtained from information 156 including at least information on the location or position of the terminal.

Figure 6:
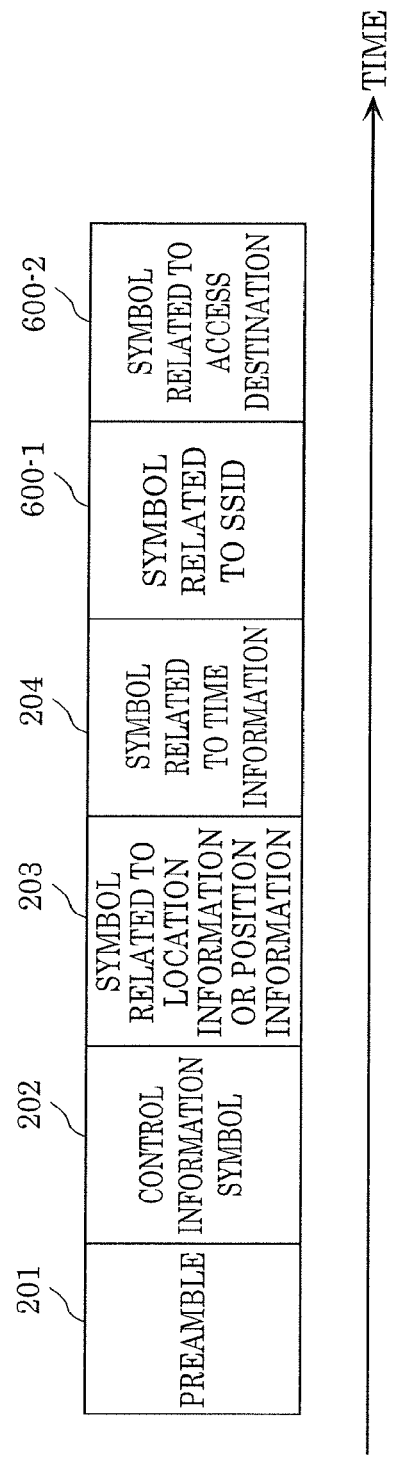
FIG. 6 illustrates one example of a frame configuration of a modulated signal transmitted by a first device according to Embodiment 3.

FIG. 6 illustrates one example of a configuration of a frame of a modulated signal transmitted by first device 400 in FIG. 4. In FIG. 6, time is represented on the horizontal axis, and symbols that transmit the same information as indicated in FIG. 2 share like reference marks. Accordingly, repeated description will be omitted First device 400 transmits symbol 600-1 related to an SSID and symbol 600-2 related to an access destination in addition to preamble 201, control information symbol 202, symbol 203 related to location information or position information, and symbol 204 related to time information.

Note that symbol 600-1 related to an SSID is a symbol for transmitting information 401-1 related to an SSID illustrated in FIG. 4, and symbol 600-2 related to an access destination is a symbol for transmitting information 401-2 related to an access destination in FIG. 4. Note that in the frame illustrated in FIG. 6, symbols other than the symbols shown in FIG. 6 may be included. Moreover, the frame configuration, including the order in which the symbols are transmitted, is not limited to the configuration illustrated in FIG. 6.

Figure 7:
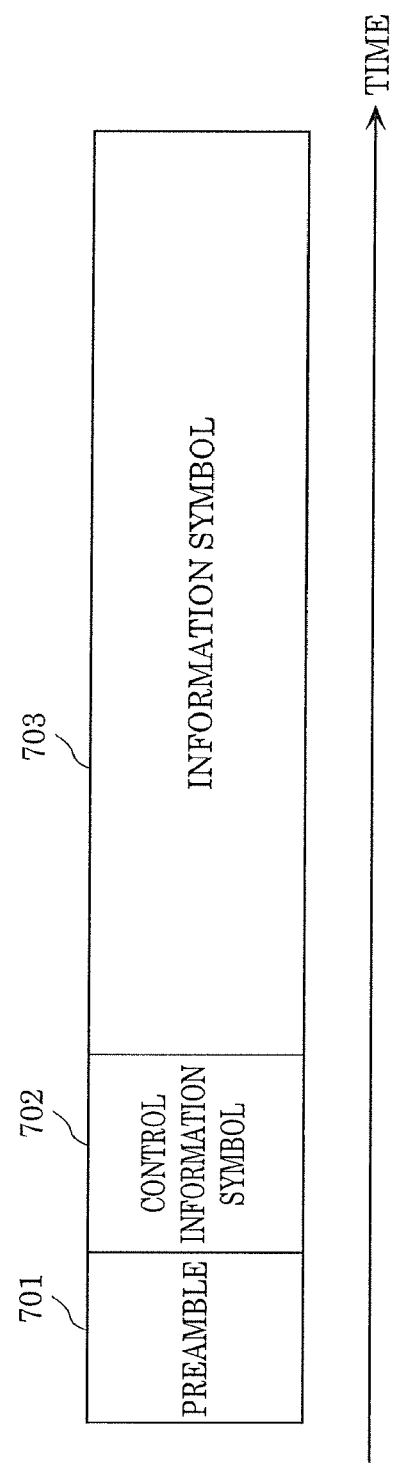
FIG. 7 illustrates one example of a frame configuration of a modulated signal transmitted by a base station according to Embodiments 3 through 6.

FIG. 7 illustrates one example of a frame configuration of a modulated signal transmitted by base station 470 illustrated in FIG. 4. Time is represented on the horizontal axis. As illustrated in FIG. 7, base station 470 transmits, for example, preamble 701, and then transmits control information symbol 702 and information symbol 703.

Here, preamble 701 is a symbol for the terminal, which receives the modulated signal transmitted by base station 470, to perform, for example, signal detection, temporal synchronization, frame synchronization, and/or frequency offset estimation.

Control information symbol 702 includes, for example, information related to the error correction encoding scheme method and/or demodulation scheme used in the generation of the modulated signal, and information related to frame configuration.

Information symbol 703 is a symbol for transmitting information. Note that in this embodiment, information symbol 703 is a symbol for transmitting the desired information 472 described above.

Note that base station 470 in FIG. 4 may transmit a frame including symbols other than the symbols illustrated in FIG. 7 (for example, a frame including a pilot symbol (reference symbol) midway through the information symbol). Moreover, the frame configuration, including the order in which the symbols are transmitted, is not limited to the configuration illustrated in FIG. 7. In FIG. 7, a plurality of symbols may be present along the frequency axis, that is to say, symbols may be present on a plurality of frequencies (a plurality of carriers).

Moreover, for example, a modulated signal that has the frame configuration illustrated in FIG. 6 and is transmitted by the first device being transmitted at a regular timing, e.g., repeatedly transmitted is conceivable. This makes it possible for a plurality of terminals to implement the operations described above.

Figure 8:
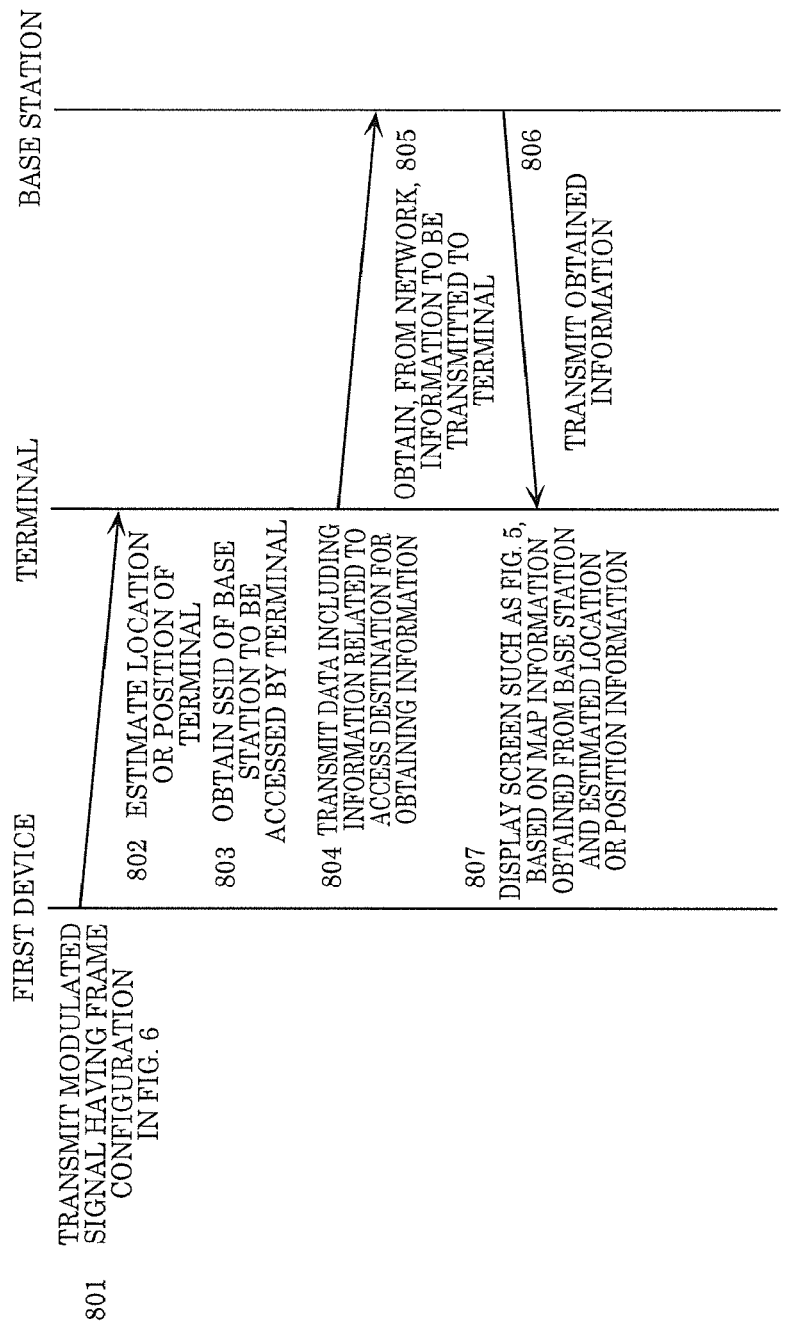
FIG. 8 is a flow chart of one example of processes performed by a device, terminal, and base station according to Embodiment 3.

FIG. 8 is a flow chart illustrating one example of processes implemented by first device 400, terminal 450, and base station (or AP) 470 illustrated in FIG. 4.

First, as 801 in FIG. 8 illustrates, first device 400 in FIG. 4 transmits a modulated signal having the frame configuration illustrated in FIG. 6.

Then, as 802 in FIG. 8 illustrates, the modulated signal transmitted by first device 400 in FIG. 4 is received, and terminal 450 in FIG. 4 performs terminal location or position estimation.

Likewise, as 803 in FIG. 8 illustrates, the modulated signal transmitted by first device 400 in FIG. 4 is received, and terminal 450 in FIG. 4 knows the SSID of the base station to be accessed by the terminal.

Then, as 804 in FIG. 8 illustrates, terminal 450 in FIG. 4 transmits, to base station (or AP) 470 in FIG. 4, a modulated signal including data including information related to an access destination for obtaining information, such as a map, using, for example, radio waves.

As 805 in FIG. 8 illustrates, base station (or AP) 470 receives the modulated signal transmitted by terminal 450, obtains the information on the access destination, accesses the desired access destination and obtains desired information, such as a map, over a network.

Then, as 806 in FIG. 8 illustrates, base station (or AP) 470 in FIG. 4 transmits a modulated signal including desired information, such as the obtained map, to terminal 450 using, for example, radio waves.

As 807 in FIG. 8 illustrates, terminal 450 receives the modulated signal transmitted by base station (or AP) 470 and obtains (for example) the map. Terminal 450 displays a screen such as the one illustrated in FIG. 5, based on information on (for example) the map and the location or position of the terminal already obtained.

Next, an example of operations performed when a plurality of first devices 400 and base station (or AP) 470 are disposed in the location illustrated in FIG. 5

Figure 9:
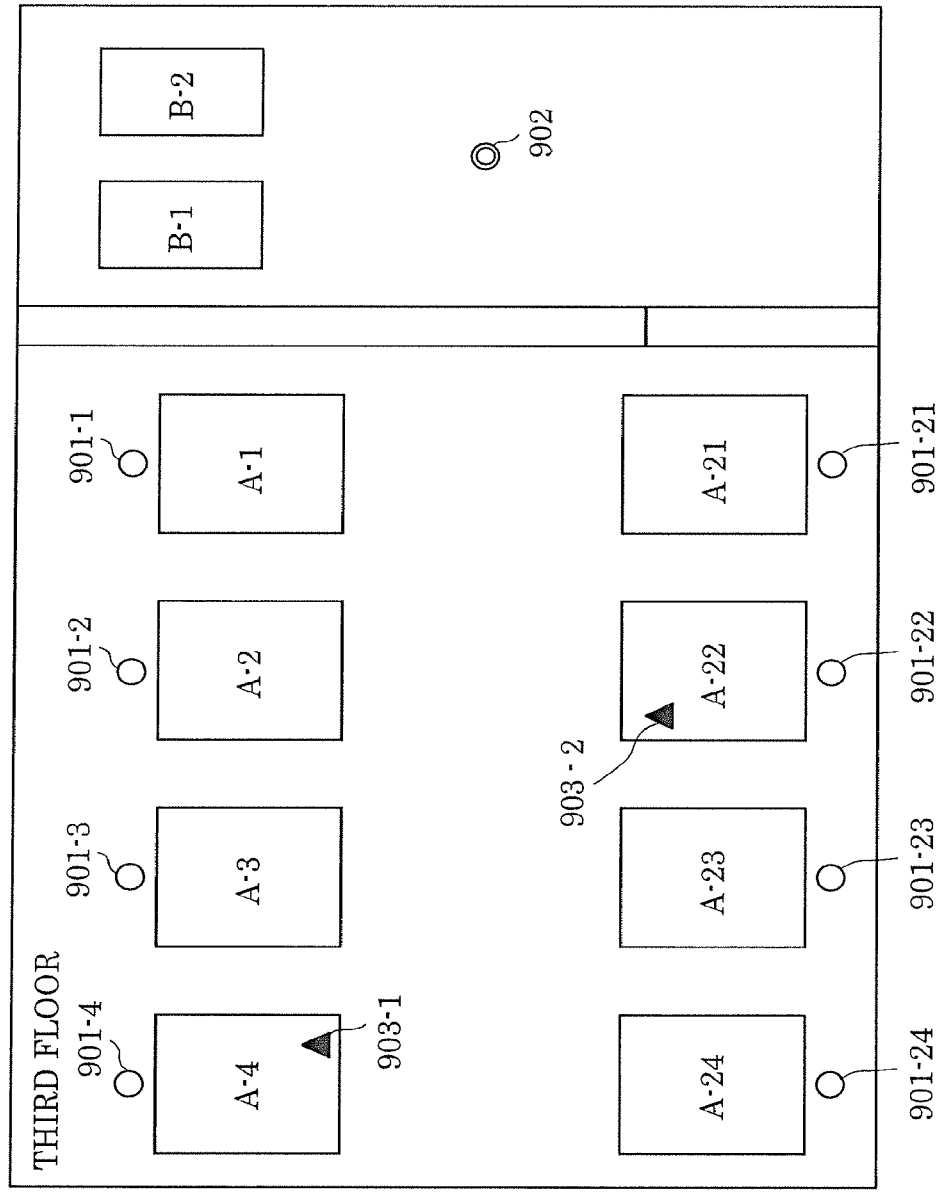
FIG. 9 illustrates one example of a map according to Embodiment 3.

Similar to FIG. 5, FIG. 9 illustrates a map of a given location.

As described with reference to FIG. 5, FIG. 9 is a map of the third floor of a building. Each of A-1, A-2, A-3, A-4, A-21, A-22, A-23, and A-24 indicates a position of a parking space for an automobile, and B-1 and B-2 indicate elevators.

The position of circle 901-1 in FIG. 9 indicates the location of a first device having the same configuration as device 100 illustrated in FIG. 4. A first device having the same configuration as device 100 in FIG. 4 at the position of 901-1 is referred to as "first device #1". The first device #1 holds and transmits, as information related to a location or information related to a position, information labeled "A-1".

The position of circle 901-2 in FIG. 9 indicates the location of a first device having the same configuration as device 100 illustrated in FIG. 4. A first device having the same configuration as device 100 in FIG. 4 and located at the position of 901-2 is referred to as "first device #2". The first device #2 holds and transmits, as information related to a location or information related to a position, information labeled "A-2".

The position of circle 901-3 in FIG. 9 indicates the location of a first device having the same configuration as device 100 illustrated in FIG. 4. A first device having the same configuration as device 100 in FIG. 4 and located at the position of 901-3 is referred to as "first device #3". The first device #3 holds and transmits, as information related to a location or information related to a position, information labeled "A-3".

The position of circle 901-4 in FIG. 9 indicates the location of a first device having the same configuration as device 100 illustrated in FIG. 4. A first device having the same configuration as device 100 in FIG. 4 and located at the position of 901-4 is referred to as "first device #4". The first device #4 holds and transmits, as information related to a location or information related to a position, information labeled "A-4".

The position of circle 901-21 in FIG. 9 indicates the location of a first device having the same configuration as device 100 illustrated in FIG. 4. A first device having the same configuration as device 100 in FIG. 4 and located at the position of 901-21 is referred to as "first device #21". The first device #21 holds and transmits, as information related to a location or information related to a position, information labeled "A-21".

The position of circle 901-22 in FIG. 9 indicates the location of a first device having the same configuration as device 100 illustrated in FIG. 4. A first device having the same configuration as device 100 in FIG. 4 and located at the position of 901-22 is referred to as "first device #22". The first device #22 holds and transmits, as information related to a location or information related to a position, information labeled "A-22".

The position of circle 901-23 in FIG. 9 indicates the location of a first device having the same configuration as device 100 illustrated in FIG. 4. A first device having the same configuration as device 100 in FIG. 4 and located at the position of 901-23 is referred to as "first device #23". The first device #23 holds and transmits, as information related to a location or information related to a position, information labeled "A-23".

The position of circle 901-24 in FIG. 9 indicates the location of a first device having the same configuration as first device 400 illustrated in FIG. 4. A first device having the same configuration as first device 400 in FIG. 4 and located at the position of 901-24 is referred to as "first device #24". The first device #24 holds and transmits, as information related to a location or information related to a position, information labeled "A-24".

The position of double circle 902 in FIG. 9 indicates the location of a base station (or AP) having the same configuration as base station 470 illustrated in FIG. 4. Here, the SSID of a base station (or AP) having the same configuration as base station 470 in FIG. 4 and located at the position of 902 is "abcdef".

When the terminals located around the positions illustrated in the map in FIG. 9 communicate wirelessly, the terminals may access a base station (or AP) having the same configuration as base station 470 in FIG. 4 and located at position 902 in FIG. 9. Accordingly, the first device #1 located at 901-1 in FIG. 9 transmits "abcdef" as information on an SSID (see 401-1 in FIG. 4).

Similarly, the first device #2 located at 901-2 in FIG. 9 transmits "abcdef" as information on an SSID (see 400-1 in FIG. 4).

The first device #3 located at 901-3 in FIG. 9 transmits "abcdef" as information on an SSID (see 401-1 in FIG. 4).

The first device #4 located at 901-4 in FIG. 9 transmits "abcdef" as information on an SSID (see 401-1 in FIG. 4).

The first device #21 located at 901-21 in FIG. 9 transmits "abcdef" as information on an SSID (see 401-1 in FIG. 4).

The first device #22 located at 901-22 in FIG. 9 transmits "abcdef" as information on an SSID (see 401-1 in FIG. 4).

The first device #23 located at 901-23 in FIG. 9 transmits "abcdef" as information on an SSID (see 401-1 in FIG. 4).

The first device #24 located at 901-24 in FIG. 9 transmits "abcdef" as information on an SSID (see 401-1 in FIG. 4).

Next, a specific example of operations will be given.

Assume a terminal having the same configuration as terminal 450 in FIG. 4 is positioned at 903-1 in FIG. 9. The terminal receives a modulated signal transmitted by the first device #4 positioned at 901-4 in FIG. 9, and receives position information referred to as "A-4". Moreover, the terminal obtains information on the SSID "abcdef", and as a result, the terminal accesses a base station (or AP) that has the same configuration as base station 470 in FIG. 4 and is positioned at 902 in FIG. 9, whereby the terminal obtains information, such as a map, from the base station (or AP) that has the same configuration as base station 470 in FIG. 4 and is positioned at 902 in FIG. 9. Then, the terminal displays map information and position information (see FIG. 5; however, FIG. 5 is only one, non-limiting example).

Assume a terminal having the same configuration as terminal 450 in FIG. 4 is positioned at 903-2 in FIG. 9. The terminal receives a modulated signal transmitted by the first device #22 positioned at 901-22 in FIG. 9, and receives position information referred to as "A-22". Moreover, the terminal obtains information on the SSID "abcdef", and as a result, the terminal accesses a base station (or AP) that has the same configuration as base station 470 in FIG. 4 and is positioned at 902 in FIG. 9, whereby the terminal obtains information, such as a map, from the base station (or AP) that has the same configuration as base station 470 in FIG. 4 and is positioned at 902 in FIG. 9. Then, the terminal displays map information and position information (see FIG. 5; however, FIG. 5 is only one, non-limiting example).

Note that the terminal stores a map (surrounding information) and position information, such as those illustrated in FIG. 5, in storage included in the terminal, and when the user of the terminal needs it, may make more use of the map (surrounding information) and position information by reading the stored information.

As described above, since the first device transmits the modulated signal via visible light, a terminal capable of receiving the modulated signal is limited to being located within a region capable of receiving the signal light from the position of the first device. Accordingly, by the terminal obtaining the location or position information transmitted by the first device, the terminal can achieve an advantageous effect whereby it is possible to easily (i.e., without having to perform complicated signal processing) obtain accurate position information. Moreover, when the first device is disposed in a place where reception of satellite radio waves from a GPS satellite is difficult, it is possible to achieve an advantageous effect whereby it is possible for the terminal to securely obtain accurate position information even in locations in which reception of radio waves from a GPS satellite is difficult, by the terminal receiving the modulated signal transmitted by the first device.

Furthermore, an advantageous effect is achieved in which, based on information on the SSID transmitted by the first device, the terminal connects to the base station (or AP) and obtains information to securely retrieve information. This is because, when information from a visible light modulated signal is obtained, since it is visible light, the user can easily recognize the first device transmitting the modulated signal, making it possible for the user to determine whether the source of information is secure or not.

For example, when an SSID is obtained from a modulated signal transmitted by a wireless LAN over radio waves, it is difficult for the user to determine which device transmitted the radio waves. Accordingly, from the viewpoint of ensuring information security, obtaining the SSID via visible light communication is more suitable.

Note that a plurality of input signals may further be in radio device 453 in terminal 450 in FIG. 4. For example, a control signal for controlling radio device 453 may be in radio device 453, and information transmitted by the base station may be in radio device 453 as input signals. Here, based on the control signal, operations for the start of communication by radio device 453 are conceivable as one example. As described above, the configuration of the first device is not limited to the configuration of first device 400 in FIG. 4, moreover the configuration of the terminal is not limited to the configuration of terminal 450 in FIG. 4, and moreover the device to which base station 470 connects is not limited to the configuration illustrated in FIG. 4.

Moreover, although only one base station (or AP) is exemplified in the configuration illustrated in FIG. 4, a plurality of (secure) base stations (or APs) accessible by the terminal may be included. Here, the symbol related to an SSID transmitted by first device 400 in FIG. 4 may include information indicating the SSIDs of the plurality of base stations (or APs). Terminal 450 in FIG. 4 may select a base station (or AP) to wirelessly connect to based on the information on the SSIDs of the base stations (or connect to the plurality of base stations (or APs)).

For example, assume there are three base stations (or APs). The three base stations are named base station #A, base station #B, and base station #C. The SSID of base station #A is "abcdef", the SSID of base station #B is "ghijk", and the SSID of base station #C is "pqrstu". In such cases, symbol 600-1 related to an SSID in the frame configuration illustrated in FIG. 6 of the modulated signal transmitted by the first device includes information related to the SSID "abcdef" of base station #A, the SSID "ghijk" of base station #B, and the SSID "pqrstu" of base station #C. Terminal 450 in FIG. 4 receives symbol 600-1 related to an SSID, and based on the SSID "abcdef" of base station #A, the SSID "ghijk" of base station #B, and the SSID "pqrstu" of base station #C, selects a base station (or AP) to wirelessly connect to.

Embodiment 4

Figure 10:
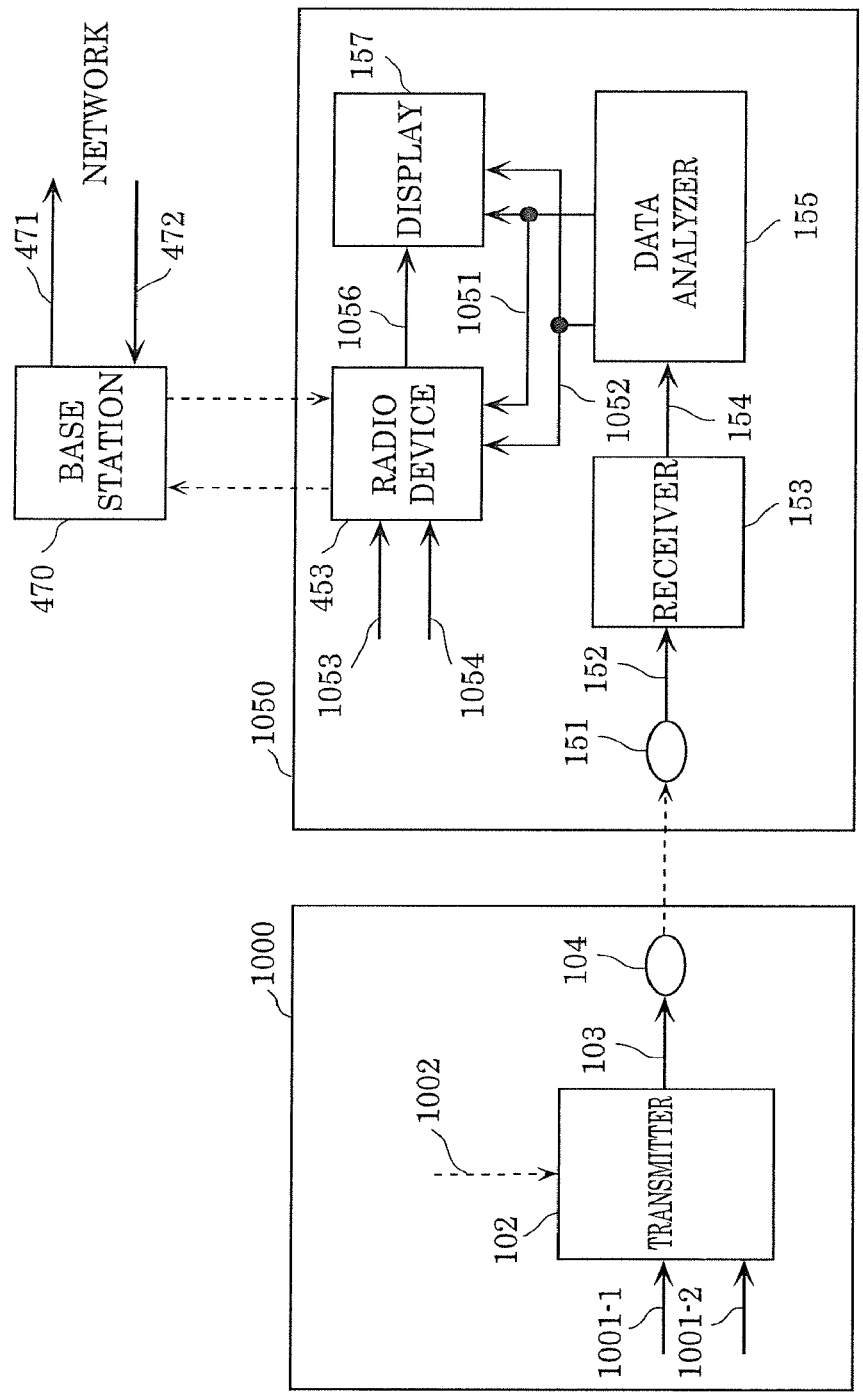
FIG. 10 illustrates one example of a configuration of a communication system according to Embodiment 4.

FIG. 10 illustrates one example of a configuration of a communication system according to this embodiment. The communication system illustrated in FIG. 10 includes, for example: device 1000 including an LED light source, lamp, light source, and/or light that emits visible light; terminal 1050; and, for example, base station 470 that communicates with terminal 1050. Device 1000 in FIG. 10 includes, for example, an LED lamp, light source, and/or light that emits visible light. Note that device 1000 is referred to as a "second device" in this embodiment. In second device 1000 in FIG. 10, elements that operate the same as in first device 100 in FIG. 1 share like reference marks.

In terminal 1050 in FIG. 10, components that operate the same as terminal 150 in FIG. 1 share like reference marks.

Note that communication between radio device 453 and base station 470 in FIG. 10 is performed using, for example, radio waves.

In second device 1000 in FIG. 10, transmitter 102 receives inputs of information 1001-1 related to an SSID, information 1001-2 related to an encryption key, and data 1002, and based on these input signals, generates a (optical) modulated signal, and outputs modulated signal 103. For example, modulated signal 103 is transmitted from light source 104.

Next, information 1001-1 related to an SSID and information 1001-2 related to an encryption key will be described.

First, information 1001-1 related to an SSID will be described.

Information 1001-1 related to an SSID is information indicating the SSID of base station (or AP) 470 in FIG. 10. Note that, in this example, base station (or AP) 470 transmits modulated signals over radio waves, and receives radio wave modulated signals. In other words, second device 1000 can provide access to base station 470, which is a secure access destination for the terminal. With this, terminal 1050 in FIG. 10 can achieve the advantageous effect of being able to securely obtain information from base station (or AP) 470. On the other hand, device 1000 can restrict the terminals that access base station 470 to terminals in a space in which it is possible to receive optical signals transmitted (emitted) by device 1000. Note that when terminal 1050 receives an optical signal transmitted via a predetermined scheme, it may be determined that the notified SSID is the SSID of a secure base station, and, alternatively, processing for determining whether the SSID is secure or not may be performed. For example, device 1000 may transmit a predetermined identifier in an optical signal, and the terminal may determine whether the notified SSID is the SSID of a secure base station or not based on the received identifier.

Note that although FIG. 10 only illustrates base station (or AP) 470, for example, when there is a base station (or AP) other than base station (or AP) 470, terminal 1050 in FIG. 10 accesses base station (or AP) 470 to obtain information.

Information 1001-2 related to an encryption key is information related to an encryption key required for terminal 1050 in FIG. 10 to establish communication with base station (or AP) 470 in FIG. 10. Encrypted communication is possible between terminal 1050 in FIG. 10 and base station (or AP) 470 as a result of terminal 1050 in FIG. 10 obtaining this information from second device 1000 in FIG. 10.

Terminal 1050 in FIG. 10 receives the modulated signal transmitted by second device 1000. Note that in terminal 1050 in FIG. 10, components that operate the same as terminal 150 in FIG. 1 and terminal 450 in FIG. 4 share like reference marks.

Light receiver 151 included in terminal 1050, examples of which include an image sensor such as a CMOS or organic CMOS image sensor, receives the modulated signal transmitted by second device 1000. Receiver 153 receives an input of reception signal 152 received by light receiver 151, performs processing such as demodulation and error correction decoding on the reception signal, and outputs reception data 154.

Data analyzer 155 receives an input of reception data 154, and outputs, based on the reception data, for example, information 1051 on the SSID of the base station (470) to be connected to, and information 1052 on the encryption key for communication with the base station (470) to be connected to. For example, in a wireless local area network (LAN), examples of encryption schemes include wired equivalent privacy (WEP), Wi-Fi™ protected access (WPA), and Wi-Fi protected access 2 (WPA2) (pre-shared key (PSK) mode, extended authentication protocol (EAP) mode). However, the encryption method is not limited to these examples.

Display 157 receives inputs of information 1051 on the SSID and information 1052 on the encryption key, and, for example, displays the SSID of the communication partner to be accessed by radio device 453 included in the terminal, and the encryption key (this display is referred to as a "first display" in this embodiment).

For example, after the first display, radio device 453 included in terminal 1050 in FIG. 10 receives inputs of information 1051 on the SSID and information 1052 on the encryption key, and establishes a connection with base station (or AP) 470 (for example, the connection uses radio waves). Here, when base station (or AP) 470 also communicates with radio device 453 in terminal 1050 in FIG. 10, base station (or AP) 470 transmits a modulated signal using, for example, radio waves.

Thereafter, radio device 453 included in terminal 1050 in FIG. 10 receives inputs of data 1053 and control signal 1054, demodulates data 1053 in accordance with control signal 1054, and transmits a modulated signal as radio waves.

Then, for example, base station (or AP) 470 transmits data to the network (471) and receives data (472) from the network. Thereafter, for example, base station (or AP) 470 transmits, to terminal 1050 in FIG. 10, a modulated signal as radio waves.

Radio device 453 included in terminal 1050 in FIG. 10 performs processing such as demodulation and error correction decoding on the modulated signal received as radio waves to obtain reception data 1056. Display 157 displays a display based on reception data 1056.

Figure 11:
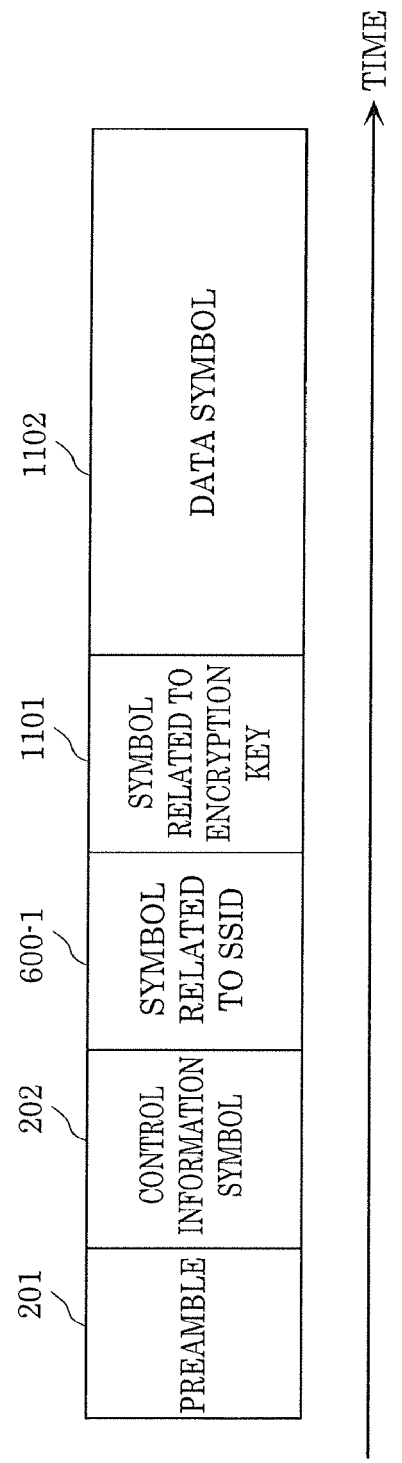
FIG. 11 illustrates one example of a frame configuration of a modulated signal transmitted by a second device according to Embodiment 4.

FIG. 11 illustrates one example of a configuration of a frame of a modulated signal transmitted by second device 1000 in FIG. 10. In FIG. 11, time is represented on the horizontal axis, and symbols that are the same as in FIG. 2 and FIG. 6 share like reference marks. Accordingly, repeated description thereof will be omitted.

Symbol 600-1 related to an SSID is a symbol for transmitting information 1001-1 related to an SSID in FIG. 10, and symbol 1101 related to an encryption key is a symbol for transmitting information 1001-2 related to an encryption key in FIG. 10. Data symbol 1102 is a symbol for transmitting data 1002.

The second device transmits preamble 201, control information symbol 202, symbol 600-1 related to an SSID, symbol 1101 related to an encryption key, and data symbol 1102. Note that second device 1000 in FIG. 10 may transmit a frame including symbols other than the symbols illustrated in FIG. 11. Moreover, the frame configuration, including the order in which the symbols are transmitted, is not limited to the configuration illustrated in FIG. 11.

Figure 12:
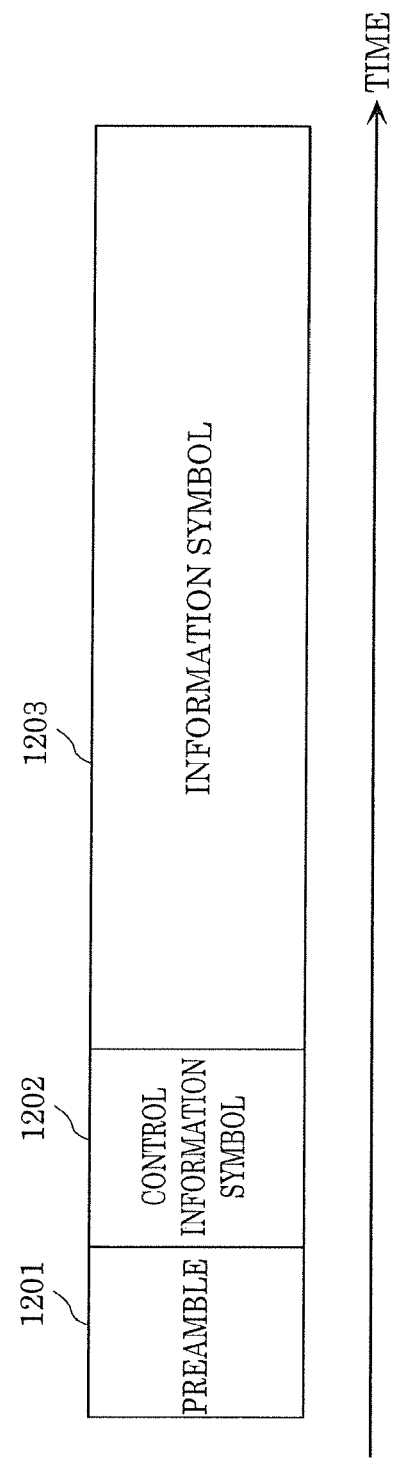
FIG. 12 illustrates one example of a frame configuration of a modulated signal transmitted by a radio device included in a terminal according to Embodiment 4.

FIG. 12 illustrates one example of a configuration of a frame of a modulated signal transmitted by radio device 453 included in terminal 1050 in FIG. 10. In FIG. 12, time is represented on the horizontal axis. As illustrated in FIG. 12, radio device 453 included in terminal 1050 in FIG. 10 transmits, for example, preamble 1201, and then transmits control information symbol 1202 and information symbol 1203.

Here, preamble 1201 is a symbol used for base station (or AP) 470 that receives the modulated signal transmitted by radio device 453 in terminal 1050 in FIG. 10 to perform, for example, signal detection, temporal synchronization, frame synchronization, frequency synchronization, and frequency offset estimation.

Control information symbol 1202 includes data such as information related to the error correction encoding scheme method and/or demodulation scheme used in the generation of the modulated signal, information related to frame configuration, and information related to the transmission method used, and base station (or AP) 470, for example, demodulates the modulated signal based on the information included in control information symbol 1202.

Information symbol 1203 is a symbol for radio device 453 included in terminal 1050 in FIG. 10 to transmit data.

Note that radio device 453 included in terminal 1050 in FIG. 10 may transmit a frame including symbols other than the symbols illustrated in FIG. 12 (for example, a frame including a pilot symbol (reference symbol) midway through the information symbol). Moreover, the frame configuration, including the order in which the symbols are transmitted, is not limited to the configuration illustrated in FIG. 12. In FIG. 12, a plurality of symbols may be present along the frequency axis, that is to say, symbols may be present on a plurality of frequencies (a plurality of carriers).

Note that in Embodiment 3, when radio device 453 included in terminal 1050 in FIG. 4 transmits a modulated signal, the frame configuration illustrated in FIG. 12 may be used.

FIG. 7 illustrates one example of a configuration of a frame of a modulated signal transmitted by base station 470 in FIG. 10. In FIG. 7, time is represented on the horizontal axis. As illustrated in FIG. 7, base station 470 transmits, for example, preamble 701, and then transmits control information symbol 702 and information symbol 703.

Here, preamble 701 is a symbol for radio device 453 included in terminal 1050 in FIG. 10, which receives the modulated signal transmitted by base station 470, to perform, for example, signal detection, temporal synchronization, frame synchronization, frequency synchronization, and/or frequency offset estimation.

Control information symbol 702 includes data such as information related to the error correction encoding scheme method and/or demodulation scheme used in the generation of the modulated signal, information related to frame configuration, and information related to the transmission method used, and radio device 453 included in terminal 1050 in FIG. 10, for example, demodulates the modulated signal based on the information included in this symbol.

Information symbol 703 is a symbol for base station (or AP) 470 in FIG. 10 to transmit data.

Note that base station (or AP) 470 in FIG. 10 may transmit a frame including symbols other than the symbols illustrated in FIG. 7 (for example, a frame including a pilot symbol (reference symbol) midway through the information symbol). Moreover, the frame configuration, including the order in which the symbols are transmitted, is not limited to the configuration illustrated in FIG. 7. In FIG. 7, a plurality of symbols may be present along the frequency axis, that is to say, symbols may be present on a plurality of frequencies (a plurality of carriers).

Moreover, for example, a modulated signal that has the frame configuration illustrated in FIG. 11 and is transmitted by second device 1000 being transmitted at a regular timing, e.g., repeatedly transmitted is conceivable. This makes it possible for a plurality of terminals to implement the operations described above.

Figure 13:
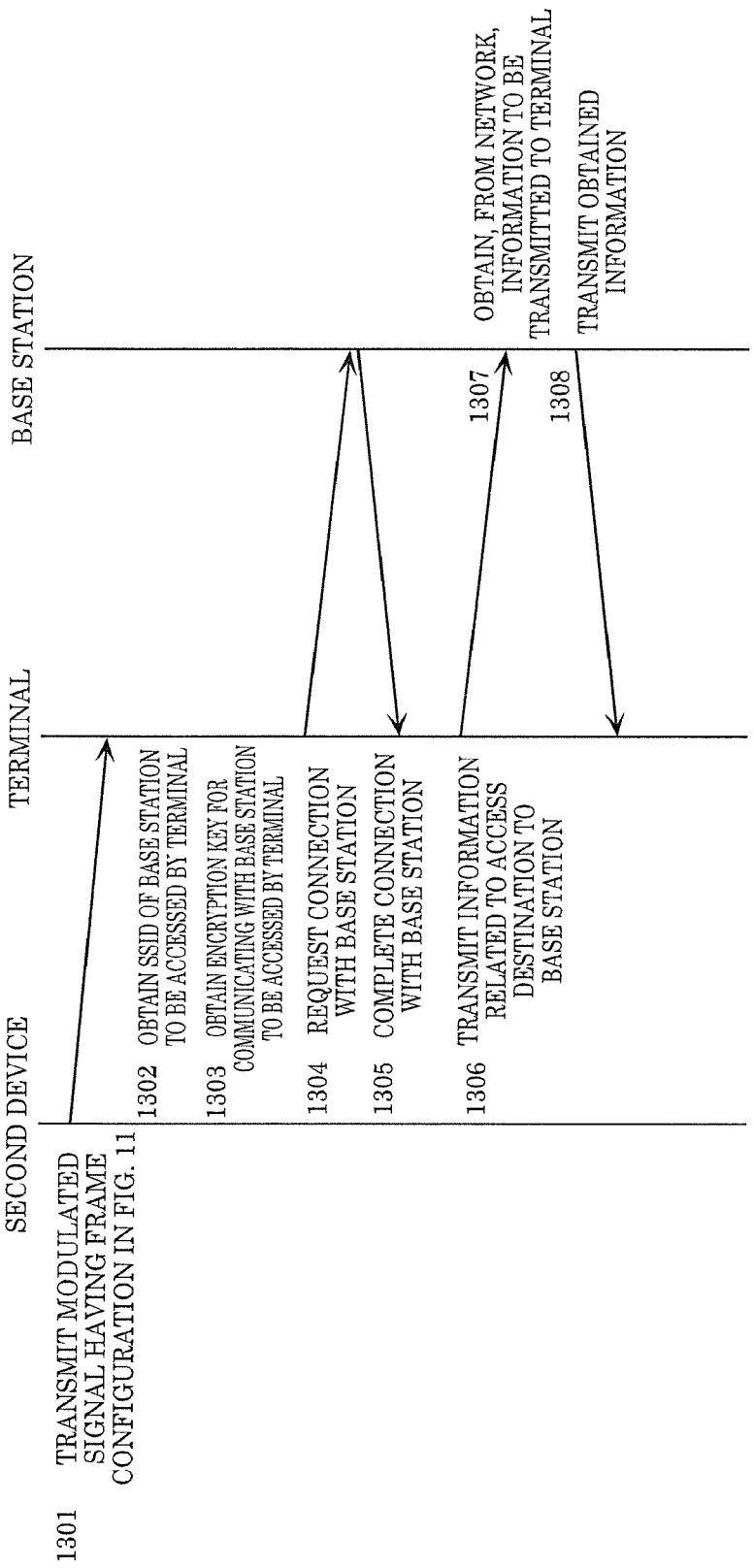
FIG. 13 is a flow chart of one example of processes performed by a device, terminal, and base station according to Embodiment 4.

FIG. 13 is a flow chart illustrating one example of processes implemented by second device 1000, terminal 1050, and base station (or AP) 470 in FIG. 10.

First, as 1301 in FIG. 13 illustrates, second device 1000 in FIG. 10 transmits a modulated signal having the frame configuration illustrated in FIG. 11.

Likewise, as 1302 in FIG. 13 illustrates, the modulated signal transmitted by second device 1000 in FIG. 10 is received, and terminal 1050 in FIG. 10 obtains the SSID of the base station to be accessed by terminal 1050.

Likewise, as 1303 in FIG. 13 illustrates, terminal 1050 in FIG. 10 obtains an encryption key to be used for communicating with base station 470 to be accessed by the terminal.

Terminal 1050 in FIG. 10 requests connection with base station 470 in FIG. 10 over radio waves (1304).

As 1305 in FIG. 13 illustrates, terminal 1050 in FIG. 10 completes the connection with base station 470 in FIG. 10 upon receiving a response from base station 470 in FIG. 10.

As 1306 in FIG. 13 illustrates, terminal 1050 in FIG. 10 transmits information on the connection destination to base station 470 in FIG. 10 using radio waves.

Then, as 1307 in FIG. 13 illustrates, base station 470 in FIG. 10 obtains information to be transmitted to terminal 1050 in FIG. 10 from the network.

As 1308 in FIG. 13 illustrates, base station 470 in FIG. 10 transmits the obtained information to terminal 1050 in FIG. 10 using radio waves, and terminal 1050 in FIG. 10 obtains the information.

For example, when necessary, terminal 1050 in FIG. 10 obtains required information from the network via base station 470 in FIG. 10.

As described above, based on the SSID information and the encryption key information transmitted from the second device, the terminal connects to the base station (or AP) and obtains information, whereby an advantageous effect that it is possible to securely obtain information via the base station (or AP) whose security has been authenticated can be achieved. This is because, when information from a visible light modulated signal is obtained, since it is visible light, the user can easily determine whether the source of information is secure or not.

For example, when an SSID is obtained from a modulated signal transmitted by a wireless LAN over radio waves, it is difficult for the user to determine which device transmitted the radio waves. Accordingly, from the viewpoint of ensuring information security, obtaining the SSID via visible light communication is more suitable.

Note that in this embodiment, the second device is exemplified as transmitting encryption key information, but, for example, when the base station (or AP) does not perform encrypted communication using an encryption key, the second device can transmit only the information related to an SSID without transmitting the encryption key information, that is, the second device may be implemented without the configuration related to an encryption key.

Moreover, the configuration of the second device is not limited to the configuration illustrated in FIG. 10, the configuration of the terminal is not limited to the configuration illustrated in FIG. 10, and the configuration of the connection destination of the base station is not limited to the configuration illustrated in FIG. 10.

Although in this embodiment, only one base station (or AP) is exemplified in the configuration illustrated in FIG. 10, a plurality of (secure) base stations (or APs) accessible by the terminal may be included (note that these base stations and the terminal transmit and receive modulated signals using radio waves). Here, the symbol related to an SSID transmitted by second device 1000 in FIG. 10 may include information indicating the SSIDs of the plurality of base stations (or APs). Moreover, the symbol related to an encryption key transmitted by second device 1000 in FIG. 10 may include encryption key information used to connect to the plurality of base stations (or APs). Terminal 1050 in FIG. 10 may select a base station (or AP) to wirelessly connect to based on the information on the SSIDs of the base stations and the encryption key information (or connect to the plurality of base stations (or APs)).

For example, assume there are three base stations (or APs). The three base stations are named base station #A, base station #B, and base station #C. The SSID of base station #A is "abcdef", the SSID of base station #B is "ghijk", and the SSID of base station #C is "pqrstu", the encryption key for connecting with base station #A is "123", the encryption key for connecting with base station #B is "456", and the encryption key for connecting with base station #C is "789".

In such cases, symbol 600-1 related to an SSID in the frame configuration illustrated in FIG. 11 of the modulated signal transmitted by the second device includes information related to the SSID "abcdef" of base station #A, the SSID "ghijk" of base station #B, and the SSID "pqrstu" of base station #C. The symbol 1101 related to an encryption key having the frame configuration illustrated in FIG. 11 includes information related to the encryption key "123" for connecting with base station #A, the encryption key "456" for connecting with base station #B, and the encryption key "789" for connecting with base station #C.

Terminal 1050 in FIG. 10 receives symbol 600-1 related to an SSID and thus obtains the SSID "abcdef" of base station #A, the SSID "ghijk" of base station #B, and the SSID "pqrstu" of base station #C, receives symbol 1101 related to an encryption key and thus obtains the encryption key "123" for connecting with base station #A, the encryption key "456" for connecting with base station #B, and the encryption key "789" for connecting with base station #C. Then, based on this information, terminal 1050 in FIG. 10 selects a base station (or AP) to wirelessly connect to (for example, via radio waves), and connects to the selected base station (or AP).

As described in this embodiment, as a result of the terminal setting which base station to access, utilizing a light source, exemplified here as an LED light source, a mode for making a special setting for processes for establishing a wireless connection between the terminal and base station in the modulated signal for connection over radio waves that is transmitted by the terminal is not required, and a mode for making a special setting for processes for establishing a wireless connection between the terminal and base station in the modulated signal for connection over radio waves that is transmitted by the base station is not required, whereby an advantageous effect that wireless communication data transmission efficiency improves can be achieved.

As described above, the encryption key may be an encryption key for an SSID on a wireless LAN, may be an encryption key for restricting the form of connection used, the form of service used, and/or the connectivity range of the network (in other words, any encryption key that is restrictive is sufficient).

Embodiment 5 (SSID and Password Separation)

Figure 14:
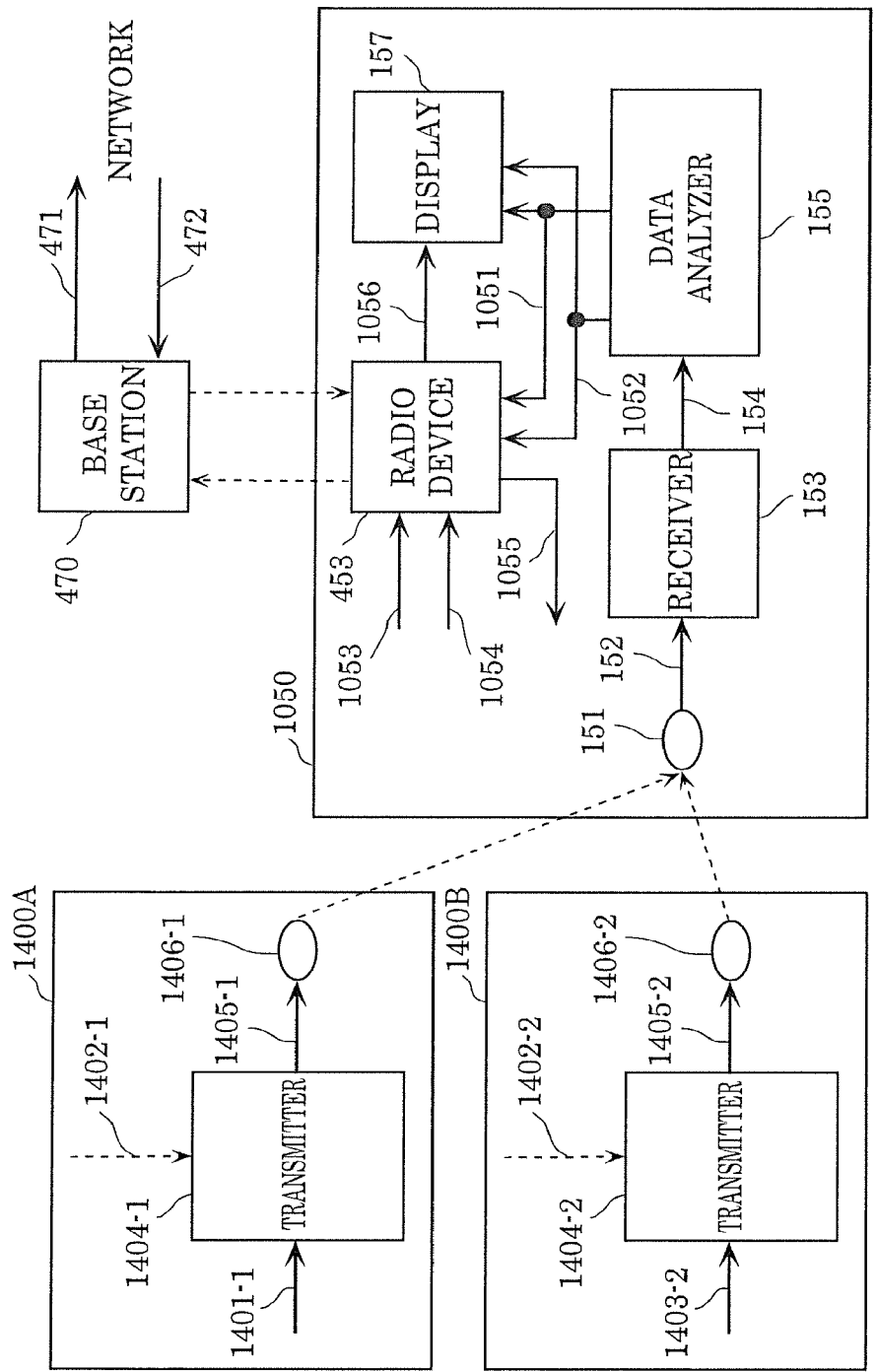
FIG. 14 illustrates one example of a configuration of devices, a terminal, and a base station according to Embodiment 5.

FIG. 14 illustrates one example of configurations according to this embodiment of: devices including, for example, an LED light source, lamp, light source, and/or light that emits visible light; a terminal; and, for example, a base station that communicates with the terminal. The communication system in FIG. 14 includes: device 1400A and 1400B each including, for example, an LED light source, lamp, light source, and/or light that emits visible light; terminal 1050; and, for example, base station 470 that communicates with terminal 1050. Note that device 1400A in FIG. 14 is referred to as a "third device" in this embodiment, and device 1400B in FIG. 14 is referred to as a "fourth device" in this embodiment. Note that in terminal 1050 in FIG. 14, operations that are the same as in FIG. 1 and FIG. 10 share like reference marks. Regarding the base station or AP as well, operations that are the same as in FIG. 4 have the same reference marks as in FIG. 4.

Note that communication between radio device 453 and base station 470 in FIG. 14 is performed using, for example, radio waves.

In third device 1400A in FIG. 14, transmitter 1404-1 receives inputs of information 1401-1 related to an SSID and data 1402-1, and based on these input signals, generates a (optical) modulated signal and outputs modulated signal 1405-1. Modulated signal 1405-1 is transmitted from light source 1406-1.

In fourth device 1400B in FIG. 14, transmitter 1404-2 receives inputs of information 1403-2 related to an encryption key and data 1402-2, and based on these input signals, generates a (optical) modulated signal and outputs modulated signal 1405-2. Modulated signal 1405-2 is transmitted from light source 1406-2.

Next, information 1401-1 related to an SSID and information 1403-2 related to an encryption key will be described.

First, information 1401-1 related to an SSID will be described.

Information 1401-1 related to an SSID is information indicating the SSID of base station (or AP) 470 in FIG. 14. In other words, third device 1400A can provide access over radio waves to base station 470, which is a secure access destination for the terminal With this, terminal 1050 in FIG. 14 can achieve the advantageous effect of being able to securely obtain information from base station (or AP) 470.

Note that when terminal 1050 receives an optical signal transmitted via a predetermined scheme, it may be determined that the notified SSID is the SSID of a secure base station, and, alternatively, processing for determining whether the SSID is secure or not may be performed. For example, device 1400A may transmit a predetermined identifier in an optical signal, and the terminal may determine whether the notified SSID is the SSID of a secure base station or not based on the received identifier.

Note that although FIG. 14 only illustrates base station (or AP) 470, for example, when there is a base station (or AP) other than base station (or AP) 470, terminal 1050 in FIG. 14 accesses base station (or AP) 470 to obtain information.

Information 1403-2 related to an encryption key is information related to an encryption key required for terminal 1050 in FIG. 14 to establish communication with base station (or AP) 470 in FIG. 14. Encrypted communication is possible between terminal 1050 in FIG. 14 and base station (or AP) 470 as a result of terminal 1050 in FIG. 14 obtaining this information from fourth device 1400B in FIG. 14.

Terminal 1050 in FIG. 14 receives the modulated signal transmitted by third device 1400A.

Light receiver 151 included in terminal 1050, examples of which include an image sensor such as a CMOS or organic CMOS image sensor, receives the modulated signal transmitted by third device 1400A. Receiver 153 receives an input of reception signal 152 received by light receiver 151, performs processing such as demodulation and error correction decoding on the reception signal, and outputs reception data 154.

Data analyzer 155 receives an input of reception data 154, and outputs, based on the reception data, for example, information 1051 on the SSID of the base station (470) to be connected to.

Accordingly, radio device 453 included in terminal 1050 obtains information on the SSID of the base station to be connected to over radio waves by radio device 453, from information 1051 on the SSID.

Next, terminal 1050 in FIG. 14 receives the modulated signal transmitted by fourth device 1400B.

Light receiver 151 included in terminal 1050, examples of which include an image sensor such as a CMOS or organic CMOS image sensor, receives the modulated signal transmitted by fourth device 1400B. Receiver 153 receives an input of reception signal 152 received by light receiver 151, performs processing such as demodulation and error correction decoding on the reception signal, and outputs reception data 154.

Data analyzer 155 receives an input of reception data 154, and outputs, based on the reception data, for example, information 1052 on the encryption key for communication with the base station (470) to be connected to. For example, in a wireless local area network (LAN), examples of encryption schemes include wired equivalent privacy (WEP), Wi-Fi protected access (WPA), and Wi-Fi protected access 2 (WPA2) (pre-shared key (PSK) mode, extended authentication protocol (EAP) mode). However, the encryption method is not limited to these examples.

Accordingly, radio device 453 included in terminal 1050 obtains encryption key information for the base station to be connected to by radio device 453, from information 1052 on the encryption key for communication with the base station (470) to be connected to (for example, over radio waves).

Display 157 receives inputs of information 1051 on the SSID and information 1052 on the encryption key, and, for example, displays the SSID of the communication partner to be accessed by radio device 453 included in the terminal, and the encryption key (this display is referred to as a "first display" in this embodiment).

For example, after the first display, radio device 453 included in terminal 1050 in FIG. 14 receives inputs of information 1051 on the SSID and information 1052 on the encryption key, and establishes a connection with base station (or AP) 470 (for example, the connection uses radio waves). Here, when base station (or AP) 470 also communicates with radio device 453 in terminal 1050 in FIG. 14, base station (or AP) 470 transmits a modulated signal using, for example, radio waves.

Thereafter, radio device 453 included in terminal 1050 in FIG. 14 receives inputs of data 1053 and control signal 1054, demodulates data 1053 in accordance with control signal 1054, and transmits a modulated signal as radio waves.

Then, for example, base station (or AP) 470 transmits data to the network (471) and receives data (472) from the network. Thereafter, for example, base station (or AP) 470 transmits, to terminal 1050 in FIG. 14, a modulated signal as radio waves.

Radio device 453 included in terminal 1050 in FIG. 14 performs processing such as demodulation and error correction decoding on the received modulated signal to obtain reception data 1056. Display 157 displays a display based on reception data 1056.

Figure 15:
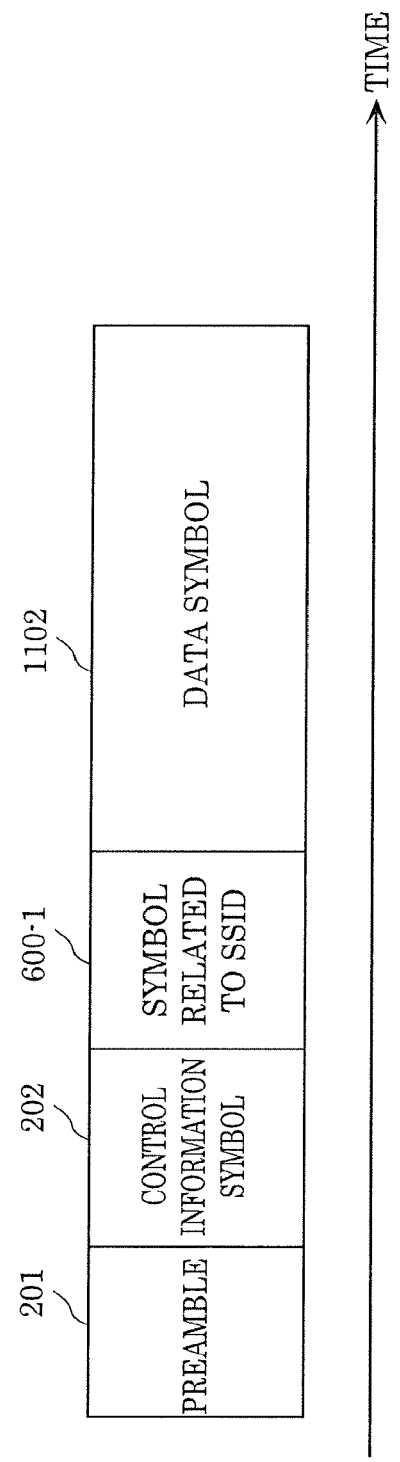
FIG. 15 illustrates one example of a frame configuration of a modulated signal transmitted by a third device according to Embodiment 5.

FIG. 15 illustrates one example of a configuration of a frame of a modulated signal transmitted by third device 1400A in FIG. 14. In FIG. 15, time is represented on the horizontal axis, and symbols that are the same as in FIG. 2, FIG. 6, and FIG. 11 share like reference marks. Accordingly, repeated description thereof will be omitted.

Symbol 600-1 related to an SSID is a symbol for transmitting information 1401-1 related to an SSID in FIG. 14. Data symbol 1102 is a symbol for transmitting data 1402-1.

Third device 1400A transmits preamble 201, control information symbol 202, symbol 600-1 related to an SSID, and data symbol 1102. Note that third device 1400A in FIG. 14 may transmit a frame including symbols other than the symbols illustrated in FIG. 15. Moreover, the frame configuration, including the order in which the symbols are transmitted, is not limited to the configuration illustrated in FIG. 15.

Figure 16:
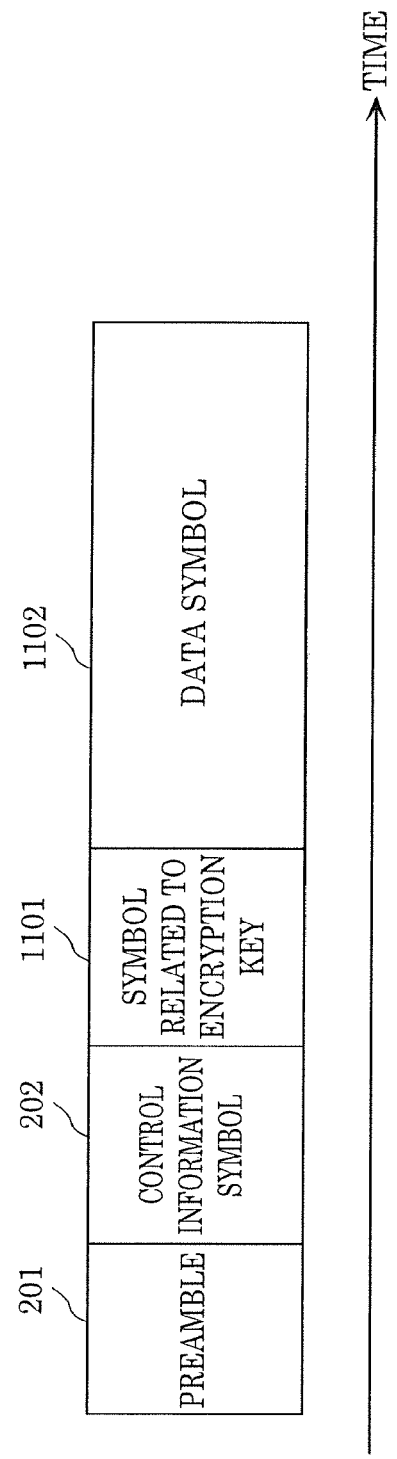
FIG. 16 illustrates one example of a frame configuration of a modulated signal transmitted by a fourth device according to Embodiment 5.

FIG. 16 illustrates one example of a configuration of a frame of a modulated signal transmitted by fourth device 1400B in FIG. 14. In FIG. 16, time is represented on the horizontal axis, and symbols that are the same as in FIG. 2 and FIG. 11 share like reference marks. Accordingly, repeated description thereof will be omitted.

Symbol 1101 related to an encryption key is a symbol for transmitting information 1403-2 related to an encryption key in FIG. 14. Data symbol 1102 is a symbol for transmitting data 1402-2.

Fourth device 1400B transmits preamble 201, control information symbol 202, symbol 1101 related to an encryption key, and data symbol 1102. Note that fourth device 1400B in FIG. 14 may transmit a frame including symbols other than the symbols illustrated in FIG. 16. Moreover, the frame configuration, including the order in which the symbols are transmitted, is not limited to the configuration illustrated in FIG. 16.

FIG. 12 illustrates one example of a configuration of a frame of a modulated signal transmitted by radio device 453 included in terminal 1050 in FIG. 14. In FIG. 12, time is represented on the horizontal axis. As illustrated in FIG. 12, radio device 453 included in terminal 1050 in FIG. 14 transmits, for example, preamble 1201, and then transmits control information symbol 1202 and information symbol 1203.

Here, preamble 1201 is a symbol used for base station (or AP) 470 that receives the modulated signal transmitted by radio device 453 in terminal 1050 in FIG. 14 to perform, for example, signal detection, temporal synchronization, frame synchronization, frequency synchronization, and frequency offset estimation.

Control information symbol 1202 includes data such as information related to the error correction encoding scheme method and/or demodulation scheme used in the generation of the modulated signal, information related to frame configuration, and information related to the transmission method used, and base station (or AP) 470, for example, demodulates the modulated signal based on the information included in control information symbol 1202.

Information symbol 1203 is a symbol for radio device 453 included in terminal 1050 in FIG. 14 to transmit data.

Note that radio device 453 included in terminal 1050 in FIG. 14 may transmit a frame including symbols other than the symbols illustrated in FIG. 12 (for example, a frame including a pilot symbol (reference symbol) midway through the information symbol). Moreover, the frame configuration, including the order in which the symbols are transmitted, is not limited to the configuration illustrated in FIG. 12. In FIG. 12, a plurality of symbols may be present along the frequency axis, that is to say, symbols may be present on a plurality of frequencies (a plurality of carriers).

FIG. 7 illustrates one example of a configuration of a frame of a modulated signal transmitted by base station 470 in FIG. 14. In FIG. 7, time is represented on the horizontal axis. As illustrated in FIG. 7, base station 470 transmits, for example, preamble 701, and then transmits control information symbol 702 and information symbol 703.

Here, preamble 701 is a symbol for radio device 453 included in terminal 1050 in FIG. 14, which receives the modulated signal transmitted by base station 470, to perform, for example, signal detection, temporal synchronization, frame synchronization, frequency synchronization, and/or frequency offset estimation.

Control information symbol 702 includes data such as information related to the error correction encoding scheme method and/or demodulation scheme used in the generation of the modulated signal, information related to frame configuration, and information related to the transmission method used, and radio device 453 included in terminal 1050 in FIG. 14, for example, demodulates the modulated signal based on the information included in this symbol.

Information symbol 703 is a symbol for base station (or AP) 470 in FIG. 14 to transmit data.

Note that base station (or AP) 470 in FIG. 14 may transmit a frame including symbols other than the symbols illustrated in FIG. 7 (for example, a frame including a pilot symbol (reference symbol) midway through the information symbol). Moreover, the frame configuration, including the order in which the symbols are transmitted, is not limited to the configuration illustrated in FIG. 7. In FIG. 7, a plurality of symbols may be present along the frequency axis, that is to say, symbols may be present on a plurality of frequencies (a plurality of carriers).

Moreover, for example, a modulated signal that has the frame configuration illustrated in FIG. 15 and is transmitted by third device 1400A being transmitted at a regular timing, e.g., repeatedly transmitted is conceivable. This makes it possible for a plurality of terminals to implement the operations described above.

Similarly, a modulated signal that has the frame configuration illustrated in FIG. 16 and is transmitted by fourth device 1400B being transmitted at a regular timing, e.g., repeatedly transmitted is conceivable. This makes it possible for a plurality of terminals to implement the operations described above.

Figure 17:
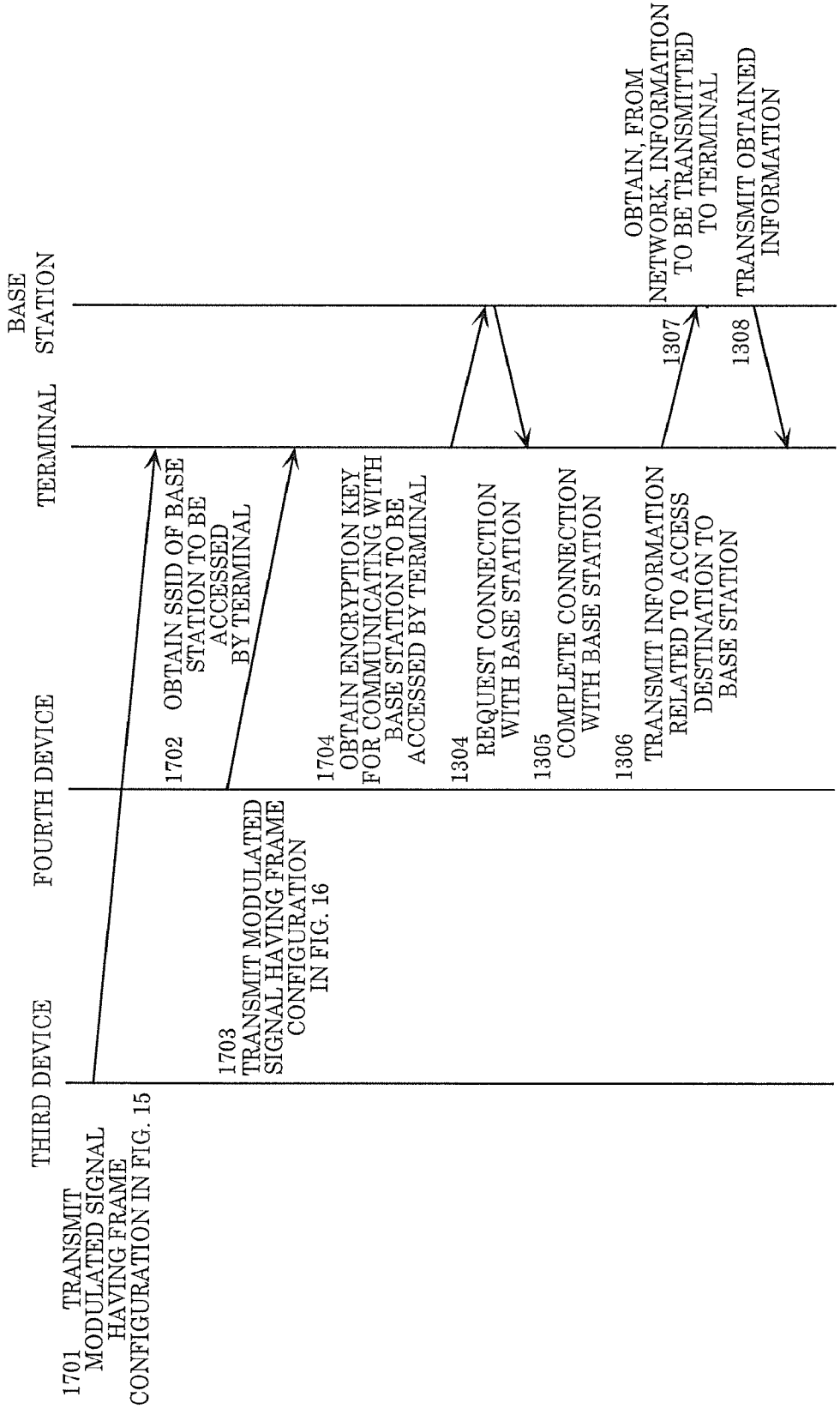
FIG. 17 is a flow chart of a first example of processes performed by a third device, a fourth device, a terminal, and a base station according to Embodiment 5.

FIG. 17 is a flow chart illustrating a first example of processes implemented by third device 1400A, fourth device 1400B, terminal 1050, and base station (or AP) 470 in FIG. 14. Note that in FIG. 17, operations that are the same as in FIG. 13 share like reference marks.

First, as 1701 in FIG. 17 illustrates, third device 1400A in FIG. 14 transmits a modulated signal having the frame configuration illustrated in FIG. 15.

As 1702 in FIG. 17 illustrates, the modulated signal transmitted by third device 1400A in FIG. 14 is received, and terminal 1050 in FIG. 14 obtains the SSID of the base station to be accessed by terminal 1050.

Next, as 1703 in FIG. 17 illustrates, fourth device 1400B in FIG. 14 transmits a modulated signal having the frame configuration illustrated in FIG. 16.

As 1704 in FIG. 17 illustrates, the modulated signal transmitted by fourth device 1400B in FIG. 14 is received, and terminal 1050 in FIG. 14 obtains an encryption key to be used for communicating with base station 470 to be accessed by the terminal.

Terminal 1050 in FIG. 14 requests connection with base station 470 in FIG. 14 over radio waves (1304).

As 1305 in FIG. 17 illustrates, terminal 1050 in FIG. 14 completes the connection with base station 470 in FIG. 14 upon receiving a response from base station 470 in FIG. 14.

As 1306 in FIG. 17 illustrates, terminal 1050 in FIG. 14 transmits information on the connection destination to base station 470 in FIG. 14 using radio waves.

Then, as 1307 in FIG. 17 illustrates, base station 470 in FIG. 14 obtains information to be transmitted to terminal 1050 in FIG. 14 from the network.

As 1308 in FIG. 17 illustrates, base station 470 in FIG. 14 transmits the obtained information to terminal 1050 in FIG. 14 using radio waves, and terminal 1050 in FIG. 14 obtains the information.

For example, when necessary, terminal 1050 in FIG. 14 obtains required information from the network via base station 470 in FIG. 14.

Figure 18:
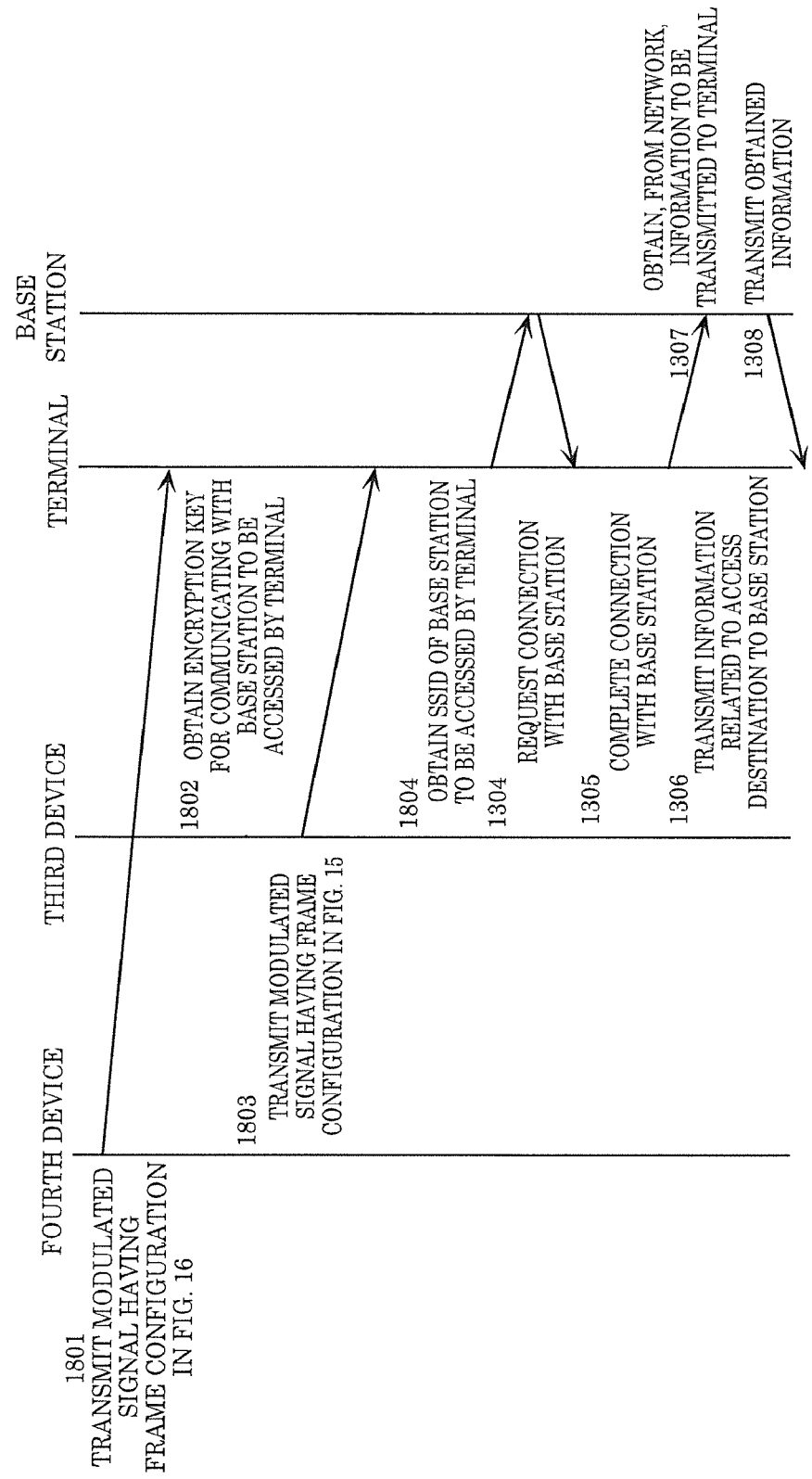
FIG. 18 is a flow chart of a second example of processes performed by a third device, a fourth device, a terminal, and a base station according to Embodiment 5.

FIG. 18 is a flow chart illustrating a second example of the above-described processes implemented by third device 1400A, fourth device 1400B, terminal 1050, and base station (or AP) 470 in FIG. 14. Note that in FIG. 18, operations that are the same as in FIG. 13 share like reference marks.

First, as 1801 in FIG. 18 illustrates, fourth device 1400B in FIG. 14 transmits a modulated signal having the frame configuration illustrated in FIG. 16.

As 1802 in FIG. 18 illustrates, the modulated signal transmitted by fourth device 1400B in FIG. 14 is received, and terminal 1050 in FIG. 14 obtains an encryption key to be used for communicating with the base station to be accessed by terminal 1050.

Next, as 1803 in FIG. 18 illustrates, third device 1400A in FIG. 14 transmits a modulated signal having the frame configuration illustrated in FIG. 15.

As 1804 in FIG. 18 illustrates, the modulated signal transmitted by third device 1400A in FIG. 14 is received, and terminal 1050 in FIG. 14 obtains the SSID of base station 470 to be accessed by the terminal.

Terminal 1050 in FIG. 14 requests connection with base station 470 in FIG. 14 over radio waves (1304).

As 1305 in FIG. 18 illustrates, terminal 1050 in FIG. 14 completes the connection with base station 470 in FIG. 14 upon receiving a response from base station 470 in FIG. 14.

As 1306 in FIG. 18 illustrates, terminal 1050 in FIG. 14 transmits information on the connection destination to base station 470 in FIG. 14 using radio waves.

Then, as 1307 in FIG. 18 illustrates, base station 470 in FIG. 14 obtains information to be transmitted to terminal 1050 in FIG. 14 from the network.

As 1308 in FIG. 18 illustrates, base station 470 in FIG. 14 transmits the obtained information to terminal 1050 in FIG. 14 using radio waves, and terminal 1050 in FIG. 14 obtains the information.

For example, when necessary, terminal 1050 in FIG. 14 obtains required information from the network via base station 470 in FIG. 14.

As described above, based on the SSID information and the encryption key information transmitted from the third and fourth devices, the terminal connects to the base station (or AP) and obtains information, whereby an advantageous effect that it is possible to securely obtain information via the base station (or AP) whose security has been authenticated can be achieved. This is because, when information from a visible light modulated signal is obtained, since it is visible light, the user can easily determine whether the source of information is secure or not.

For example, when an SSID is obtained from a modulated signal transmitted by a wireless LAN over radio waves, it is difficult for the user to determine which device transmitted the radio waves. Accordingly, from the viewpoint of ensuring information security, obtaining the SSID via visible light communication is more suitable.

Note that in this embodiment, the fourth device is exemplified as transmitting encryption key information, but, for example, when the base station (or AP) does not perform encrypted communication using an encryption key, the fourth device can transmit only the information related to an SSID without transmitting the encryption key information, that is, the fourth device may be implemented without the configuration related to an encryption key.

Moreover, as described in this embodiment, by separating the device for transmitting information related to an SSID and the device for transmitting information related to an encryption key, the terminal can implement even more secure communication with the base station.

Figure 19:
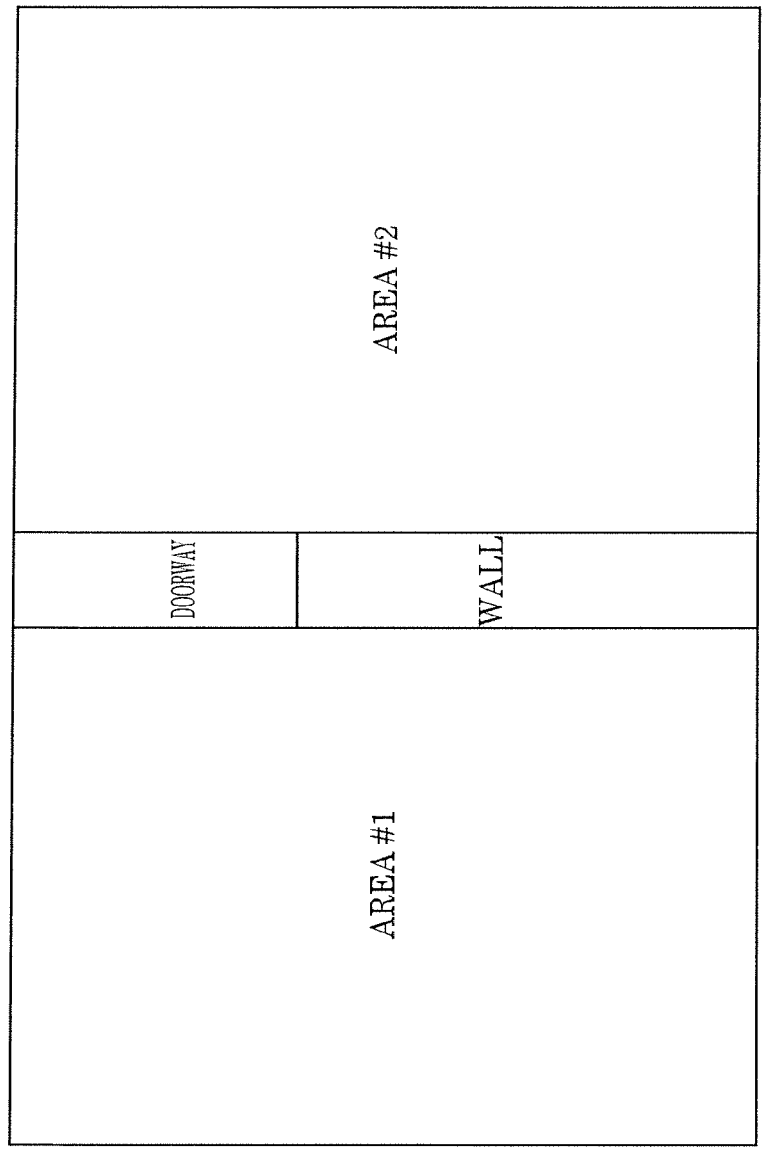
FIG. 19 illustrates a space in which a third device, a fourth device, a terminal, and a base station according to Embodiment 5 are disposed.

For example, consider the space illustrated in FIG. 19. As illustrated in FIG. 19, the space includes area #1 and area #2, and a wall and a doorway between area #1 and area #2. In this example, movement from area #1 to area #2 and movement from area #2 to area #1 is only possible through the doorway.

A base station (or AP), a third device, and a fourth device are disposed in area #1 in FIG. 19. Only a third device is disposed in area #2.

Moreover, assume that the radio waves transmitted by the base station (or AP) are receivable in either of areas #1 or #2. Here, a terminal in area #1 in which a fourth device is disposed can communicate with the base station. Moreover, even when a terminal connected to the base station in area #1 moves to area #2, communication with the base station is still possible.

When a terminal connected to the base station in area #1 moves somewhere other than area #1 or area #2, and then returns to either area #1 or area #2, communication with the base station is possible.

However, a terminal that cannot enter area #1 cannot obtain an encryption key. In such cases, the terminal can only know the SSID of the base station (or AP). Here, communication with the base station via a service that can be accepted with nothing more than knowledge of the SSID may be received by the terminal.

Accordingly, only a terminal that can enter area #1 can communicate with the base station, and as a result, communication security can be assured. Moreover, this makes it possible to construct a system that can provide different services for different areas.

Note that when the encryption key for the terminal to communicate with the base station changes (for example, on a per time interval basis), a previous encryption key cannot be used to communicate with the base station. Using such a system makes it possible to provide secure communication.

As described above, the encryption key may be an encryption key for an SSID on a wireless LAN, may be an encryption key for restricting the form of connection used, the form of service used, and/or the connectivity range of the network (in other words, any encryption key that is restrictive is sufficient).

The configurations of the third and fourth devices are not limited to the configurations illustrated in FIG. 14, the configuration of the terminal is not limited to the configuration illustrated in FIG. 14, and the configuration of the connection destination of the base station is not limited to the configuration illustrated in FIG. 14.

In this embodiment, although only one base station (or AP) is exemplified in the configuration illustrated in FIG. 14, a plurality of (secure) base stations (or APs) accessible by the terminal may be included. Here, the symbol related to an SSID transmitted by third device 1400A in FIG. 14 may include information indicating the SSIDs of the plurality of base stations (or APs). Moreover, the symbol related to an encryption key transmitted by fourth device 1400B in FIG. 14 may include encryption key information used to connect to the plurality of base stations (or APs). Terminal 1050 in FIG. 14 may select a base station (or AP) to wirelessly connect to based on the encryption key information and the information on the SSIDs of the base stations (or connect to the plurality of base stations (or APs)).

For example, assume there are three base stations (or APs). The three base stations are named base station #A, base station #B, and base station #C. The SSID of base station #A is "abcdef", the SSID of base station #B is "ghijk", and the SSID of base station #C is "pqrstu", the encryption key for connecting with base station #A is "123", the encryption key for connecting with base station #B is "456", and the encryption key for connecting with base station #C is "789".

In such cases, symbol 600-1 related to an SSID in the frame configuration illustrated in FIG. 15 of the modulated signal transmitted by the third device includes information related to the SSID "abcdef" of base station #A, the SSID "ghijk" of base station #B, and the SSID "pqrstu" of base station #C. The symbol 1101 related to an encryption key having the frame configuration illustrated in FIG. 16 of the modulated signal transmitted by the fourth device includes information related to the encryption key "123" for connecting with base station #A, the encryption key "456" for connecting with base station #B, and the encryption key "789" for connecting with base station #C.

Terminal 1050 in FIG. 14 receives symbol 600-1 related to an SSID and thus obtains the SSID "abcdef" of base station #A, the SSID "ghijk" of base station #B, and the SSID "pqrstu" of base station #C, receives symbol 1101 related to an encryption key and thus obtains the encryption key "123" for connecting with base station #A, the encryption key "456" for connecting with base station #B, and the encryption key "789" for connecting with base station #C. Then, based on this information, terminal 1050 in FIG. 14 selects a base station (or AP) to wirelessly connect to (for example, via radio waves), and connects to the selected base station (or AP).

As described in this embodiment, as a result of the terminal setting which base station to access, utilizing a light source, exemplified here as an LED light source, a mode for making a special setting for processes for establishing a wireless connection between the terminal and base station in the modulated signal for connection over radio waves that is transmitted by the terminal is not required, and a mode for making a special setting for processes for establishing a wireless connection between the terminal and base station in the modulated signal for connection over radio waves that is transmitted by the base station is not required, whereby an advantageous effect that wireless communication data transmission efficiency improves can be achieved.

Embodiment 6 (Base Station Includes LED)

Figure 20:
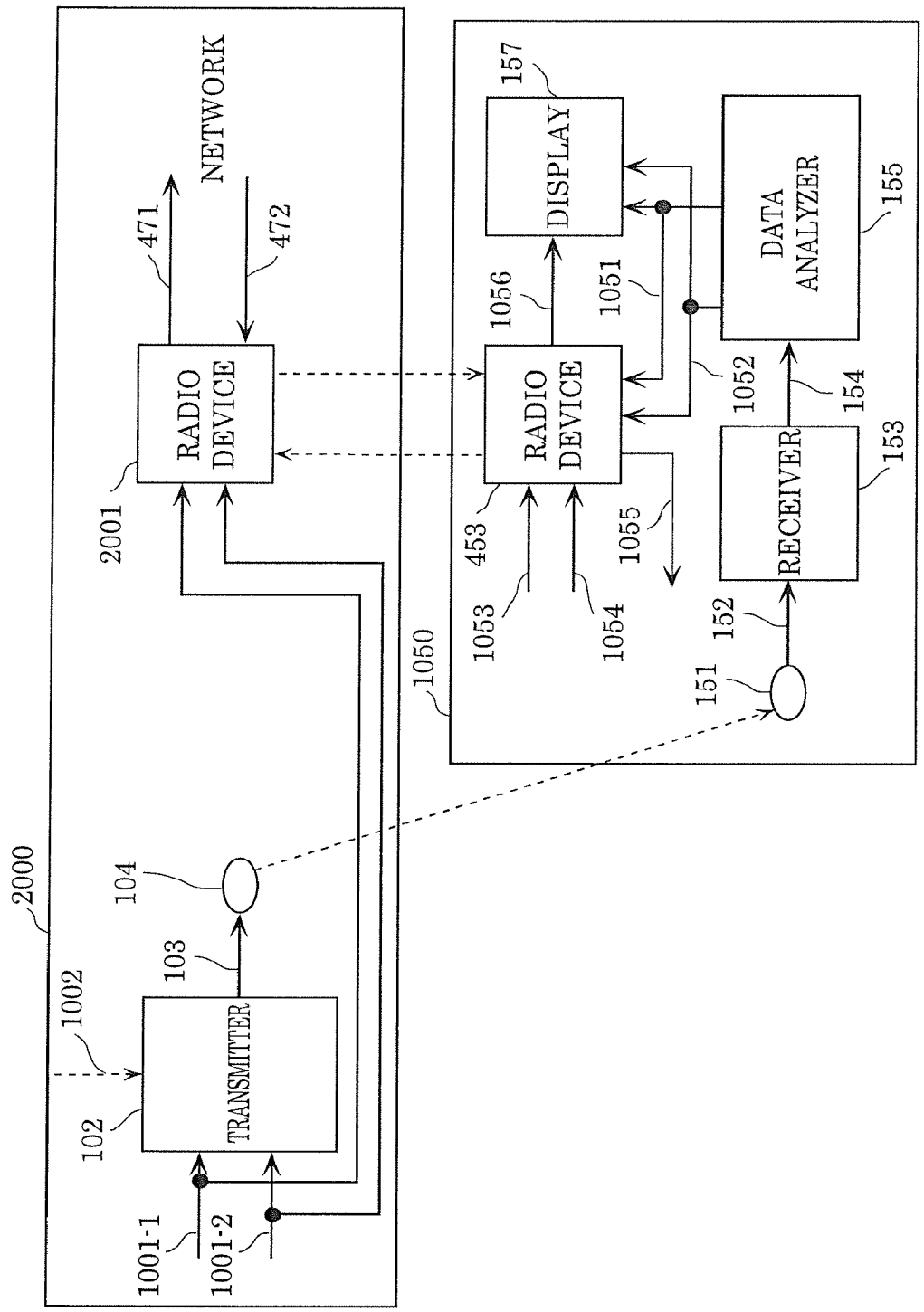
FIG. 20 illustrates one example of a configuration of a communication system according to Embodiment 6.

FIG. 20 illustrates one example of a configuration of a communication system according to this embodiment. The communication system illustrated in FIG. 20 includes, for example: an LED light source, lamp, light source, and/or light that emits visible light; base station 2000 including radio device 2001; and terminal 1050. Note that in FIG. 20, operations that are the same as in FIG. 1 and FIG. 10 share like reference marks.

Note that communication between radio device 2001 and radio device 453 in FIG. 20 is performed using, for example, radio waves.

Base station (or AP) 2000 in FIG. 20 includes, for example, an LED lamp, light source, and/or light that emits visible light. First, operations of one or more elements related to the LED lamp, light source, and/or light that emits visible light will be described.

Transmitter 102 receives inputs of information 1001-1 related to an SSID, information 1001-2 related to an encryption key, and data 1002, and based on these input signals, generates a (optical) modulated signal, and outputs modulated signal 103. For example, modulated signal 103 is transmitted from light source 104.

Next, information 1001-1 related to an SSID and information 1001-2 related to an encryption key will be described.

First, information 1001-1 related to an SSID will be described.

Information 1001-1 related to an SSID is information indicating the SSID of, for example, radio device 2001 that uses radio waves in base station (or AP) 2000 in FIG. 20. In other words, an "element related to the LED lamp, light source, and/or light that emits visible light" can provide access to radio device 2001, which is a secure access destination for the terminal. With this, terminal 1050 in FIG. 20 can achieve the advantageous effect of being able to securely obtain information from radio device 2001.

On the other hand, an element related to the LED lamp, light source, and/or light that emits visible light in base station 200 can restrict the terminals that access radio device 2001 to terminals in a space in which reception of the optical signal transmitted (emitted) by the element related to the LED lamp, light source, and/or light that emits visible light in base station 200 is possible. Note that when terminal 1050 receives an optical signal transmitted via a predetermined scheme, it may be determined that the notified SSID is the SSID of a secure base station, and, alternatively, processing for determining whether the SSID is secure or not may be performed. For example, an element related to the LED lamp, light source, and/or light that emits visible light in base station 2000 may transmit a predetermined identifier in an optical signal, and the terminal may determine whether the notified SSID is the SSID of a secure base station or not based on the received identifier.

Note that although FIG. 20 only illustrates base station (or AP) 2000, for example, when there is a base station (or AP) other than base station (or AP) 2000, terminal 1050 in FIG. 20 accesses base station (or AP) 2000 to obtain information.

Information 1001-2 related to an encryption key is information related to an encryption key required for terminal 1050 in FIG. 20 to establish communication with radio device 2001 in FIG. 20. Encrypted communication is possible between terminal 1050 in FIG. 20 and radio device 2001 as a result of terminal 1050 in FIG. 20 obtaining this information from an element related to the LED lamp, light source, and/or light that emits visible light. Terminal 1050 in FIG. 20 receives the modulated signal transmitted by an element related to the LED lamp, light source, and/or light that emits visible light in base station 200.

Note that in terminal 1050 in FIG. 20, components that operate the same as terminal 150 in FIG. 1 and terminal 1050 in FIG. 10 share like reference marks.

Light receiver 151 included in terminal 1050, examples of which include an image sensor such as a CMOS or organic CMOS image sensor, receives the modulated signal transmitted by an element related to the LED lamp, light source, and/or light that emits visible light in base station 200. Receiver 153 receives an input of reception signal 152 received by light receiver 151, performs processing such as demodulation and error correction decoding on the reception signal, and outputs reception data 154.

Data analyzer 155 receives an input of reception data 154, and outputs, based on the reception data, for example, information 1051 on the SSID of radio device 2001 in the base station to be connected to, and information 1052 on the encryption key for communication with radio device 2001 in the base station to be connected to. For example, in a wireless local area network (LAN), examples of encryption schemes include wired equivalent privacy (WEP), Wi-Fi protected access (WPA), and Wi-Fi protected access 2 (WPA2) (pre-shared key (PSK) mode, extended authentication protocol (EAP) mode). However, the encryption method is not limited to these examples.

Display 157 receives inputs of information 1051 on the SSID and information 1052 on the encryption key, and, for example, displays the SSID of the communication partner to be accessed by radio device 453 included in the terminal, and the encryption key (this display is referred to as a "first display" in this embodiment).

For example, after the first display, radio device 453 included in terminal 1050 in FIG. 20 receives inputs of information 1051 on the SSID and information 1052 on the encryption key, and establishes a connection with radio device 2001 in base station (or AP) 2000 (for example, the connection uses radio waves). Here, when radio device 2001 in base station (or AP) 2000 also communicates with radio device 453 in terminal 1050 in FIG. 20, radio device 2001 in base station (or AP) 2000 transmits a modulated signal using, for example, radio waves.

Thereafter, radio device 453 included in terminal 1050 in FIG. 20 receives inputs of data 1053 and control signal 1054, demodulates data 1053 in accordance with control signal 1054, and transmits a modulated signal as radio waves. Then, for example, radio device 2001 in base station (or AP) 2000 transmits data to the network (471) and receives data (472) from the network. Thereafter, for example, radio device 2001 in base station (or AP) 2000 transmits, to terminal 1050 in FIG. 20, a modulated signal as radio waves. Radio device 453 included in terminal 1050 in FIG. 20 performs processing such as demodulation and error correction decoding on the modulated signal received as radio waves to obtain reception data 1056. Display 157 displays a display based on reception data 1056.

FIG. 11 illustrates one example of a configuration of a frame of a modulated signal transmitted by transmitter 102 and light source 104 in base station (or AP) 2000 in FIG. 20. In FIG. 11, time is represented on the horizontal axis, and symbols that are the same as in FIG. 2 and FIG. 6 share like reference marks. Accordingly, repeated description thereof will be omitted.

Symbol 600-1 related to an SSID is a symbol for transmitting information 1001-1 related to an SSID in FIG. 20, and symbol 1101 related to an encryption key is a symbol for transmitting information 1001-2 related to an encryption key in FIG. 20. Data symbol 1102 is a symbol for transmitting data 1002.

Transmitter 102 and light source 104 in base station (or AP) 2000 transmit preamble 201, control information symbol 202, symbol 600-1 related to an SSID, symbol 1101 related to an encryption key, and data symbol 1102. Note that transmitter 102 and light source 104 in base station (or AP) 2000 in FIG. 20 may transmit a frame including symbols other than the symbols illustrated in FIG. 11. Moreover, the frame configuration, including the order in which the symbols are transmitted, is not limited to the configuration illustrated in FIG. 11.

FIG. 12 illustrates one example of a configuration of a frame of a modulated signal transmitted by radio device 453 included in terminal 1050 in FIG. 20. In FIG. 12, time is represented on the horizontal axis. As illustrated in FIG. 12, radio device 453 included in terminal 1050 in FIG. 20 transmits, for example, preamble 1201, and then transmits control information symbol 1202 and information symbol 1203.

Here, preamble 1201 is a symbol used for radio device 2001 in base station (or AP) 2000 that receives the modulated signal transmitted by radio device 453 in terminal 1050 in FIG. 20 to perform, for example, signal detection, temporal synchronization, frame synchronization, frequency synchronization, and frequency offset estimation.

Control information symbol 1202 includes data such as information related to the error correction encoding scheme method and/or demodulation scheme used in the generation of the modulated signal, information related to frame configuration, and information related to the transmission method used, and radio device 2001 in base station (or AP) 2000, for example, demodulates the modulated signal based on the information included in control information symbol 1202.

Information symbol 1203 is a symbol for radio device 453 included in terminal 1050 in FIG. 20 to transmit data.

Note that radio device 453 included in terminal 1050 in FIG. 20 may transmit a frame including symbols other than the symbols illustrated in FIG. 12 (for example, a frame including a pilot symbol (reference symbol) midway through the information symbol). Moreover, the frame configuration, including the order in which the symbols are transmitted, is not limited to the configuration illustrated in FIG. 12. In FIG. 12, a plurality of symbols may be present along the frequency axis, that is to say, symbols may be present on a plurality of frequencies (a plurality of carriers).

FIG. 7 illustrates one example of a configuration of a frame of a modulated signal transmitted by radio device 2001 in FIG. 20. In FIG. 7, time is represented on the horizontal axis. As illustrated in FIG. 7, base station 470 transmits, for example, preamble 701, and then transmits control information symbol 702 and information symbol 703.

Here, preamble 701 is a symbol for radio device 453 included in terminal 1050 in FIG. 20, which receives the modulated signal transmitted by radio device 2001 in FIG. 20, to perform, for example, signal detection, temporal synchronization, frame synchronization, frequency synchronization, and/or frequency offset estimation.

Control information symbol 702 includes data such as information related to the error correction encoding scheme method and/or demodulation scheme used in the generation of the modulated signal, information related to frame configuration, and information related to the transmission method used, and radio device 453 included in terminal 1050 in FIG. 20, for example, demodulates the modulated signal based on the information included in the control information symbol.

Information symbol 703 is a symbol for radio device 2001 in FIG. 20 to transmit data.

Note that radio device 2001 included in base station 2000 in FIG. 20 may transmit a frame including symbols other than the symbols illustrated in FIG. 7 (for example, a frame including a pilot symbol (reference symbol) midway through the information symbol). Moreover, the frame configuration, including the order in which the symbols are transmitted, is not limited to the configuration illustrated in FIG. 7. In FIG. 7, a plurality of symbols may be present along the frequency axis, that is to say, symbols may be present on a plurality of frequencies (a plurality of carriers).

Moreover, for example, a modulated signal that has the frame configuration illustrated in FIG. 11 and is transmitted by an element related to the LED lamp, light source, and/or light that emits visible light in base station 200 being transmitted at a regular timing, e.g., repeatedly transmitted is conceivable. This makes it possible for a plurality of terminals to implement the operations described above.

Figure 21:
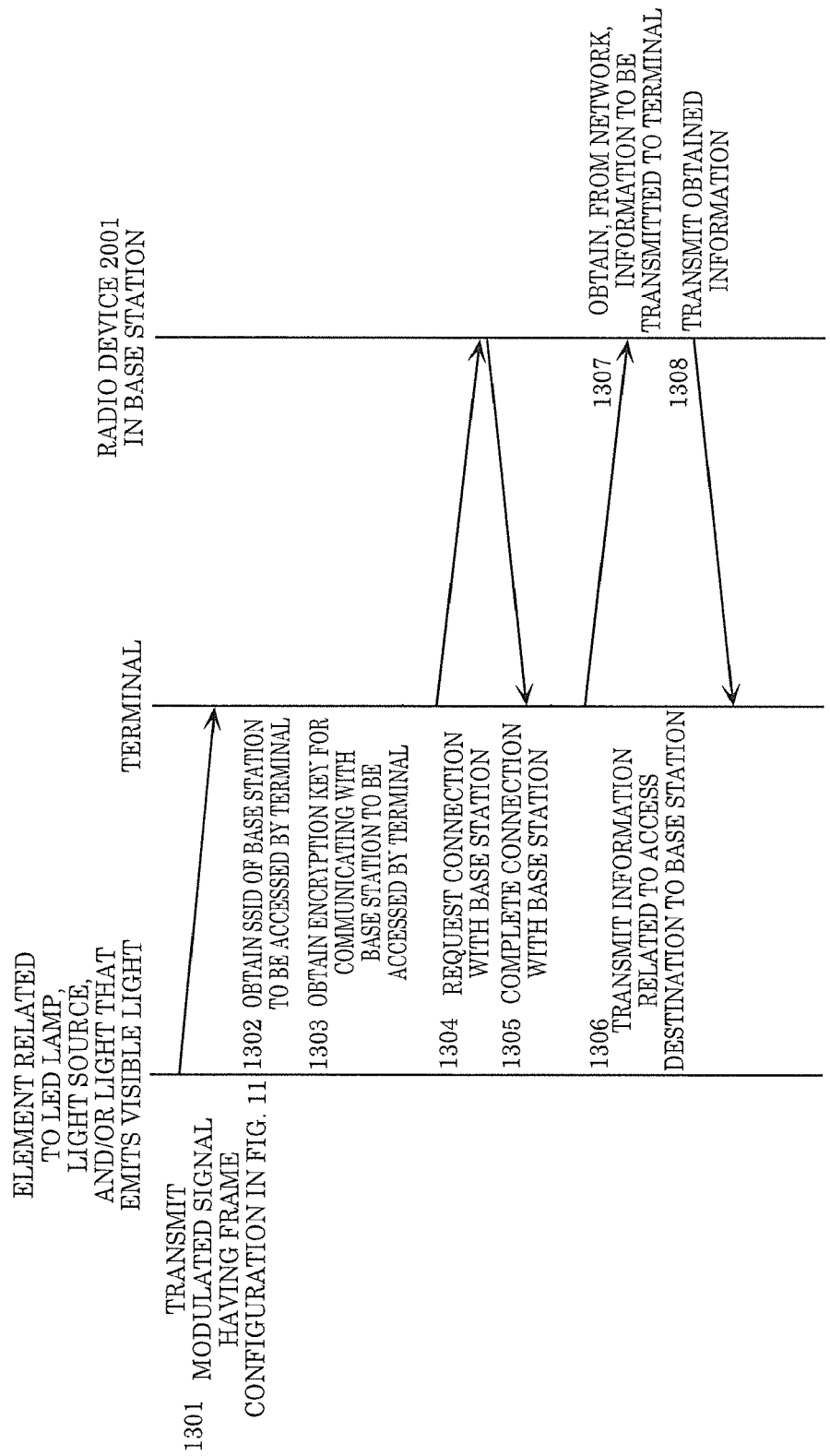
FIG. 21 is a flow chart of one example of processes performed by an element related to, for example, an LED, a terminal, and a radio device included in a base station according to Embodiment 6.

FIG. 21 is a flow chart illustrating one example of processes implemented by an element related to the LED lamp, light source, and/or light that emits visible light, terminal 1050, and radio device 2001 in the base station (or AP) in FIG. 20.

First, as 1301 in FIG. 21 illustrates, an element related to the LED lamp, light source, and/or light that emits visible light in FIG. 20 transmits a modulated signal having the frame configuration illustrated in FIG. 11.

Then, as 1302 in FIG. 21 illustrates, the modulated signal transmitted by an element related to the LED lamp, light source, and/or light that emits visible light in FIG. 20 is received, and terminal 1050 in FIG. 20 obtains the SSID of the base station to be accessed by terminal 1050.

Likewise, as 1303 in FIG. 21 illustrates, terminal 1050 in FIG. 20 obtains an encryption key to be used for communicating with base station 470 to be accessed by the terminal.

Terminal 1050 in FIG. 20 requests connection with radio device 2001 included in base station 2000 in FIG. 20 over radio waves (1304).

As 1305 in FIG. 21 illustrates, terminal 1050 in FIG. 20 completes the connection with radio device 2001 included in base station 2000 in FIG. 20 upon receiving a response from radio device 2001 included in base station 2000 in FIG. 20.

As 1306 in FIG. 21 illustrates, terminal 1050 in FIG. 20 transmits information on the connection destination to radio device 2001 included in base station 2000 in FIG. 20 using radio waves.

Then, as 1307 in FIG. 21 illustrates, radio device 2001 included in base station 2000 in FIG. 20 obtains information to be transmitted to terminal 1050 in FIG. 20 from the network.

As 1308 in FIG. 21 illustrates, radio device 2001 included in base station 2000 in FIG. 20 transmits the obtained information to terminal 1050 in FIG. 20 using radio waves, and terminal 1050 in FIG. 20 obtains the information.

For example, when necessary, terminal 1050 in FIG. 20 obtains required information from the network via radio device 2001 included in base station 2000 in FIG. 20.

As described above, based on the SSID information and the encryption key information transmitted from an element related to the LED lamp, light source, and/or light that emits visible light in the base station, the terminal connects to the base station (or AP) and obtains information, whereby an advantageous effect that it is possible to securely obtain information via the base station (or AP) whose security has been authenticated can be achieved. This is because, when information from a visible light modulated signal is obtained, since it is visible light, the user can easily determine whether the source of information is secure or not.

For example, when an SSID is obtained from a modulated signal transmitted by a wireless LAN over radio waves, it is difficult for the user to determine which device transmitted the radio waves. Accordingly, from the viewpoint of ensuring information security, obtaining the SSID via visible light communication is more suitable.

Note that in this embodiment, an element related to the LED lamp, light source, and/or light that emits visible light in the base station is exemplified as transmitting encryption key information, but, for example, when the base station (or AP) does not perform encrypted communication using an encryption key, the element related to the LED lamp, light source, and/or light that emits visible light in the base station can transmit only the information related to an SSID without transmitting the encryption key information, that is, the element related to the LED lamp, light source, and/or light that emits visible light in the base station may be implemented without the configuration related to an encryption key.

As illustrated in FIG. 20, the SSID and encryption key for radio device 2001 included in base station 2000 may be overwritten. For example, in FIG. 20, information 1001-1 related to an SSID and information 1001-2 related to an encryption key are received as inputs by radio device 2001. Radio device 2001 included in base station 2000 overwrites the SSID and encryption key as per the input information 1001-1 related to an SSID and information 1001-2 related to an encryption key. With this, the security of the communication between the terminal and radio device 2001 included in base station 2000 is assured (however, in FIG. 20, although radio device 2001 included in base station 2000 has a function of being able to overwrite the SSID and encryption key, radio device 2001 included in base station 2000 may have a configuration in which this function is not included).

Moreover, the configuration of an element related to the LED lamp, light source, and/or light that emits visible light in the base station is not limited to the configuration illustrated in FIG. 20, the configuration of the terminal is not limited to the configuration illustrated in FIG. 20, and the configuration of the connection destination of the radio device included in the base station is not limited to the configuration illustrated in FIG. 20.

In this embodiment, although only one base station (or AP) is exemplified in the configuration illustrated in FIG. 20, a plurality of (secure) base stations (or APs) accessible by the terminal may be included (note that the radio devices in these base stations transmit and receive modulated signals using radio waves). Here, the symbol related to an SSID transmitted by an element related to the LED lamp, light source, and/or light that emits visible light in FIG. 20 may include information indicating the SSIDs of the plurality of radio devices in the base stations (or APs). Moreover, the symbol related to an encryption key transmitted by an element related to the LED lamp, light source, and/or light that emits visible light in FIG. 20 may include encryption key information used to connect to the plurality of radio devices in the base stations (or APs). Terminal 1050 in FIG. 20 may select a radio device in a base station (or AP) to wirelessly connect to (for example, over radio waves), based on the information on the SSIDs and encryption key information of the radio stations in the base stations (or connect to the plurality of radio devices in the plurality of base stations (or APs)).

For example, assume there are three base stations (or APs) that include radio devices. The radio devices are named radio device #A, radio device #B, and radio device #C. The SSID of radio device #A is "abcdef", the SSID of radio device #B is "ghijk", and the SSID of radio device #C is "pqrstu", the encryption key for connecting with radio device #A is "123", the encryption key for connecting with radio device #B is "456", and the encryption key for connecting with radio device #C is "789".

In such cases, symbol 600-1 related to an SSID in the frame configuration illustrated in FIG. 11 of the modulated signal transmitted by an element related to the LED lamp, light source, and/or light that emits visible light in base station 200 includes information related to the SSID "abcdef" of radio device #A, the SSID "ghijk" of radio device #B, and the SSID "pqrstu" of radio device #C. The symbol 1101 related to an encryption key having the frame configuration illustrated in FIG. 11 includes information related to the encryption key "123" for connecting with radio device #A, the encryption key "456" for connecting with radio device #B, and the encryption key "789" for connecting with radio device #C.

Terminal 1050 in FIG. 20 receives symbol 600-1 related to an SSID and thus obtains the SSID "abcdef" of radio device #A, the SSID "ghijk" of radio device #B, and the SSID "pqrstu" of radio device #C, receives symbol 1101 related to an encryption key and thus obtains the encryption key "123" for connecting with radio device #A, the encryption key "456" for connecting with radio device #B, and the encryption key "789" for connecting with radio device #C. Then, based on this information, terminal 1050 in FIG. 20 selects a base station (or AP) to wirelessly connect to (for example, via radio waves), and connects to the selected base station (or AP).

As described in this embodiment, as a result of the terminal setting a radio device included in a base station to access using a light source, exemplified here as an LED light source, a mode for making a special setting for processes for establishing a wireless connection between the terminal and base station in the modulated signal for connection over radio waves that is transmitted by the terminal is not required, and a mode for making a special setting for processes for establishing a wireless connection between the terminal and base station in the modulated signal for connection over radio waves that is transmitted by the base station is not required, whereby an advantageous effect that wireless communication data transmission efficiency improves can be achieved.

As described above, the encryption key may be an encryption key for an SSID on a wireless LAN, may be an encryption key for restricting the form of connection used, the form of service used, and/or the connectivity range of the network (in other words, any encryption key that is restrictive is sufficient).

Embodiment 7 (Plural Base Stations; Access Control Performed)

Figure 22:
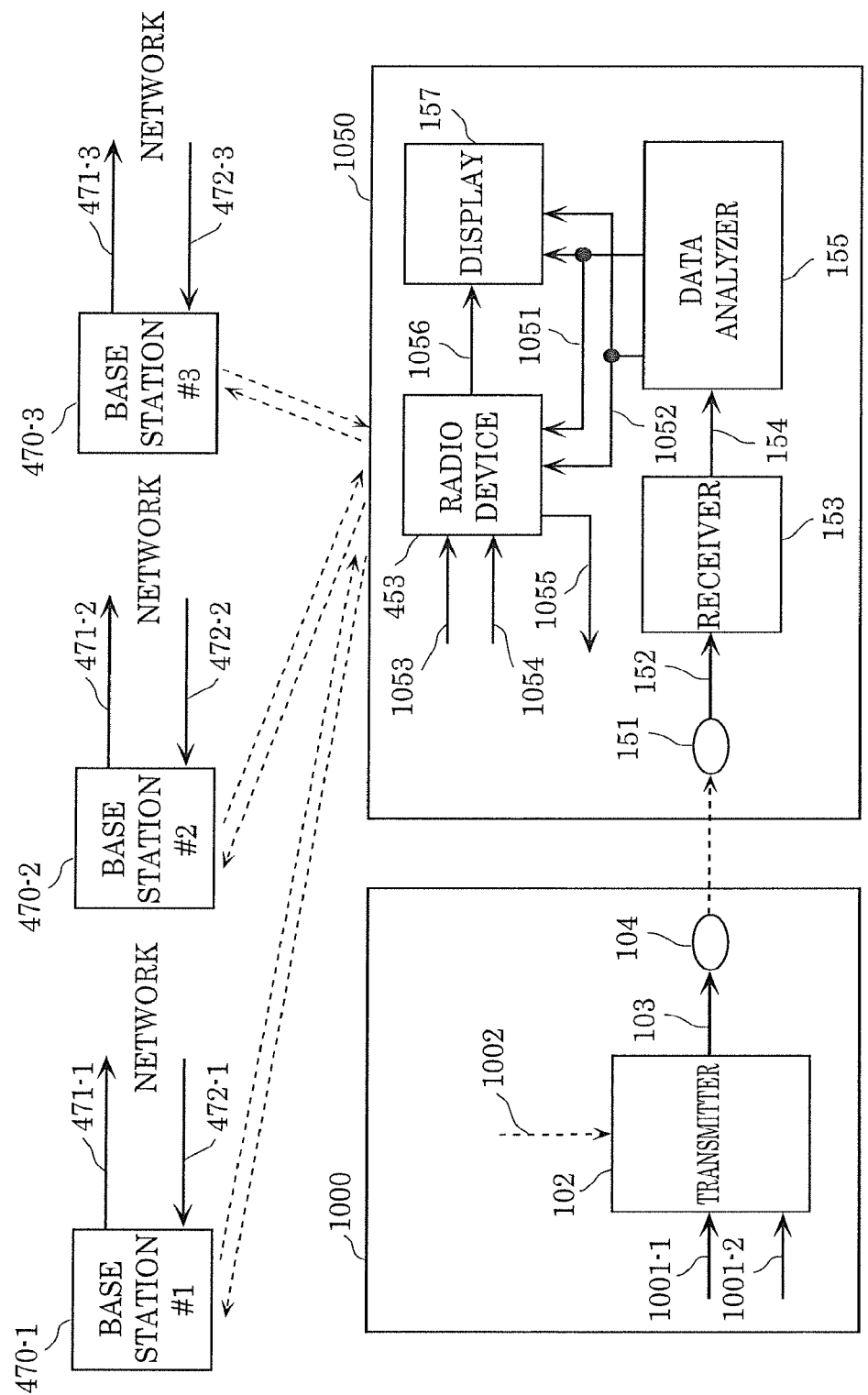
FIG. 22 illustrates one example of a configuration of a communication system according to Embodiment 7.

FIG. 22 illustrates one example of a configuration of a communication system according to this embodiment. The communication system illustrated in FIG. 22 includes, for example: device 1000 including an LED light source, lamp, light source, and/or light that emits visible light; terminal 1050; and, for example, base station #1 470-1, base station #2 470-2, and base station #3 470-3 that communicate with terminal 1050. Note that in FIG. 22, operations that are the same as in FIG. 1, FIG. 4, and FIG. 10 share like reference marks.

Device 1000 in FIG. 22 includes, for example, an LED lamp, light source, and/or light that emits visible light. Note that device 1000 is referred to as a "fifth device" in this embodiment. Note that communication between radio device radio device 453 and base station #1 470-1, between radio device 453 and base station #2 470-2, and between radio device 453 and base station #3 470-3 in FIG. 22 is performed using, for example, radio waves.

In fifth device 1000 in FIG. 22, transmitter 102 receives inputs of information 1001-1 related to an SSID, information 1001-2 related to an encryption key, and data 1002, and based on these input signals, generates a (optical) modulated signal, and outputs modulated signal 103. For example, modulated signal 103 is transmitted from light source 104.

Next, information 1001-1 related to an SSID and information 1001-2 related to an encryption key will be described.

First, information 1001-1 related to an SSID will be described.

For example, information 1001-1 related to an SSID is information indicating the SSID of base station (or AP) 470-1 in FIG. 22, the SSID of base station (or AP) 470-2 in FIG. 22, and the SSID of base station (or AP) 470-3 in FIG. 22. Note that, in this example, base stations (or APs) 470-1, 470-2, and 470-3 transmit modulated signals over radio waves, and receive radio wave modulated signals. In other words, fifth device 1000 can provide access to base stations 470-1, 470-2, and 470-3, which are secure access destinations for the terminal. With this, terminal 1050 in FIG. 22 can achieve the advantageous effect of being able to securely obtain information from base stations (or APs) 470-1, 470-2, and 470-3.

On the other hand, device 1000 can restrict the terminals that access base stations 470-1, 470-2, and 470-3 to terminals in a space in which it is possible to receive optical signals transmitted (emitted) by device 1000. Note that when terminal 1050 receives an optical signal transmitted via a predetermined scheme, it may be determined that the notified SSID is the SSID of a secure base station, and, alternatively, processing for determining whether the SSID is secure or not may be performed. For example, device 1000 may transmit a predetermined identifier in an optical signal, and the terminal may determine whether the notified SSID is the SSID of a secure base station or not based on the received identifier.

Note that the configuration in FIG. 22 illustrates base stations (or AP) 470-1, 470-2, and 470-3, but one or more base stations (or APs) other than base stations (or AP) 470-1, 470-2, and 470-3 may also be included.

Information 1001-2 related to an encryption key is information related to an encryption key required for terminal 1050 in FIG. 22 to establish communication with base stations (or AP) 470-1, 470-2, and 470-3 in FIG. 22. Encrypted communication is possible between the terminal and base station (or AP) 470-1, between the terminal and base station (or AP) 470-2, and between the terminal and base station (or AP) 470-3 as a result of terminal 1050 in FIG. 22 obtaining this information from fifth device 1000 in FIG. 22.

Terminal 1050 in FIG. 22 receives the modulated signal transmitted by fifth device 1000. Note that in terminal 1050 in FIG. 22, components that operate the same as terminal 150 in FIG. 1 and terminal 450 in FIG. 4 share like reference marks.

Light receiver 151 included in terminal 1050, examples of which include an image sensor such as a CMOS or organic CMOS image sensor, receives the modulated signal transmitted by fifth device 1000. Receiver 153 receives an input of reception signal 152 received by light receiver 151, performs processing such as demodulation and error correction decoding on the reception signal, and outputs reception data 154.

Data analyzer 155 receives an input of reception data 154, and outputs, based on the reception data, for example, information 1051 on the SSIDs of the base stations (470-1, 470-2, and 470-3) to be connected to, and information 1052 on the encryption keys for communication with the base stations (470-1, 470-2, and 470-3) to be connected to. For example, in a wireless local area network (LAN), examples of encryption schemes include wired equivalent privacy (WEP), Wi-Fi protected access (WPA), and Wi-Fi protected access 2 (WPA2) (pre-shared key (PSK) mode, extended authentication protocol (EAP) mode). However, the encryption method is not limited to these examples.

Display 157 receives inputs of information 1051 on the SSID and information 1052 on the encryption key, and, for example, displays the SSID of the communication partner to be accessed by radio device 453 included in the terminal, and the encryption key (this display is referred to as a "first display" in this embodiment).

For example, after the first display, radio device 453 included in terminal 1050 in FIG. 22 receives inputs of information 1051 on the SSID and information 1052 on the encryption key, and establishes a connection with any one of base stations (or APs) 470-1, 470-2, and 470-3 (for example, the connection uses radio waves). Here, when the base station also communicates with radio device 453 in terminal 1050 in FIG. 22, the base station transmits a modulated signal using, for example, radio waves.

Thereafter, radio device 453 included in terminal 1050 in FIG. 22 receives inputs of data 1053 and control signal 1054, demodulates data 1053 in accordance with control signal 1054, and transmits a modulated signal as radio waves.

Then, for example, the base station (or AP) connected to transmits data to the network (any one of 471-1, 471-2, and 471-3) and receives data (any one of 472-1, 472-2, and 472-3) from the network. Thereafter, for example, the base station connected to transmits, to terminal 1050 in FIG. 22, a modulated signal as radio waves.

Radio device 453 included in terminal 1050 in FIG. 22 performs processing such as demodulation and error correction decoding on the modulated signal received as radio waves to obtain reception data 1056. Display 157 displays a display based on reception data 1056.

Figure 23:
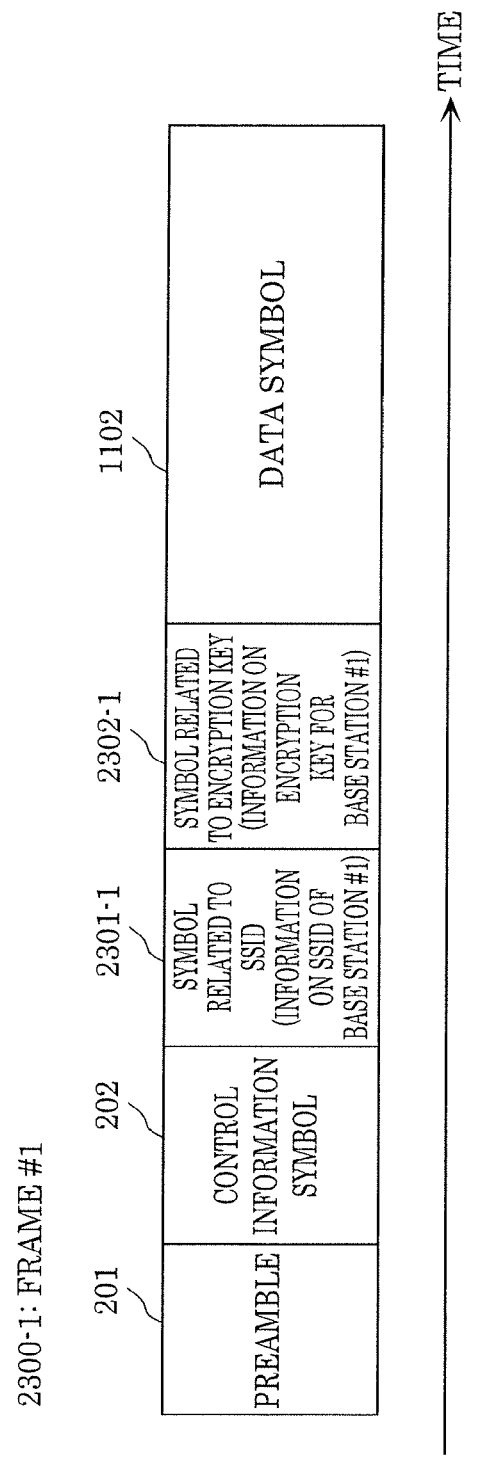
FIG. 23 illustrates one example of a frame configuration of a modulated signal transmitted by a device according to Embodiment 7.
Figure 24:
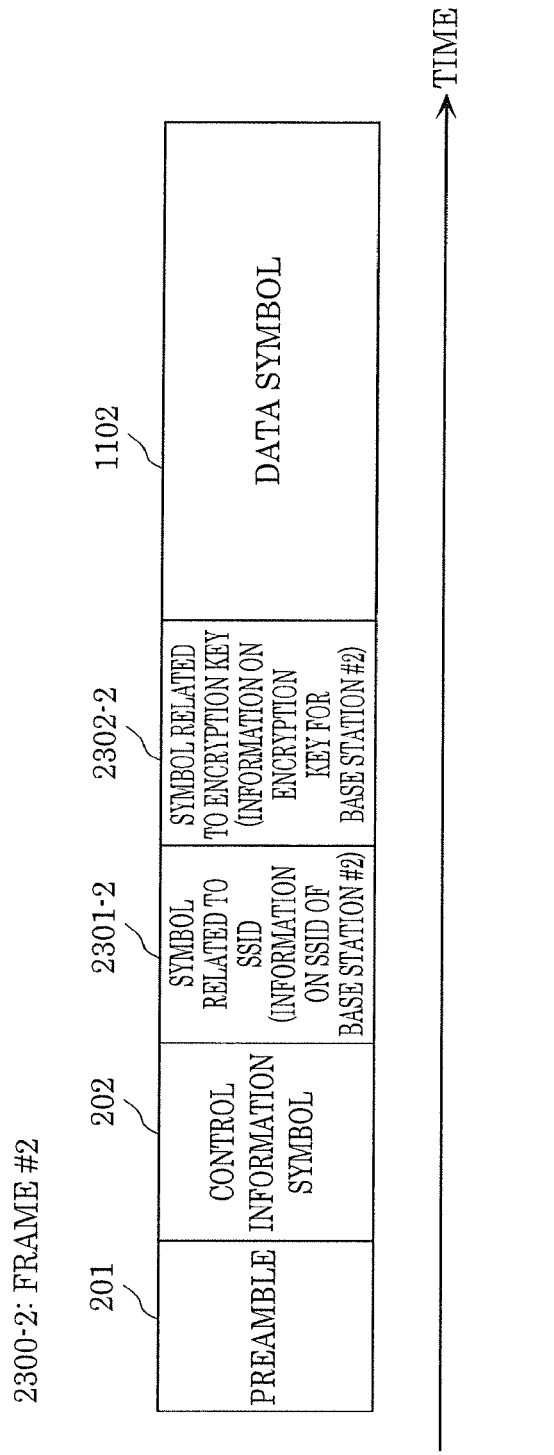
FIG. 24 illustrates one example of another frame configuration of a modulated signal transmitted by a device according to Embodiment 7.
Figure 25:
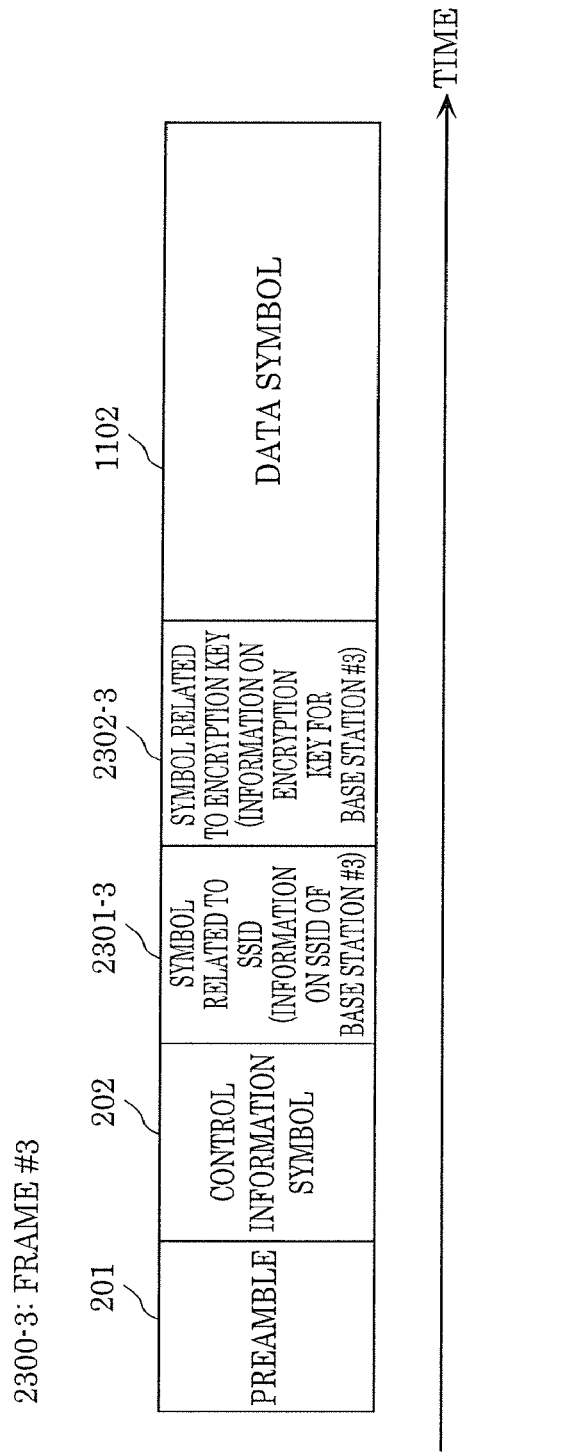
FIG. 25 illustrates one example of another frame configuration of a modulated signal transmitted by a device according to Embodiment 7.

Assume, in the case of FIG. 22, there are three types of frame configurations as modulated signals transmitted by fifth device 1000 in FIG. 22. FIG. 23 illustrates frame #1 2300-1, which is one of the three types of frame configurations, FIG. 24 illustrates frame configuration #2 2300-2, which is one of the three types of frame configurations, and FIG. 25 illustrates frame configuration #3 2300-3, which is one of the three types of frame configurations.

FIG. 23 illustrates one example of the configuration of frame #1 2300-1 of a modulated signal transmitted by fifth device 1000 in FIG. 22. In FIG. 23, time is represented on the horizontal axis, and symbols that are the same as in FIG. 2 and FIG. 11 share like reference marks. Accordingly, repeated description thereof will be omitted. Frame #1 2300-1 in FIG. 23 is a frame for transmitting information on the SSID of base station #1 470-1 in FIG. 22 and an encryption key for base station #1 470-1 (an encryption key for accessing base station #1 470-1) in FIG. 22.

Symbol 2301-1 related to an SSID in FIG. 23 is a symbol for transmitting information 1001-1 related to an SSID in FIG. 22. Moreover, symbol 2301-1 related to an SSID in FIG. 23 is a symbol for fifth device 1000 in FIG. 22 to transmit the SSID of base station #1 470-1 in FIG. 22.

Symbol 2302-1 related to an encryption key in FIG. 23 is a symbol for transmitting information 1001-2 related to an encryption key in FIG. 22. Moreover, symbol 2302-1 related to an encryption key in FIG. 23 is a symbol for fifth device 1000 in FIG. 22 to transmit an encryption key for base station #1 470-1 (an encryption key for accessing base station #1 470-1) in FIG. 22.

Fifth device 1000 transmits preamble 201, control information symbol 202, symbol 2301-1 related to an SSID, symbol 2302-1 related to an encryption key, and data symbol 1102. Note that fifth device 1000 in FIG. 22 may transmit frame #1 2300-1 including symbols other than the symbols illustrated in FIG. 23. Moreover, the configuration of frame #1 2300-1, including the order in which the symbols are transmitted, is not limited to the configuration illustrated in FIG. 23.

FIG. 24 illustrates one example of the configuration of frame #2 2300-2 of a modulated signal transmitted by fifth device 1000 in FIG. 22. In FIG. 24, time is represented on the horizontal axis, and symbols that are the same as in FIG. 2 and FIG. 11 share like reference marks. Accordingly, repeated description thereof will be omitted. Frame #2 2300-2 in FIG. 24 is a frame for transmitting information on the SSID of base station #2 470-2 in FIG. 22 and an encryption key for base station #2 470-2 (an encryption key for accessing base station #2 470-2) in FIG. 22.

Symbol 2301-2 related to an SSID in FIG. 24 is a symbol for transmitting information 1001-1 related to an SSID in FIG. 22. Moreover, symbol 2301-2 related to an SSID in FIG. 24 is a symbol for fifth device 1000 in FIG. 22 to transmit the SSID of base station #2 470-2 in FIG. 22.

Symbol 2302-2 related to an encryption key in FIG. 24 is a symbol for transmitting information 1001-2 related to an encryption key in FIG. 22. Moreover, symbol 2302-2 related to an encryption key in FIG. 24 is a symbol for fifth device 1000 in FIG. 22 to transmit an encryption key for base station #2 470-2 (an encryption key for accessing base station #2 470-2) in FIG. 22.

Fifth device 1000 transmits preamble 201, control information symbol 202, symbol 2301-2 related to an SSID, symbol 2302-2 related to an encryption key, and data symbol 1102. Note that fifth device 1000 in FIG. 22 may transmit frame #2 2300-2 including symbols other than the symbols illustrated in FIG. 24. Moreover, the configuration of frame #2 2300-2, including the order in which the symbols are transmitted, is not limited to the configuration illustrated in FIG. 24.

FIG. 25 illustrates one example of the configuration of frame #3 2300-3 of a modulated signal transmitted by fifth device 1000 in FIG. 22. In FIG. 25, time is represented on the horizontal axis, and symbols that are the same as in FIG. 2 and FIG. 11 share like reference marks. Accordingly, repeated description thereof will be omitted. Frame #3 2300-3 in FIG. 25 is a frame for transmitting information on the SSID of base station #3 470-3 in FIG. 22 and an encryption key for base station #3 470-3 (an encryption key for accessing base station #3 470-3) in FIG. 22.

FIG. 25 illustrates one example of the configuration of frame #3 2300-3 of a modulated signal transmitted by fifth device 1000 in FIG. 22. In FIG. 25, time is represented on the horizontal axis, and symbols that are the same as in FIG. 2 and FIG. 11 share like reference marks. Accordingly, repeated description thereof will be omitted. Frame #3 2300-3 in FIG. 25 is a frame for transmitting information on the SSID of base station #3 470-3 in FIG. 22 and an encryption key for base station #3 470-3 (an encryption key for accessing base station #3 470-3) in FIG. 22.

Symbol 2301-3 related to an SSID in FIG. 25 is a symbol for transmitting information 1001-1 related to an SSID in FIG. 22. Moreover, symbol 2301-3 related to an SSID in FIG. 25 is a symbol for fifth device 1000 in FIG. 22 to transmit the SSID of base station #3 470-3 in FIG. 22.

Symbol 2302-3 related to an encryption key in FIG. 25 is a symbol for transmitting information 1001-2 related to an encryption key in FIG. 22. Moreover, symbol 2302-3 related to an encryption key in FIG. 25 is a symbol for fifth device 1000 in FIG. 22 to transmit an encryption key for base station #3 470-3 (an encryption key for accessing base station #3 470-3) in FIG. 22.

Fifth device 1000 transmits preamble 201, control information symbol 202, symbol 2301-3 related to an SSID, symbol 2302-3 related to an encryption key, and data symbol 1102. Note that fifth device 1000 in FIG. 22 may transmit frame #3 2300-3 including symbols other than the symbols illustrated in FIG. 25. Moreover, the configuration of frame #3 2300-3, including the order in which the symbols are transmitted, is not limited to the configuration illustrated in FIG. 25.

Figure 26:
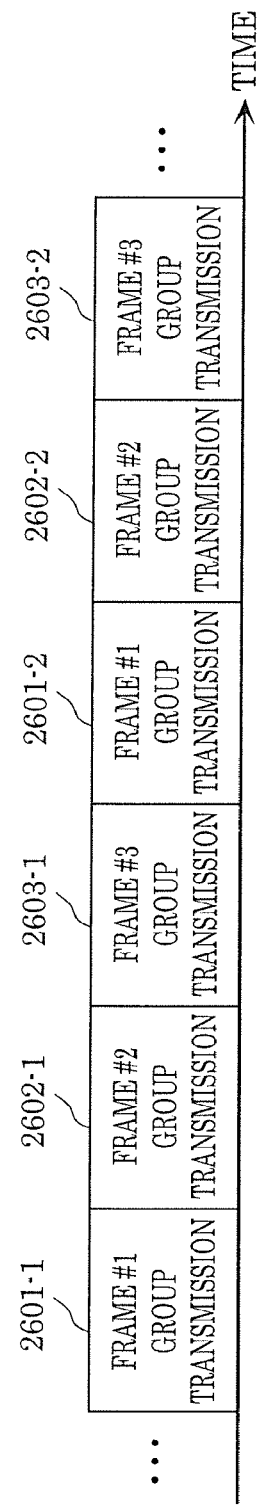
FIG. 26 illustrates one example of transmission method using a device according to Embodiment 7.

FIG. 26 illustrates an example of a transmission method used by fifth device 1000 in FIG. 22 upon transmitting frame #1 2300-1 in FIG. 23, frame #2 2300-2 in FIG. 24, and frame #3 2300-3 in FIG. 25. In FIG. 26, time is represented on the horizontal axis.

In FIG. 26, in the frame #1 group transmissions of 2601-1 and 2601-2, one or more of frames #1 2300-1 illustrated in FIG. 23 are transmitted. In the frame #2 group transmissions of 2602-1 and 2602-2, one or more of frames #2 2300-2 in FIG. 24 are transmitted. In the frame #3 group transmissions of 2603-1 and 2603-2, one or more of frames #3 2300-3 in FIG. 25 are transmitted.

This will be described in more detail next.

The recitation "in the frame #1 group transmissions of 2601-1 and 2601-2, one or more of frames #1 2300-1 illustrated in FIG. 23 are transmitted" above will be described.

For example, when an image sensor, such as a CMOS or organic CMOS image sensor is used in light receiver 151, it is possible to process the reception signal in units of frames in moving or still images. Note that, for example, when a moving picture is labeled as "4K 30p", the number of pixels of one frame is 3840×2160, and the moving picture includes 30 frames per second.

Accordingly, when fifth device 1000 in FIG. 22 transmits a modulated signal including frame #1 2300-1 in FIG. 23, frame #2 2300-2 in FIG. 24, and frame #3 2300-3 in FIG. 25 in a single frame, terminal 1050 in FIG. 22 has difficulty in selecting a base station to access from among the plurality of base stations.

In view of this, a frame configuration such as illustrated in FIG. 26 is proposed.

Method 1-1:

Method 1-1 makes the temporal space that frame #1 group transmission occupies longer than a frame of a still or moving picture by including a plurality of frames #1 2300-1 illustrated in FIG. 23, in frame #1 group transmissions of 2601-1 and 2601-2.

This method makes it possible for terminal 1050 in FIG. 22 to easily select a base station to access from among the plurality of base stations since terminal 1050 in FIG. 22 can prevent the reception of a modulated signal including, in a single frame of a still or moving picture, frame #1 2300-1 in FIG. 23, frame #2 2300-2 in FIG. 24, and frame #3 2300-3 in FIG. 25, by fifth device 1000.

Method 2-1:

Method 2-1 makes the temporal space that frame #1 2300-1 in FIG. 23 occupies longer than a frame of a still or moving picture. For example, symbol 2301-1 related to an SSID in FIG. 23 may include a plurality of items of the information on the SSID for base station #1 (the information on the SSID for base station #1 is repeatedly included), or symbol 2302-1 related to an encryption key may include a plurality of items of the information on the encryption key for base station #1 (the encryption key for connecting with base station #1) (the information on the encryption key for base station #1 (the encryption key for connecting with base station #1) is repeatedly included).

This method makes it possible for terminal 1050 in FIG. 22 to easily select a base station to access from among the plurality of base stations since terminal 1050 in FIG. 22 can prevent the reception of a modulated signal including, in a single frame of a still or moving picture, frame #1 2300-1 in FIG. 23, frame #2 2300-2 in FIG. 24, and frame #3 2300-3 in FIG. 25, by fifth device 1000.

Similarly, frame #2 group transmissions of 2602-1 and 2602-2 may have the following configurations.

Method 1-2:

Method 1-2 makes the temporal space that frame #2 group transmission occupies longer than a frame of a still or moving picture by including a plurality of frames #2 2300-2 illustrated in FIG. 24, in frame #2 group transmissions of 2602-1 and 2602-2.

Method 2-2:

Method 2-2 makes the temporal space that frame #2 2300-2 in FIG. 24 occupies longer than a frame of a still or moving picture. For example, symbol 2301-2 related to an SSID in FIG. 24 may include a plurality of items of the information on the SSID for base station #2 (the information on the SSID for base station #2 is repeatedly included), or symbol 2302-2 related to an encryption key may include a plurality of items of the information on the encryption key for base station #2 (the encryption key for connecting with base station #2) (the information on the encryption key for base station #2 (the encryption key for connecting with base station #2) is repeatedly included).

Similarly, frame #3 group transmissions of 2603-1 and 2603-2 may have the following configurations.

Method 1-3:

Method 1-3 makes the temporal space that frame #3 group transmission occupies longer than a frame of a still or moving picture by including a plurality of frames #3 2300-3 illustrated in FIG. 25, in frame #3 group transmissions of 2603-1 and 2603-2.

Method 2-3:

Method 2-3 makes the temporal space that frame #3 2300-3 in FIG. 25 occupies longer than a frame of a still or moving picture. For example, symbol 2301-3 related to an SSID in FIG. 25 may include a plurality of items of the information on the SSID for base station #3 (the information on the SSID for base station #3 is repeatedly included), or symbol 2302-3 related to an encryption key may include a plurality of items of the information on the encryption key for base station #3 (the encryption key for connecting with base station #3) (the information on the encryption key for base station #3 (the encryption key for connecting with base station #3) is repeatedly included).

Next, the advantageous effects achieved when fifth device 1000 in FIG. 22 transmits a frame, such as those illustrated in FIG. 23 through FIG. 26, will be described.

Figure 27:
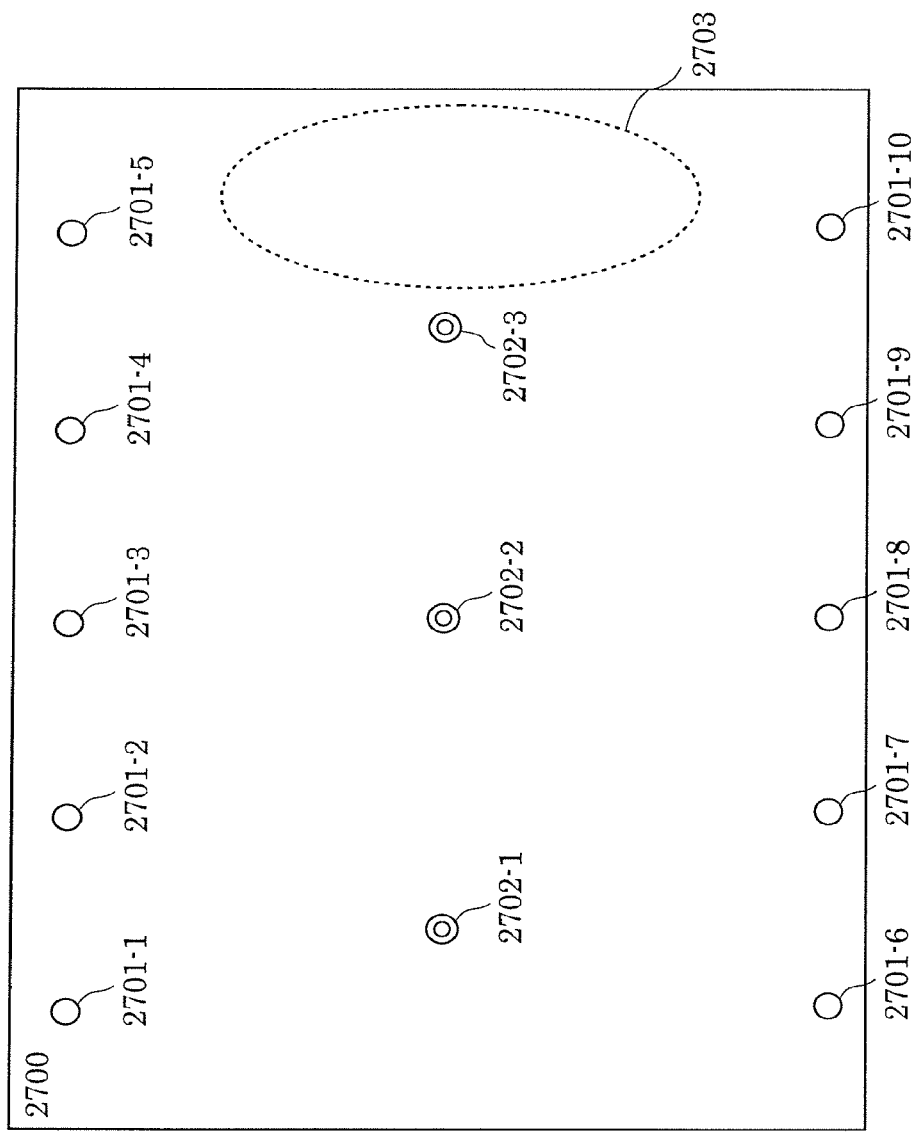
FIG. 27 illustrates one example of an area in which devices and base stations are disposed according to Embodiment 7.

Consider area 2700 in FIG. 27. Fifth devices 1000 having the configuration illustrated in FIG. 22 are disposed at circles 2701-1, 2701-2, 2701-3, 2701-4, 2701-5, 2701-6, 2701-7, 2701-8, 2701-8, 2701-9, and 2701-10. Base station #1 470-1 in FIG. 22 is disposed at double circle 2702-1, base station #2 470-2 in FIG. 22 is disposed at double circle 2702-2, and base station #3 470-3 in FIG. 22 is disposed at double circle 2702-3.

For example, 99 terminals having the configuration of 1050 in FIG. 22 are present in the area indicated as 2703.

Here, for example, fifth devices 2701-5 and 2701-10 both transmit information on the SSID of base station #3 470-3 and information on the encryption key for access to base station #3 470-3 (since the base station closest to fifth devices 2701-5 and 2701-10 is base station #3 470-3).

In such cases, all of the 99 terminals having the configuration of 1050 in FIG. 22 will access base station #3 470-3 in FIG. 22. This means there is a high probability that the terminals having the configuration of 1050 in FIG. 22 will have difficulty accessing base station #3 470-3 in FIG. 22.

Taking this point into consideration, by making it so that the 99 terminals having the configuration of 1050 in FIG. 22 access base station #1 470-1 (2702-1) in FIG. 22, base station #2 470-2 (2702-2) in FIG. 22, and base station #3 470-3 (2702-3) in FIG. 22 as evenly as possible, it is possible to achieve the advantageous effect of a reduction in terminals having difficulty accessing a base station, as described above.

In this embodiment, when fifth device 1000 in FIG. 22 transmits a frame, such as those illustrated in FIG. 23 through FIG. 26, the 99 terminals having the configuration of 1050 in FIG. 22 typically access fifth device 1000 in FIG. 22 at different timings, so the 99 terminals having the configuration of 1050 in FIG. 22 access base station #1 470-1 (2702-1) in FIG. 22, base station #2 470-2 (2702-2) in FIG. 22, and base station #3 470-3 (2702-3) in FIG. 22 as evenly as possible. Accordingly, the previously-described advantageous effect of a reduction in terminals having difficulty accessing a base station can be achieved. In other words, it is possible to achieve an advantageous effect that concentration of access from a plurality of terminals to any given base station can be avoided.

Note that although FIG. 26 illustrates an example of a transmission method used upon fifth device 1000 in FIG. 22 transmitting frame #1 2300-1 in FIG. 23, frame #2 2300-2 in FIG. 24, and frame #3 2300-3 in FIG. 25, the transmission method used upon fifth device 1000 in FIG. 22 transmitting frame #1 2300-1 in FIG. 23, frame #2 2300-2 in FIG. 24, and frame #3 2300-3 in FIG. 25 is not limited to this example.

For example, in FIG. 26, the order of frame #1 group transmission, frame #2 group transmission, and frame #3 group transmission is repeated, but the order in which frame #1 group transmission, frame #2 group transmission, and frame #3 group transmission are transmitted is not limited to the example given in FIG. 26. For example, the transmission of frame group #1, the transmission of frame group #2, and the transmission of frame group #3 may be temporally randomized, and, alternatively, the order of the transmission of frame group #1, the transmission of frame group #2, and the transmission of frame group #3 may be a regular order different than the example given in FIG. 26. It is sufficient so long as fifth device 1000 in FIG. 22 transmits frame #1 group, frame #2 group, and frame #3 group. For example, when fifth device 1000 temporally randomizes the transmission of frame group #1, the transmission of frame group #2, and the transmission of frame group #3, a random number may be generated at a given timing, and the frame group specified by that random number may be transmitted at that time. Note that the usage of a random number is merely one non-limiting example.

Moreover, in FIG. 26, frame #1 group transmission, frame #2 group transmission, and frame #3 group transmission are exemplified as being performed consecutively, but these transmissions do not necessarily need to be performed consecutively. For example, in FIG. 26, there may be a time interval between frame #1 group transmission 2601-1 and frame #2 group transmission 2602-2.

In FIG. 26, the example includes only frame #1 group transmission, frame #2 group transmission, and frame #3 group transmission, but other symbols and/or frames may be included. Furthermore, in FIG. 26 and FIG. 22, there are three base stations, but the number of base stations is not limited to this example. As long as there are two or more base stations, they can operate the same as when there are three. Accordingly, for example, when there are N base stations (N is an integer of 2 or more), when transmission such as that illustrated in FIG. 26 is performed, frame #k group transmission is performed. Note that k is an integer greater than or equal to 1 and less than or equal to N. Then, in the transmission of frame #k group, there is a symbol related to an SSID (information on the SSID of base station #k) and a symbol related to an encryption key (information on an encryption key for base station #k).

FIG. 12 illustrates one example of a configuration of a frame of a modulated signal transmitted by radio device 453 included in terminal 1050 in FIG. 22. In FIG. 12, time is represented on the horizontal axis. As illustrated in FIG. 12, radio device 453 included in terminal 1050 in FIG. 22 transmits, for example, preamble 1201, and then transmits control information symbol 1202 and information symbol 1203.

Here, preamble 1201 is a symbol used for base stations (or APs) 470-1, 470-2, and 470-3 that receive the modulated signal transmitted by radio device 453 in terminal 1050 in FIG. 22 to perform, for example, signal detection, temporal synchronization, frame synchronization, frequency synchronization, and frequency offset estimation.

Control information symbol 1202 includes data such as information related to the error correction encoding scheme method and/or demodulation scheme used in the generation of the modulated signal, information related to frame configuration, and information related to the transmission method used, and base stations (or APs) 470-1, 470-2, and 470-3, for example, demodulate the modulated signal based on the information included in control information symbol 1202.

Information symbol 1203 is a symbol for radio device 453 included in terminal 1050 in FIG. 22 to transmit data.

Note that radio device 453 included in terminal 1050 in FIG. 22 may transmit a frame including symbols other than the symbols illustrated in FIG. 12 (for example, a frame including a pilot symbol (reference symbol) midway through the information symbol). Moreover, the frame configuration, including the order in which the symbols are transmitted, is not limited to the configuration illustrated in FIG. 12. In FIG. 12, a plurality of symbols may be present along the frequency axis, that is to say, symbols may be present on a plurality of frequencies (a plurality of carriers).

FIG. 7 illustrates one example of a configuration of a frame of a modulated signal transmitted by base stations 470-1, 470-2, and 470-3 in FIG. 22. In FIG. 7, time is represented on the horizontal axis. As illustrated in FIG. 7, base stations 470-1, 470-2, and 470-3 transmit, for example, preamble 701, and then transmit control information symbol 702 and information symbol 703.

Here, preamble 701 is a symbol for radio device 453 included in terminal 1050 in FIG. 22, which receives the modulated signals transmitted by base stations 470-1, 470-2, and 470-3, to perform, for example, signal detection, temporal synchronization, frame synchronization, frequency synchronization, and/or frequency offset estimation.

Control information symbol 702 includes data such as information related to the error correction encoding scheme method and/or demodulation scheme used in the generation of the modulated signal, information related to frame configuration, and information related to the transmission method used, and radio device 453 included in terminal 1050 in FIG. 22, for example, demodulates the modulated signal based on the information included in the control information symbol.

Information symbol 703 is a symbol for base stations (or APs) 470-1, 470-2, and 470-3 in FIG. 22 to transmit data.

Note that base stations (or APs) 470-1, 470-2, and 470-3 in FIG. 22 may transmit a frame including symbols other than the symbols illustrated in FIG. 7 (for example, a frame including a pilot symbol (reference symbol) midway through the information symbol). Moreover, the frame configuration, including the order in which the symbols are transmitted, is not limited to the configuration illustrated in FIG. 7. In FIG. 7, a plurality of symbols may be present along the frequency axis, that is to say, symbols may be present on a plurality of frequencies (a plurality of carriers).

Figure 28:
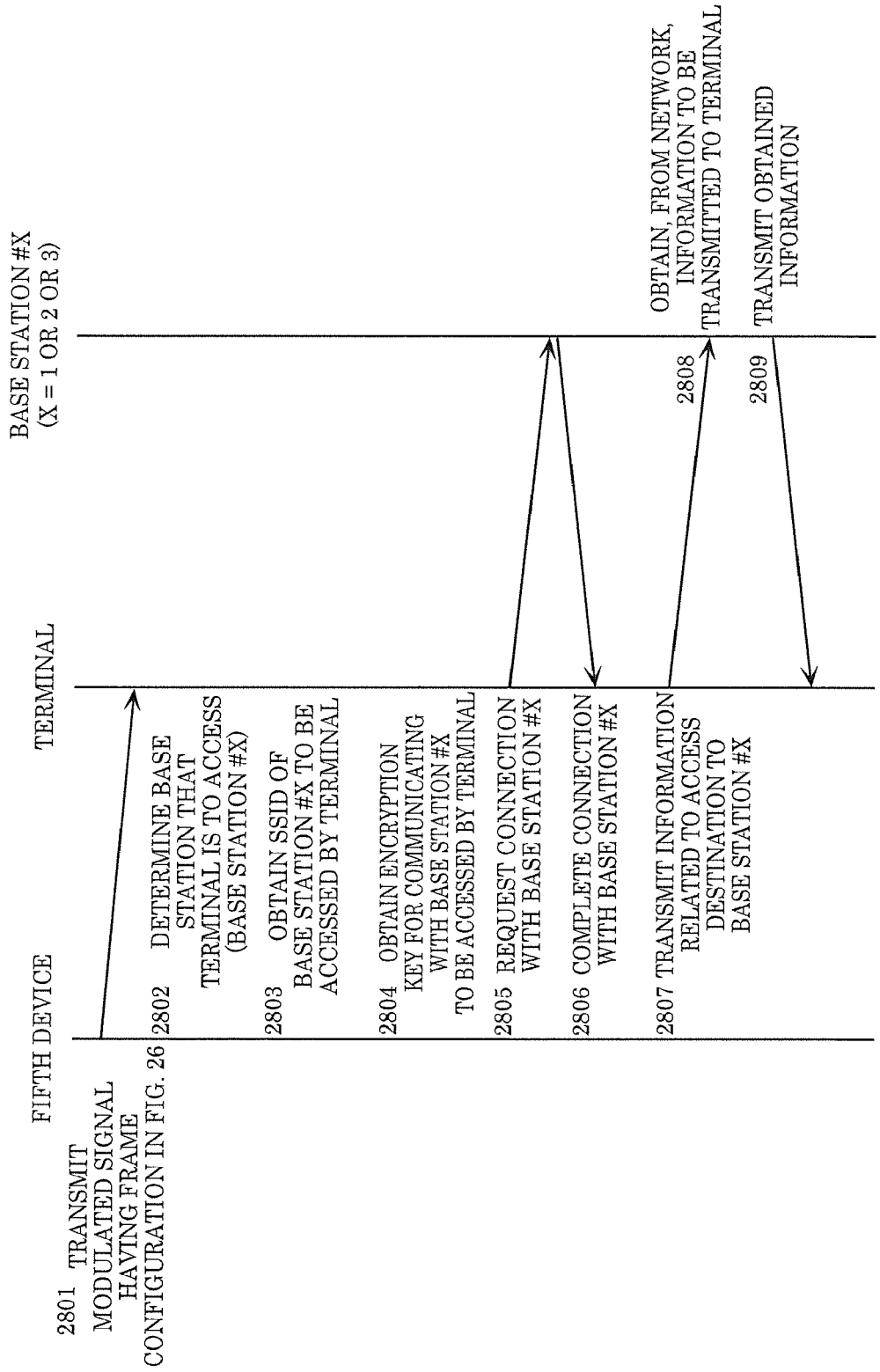
FIG. 28 is a flow chart of one example of processes performed by a device, terminal, and base station according to Embodiment 7.

FIG. 28 is a flow chart illustrating one example of processes implemented by fifth device 1000, terminal 1050, and base station #X (or AP #X) in FIG. 22. Note that X is 1, 2, or 3.

First, as 2801 in FIG. 28 illustrates, fifth device 1000 in FIG. 22 transmits a modulated signal having the frame configuration illustrated in FIG. 26.

Likewise, as 2802 in FIG. 28 illustrates, the modulated signal transmitted by fifth device 1000 in FIG. 22 is received, and terminal 1050 in FIG. 22 selects the base station to be accessed by terminal 1050 from among base station #1 470-1, base station #2 470-2, and base station #3 470-3 in FIG. 22.

This point will be discussed next. Terminal 1050 in FIG. 22 attempts to access a base station, and receives a modulated signal transmitted by fifth device 1000 in FIG. 22. Here, for example, in one frame of a moving or still picture, any one of frame #1 group transmission, frame #2 group transmission, and frame #3 group transmission in FIG. 26 is obtained. Then, from the obtained information on the base station (for example, the SSID), terminal 1050 in FIG. 22 determines which of base station #1 470-1, base station #2 470-2, and base station #3 470-3 in FIG. 22 to access.

For example, terminal 1050 selects the frame group transmission first received from among frame #1 group transmission, frame #2 group transmission, and frame #3 group transmission, and determines the base station to access from the information on the base station from that frame group transmission (for example, the SSID).

As 2803 in FIG. 28 illustrates, the modulated signal transmitted by fifth device 1000 in FIG. 22 is received, and terminal 1050 in FIG. 22 obtains the SSID of base station #X to be accessed by terminal 1050.

Likewise, as 2804 in FIG. 28 illustrates, terminal 1050 in FIG. 22 obtains an encryption key to be used for communicating with base station #X to be accessed by the terminal.

Terminal 1050 in FIG. 22 then requests connection with base station #X over radio waves (2805).

As 2806 in FIG. 28 illustrates, terminal 1050 in FIG. 22 completes the connection with base station #X upon receiving a response from base station #X.

As 2807 in FIG. 28 illustrates, terminal 1050 in FIG. 22 transmits information on the connection destination to base station #X using radio waves.

Then, as 2808 in FIG. 28 illustrates, base station #X obtains information to be transmitted to terminal 1050 in FIG. 22 from the network.

As 2809 in FIG. 28 illustrates, base station #X transmits the obtained information to terminal 1050 in FIG. 22 using radio waves, and terminal 1050 in FIG. 22 obtains the information.

For example, when necessary, terminal 1050 in FIG. 22 obtains required information from the network via base station #X.

As described above, based on the SSID information and the encryption key information transmitted from the fifth device, the terminal connects to the base station (or AP) and obtains information, whereby an advantageous effect that it is possible to securely obtain information via the base station (or AP) whose security has been authenticated can be achieved. This is because, when information from a visible light modulated signal is obtained, since it is visible light, the user can easily determine whether the source of information is secure or not.

For example, when an SSID is obtained from a modulated signal transmitted by a wireless LAN over radio waves, it is difficult for the user to determine which device transmitted the radio waves. Accordingly, from the viewpoint of ensuring information security, obtaining the SSID via visible light communication is more suitable.

Note that in this embodiment, the fifth device is exemplified as transmitting encryption key information, but, for example, when the base station (or AP) does not perform encrypted communication using an encryption key, the fifth device can transmit only the information related to an SSID without transmitting the encryption key information, that is, the fifth device may be implemented without the configuration related to an encryption key.

Moreover, the configuration of the fifth device is not limited to the configuration illustrated in FIG. 22, the configuration of the terminal is not limited to the configuration illustrated in FIG. 22, and the configurations of the connection destination of base stations #1, #2, and #3 are not limited to the configurations illustrated in FIG. 22.

Accordingly, when a configuration such as the one described in this embodiment is implemented, when there are a plurality of terminals in a given area, an advantageous effect of a reduction in terminals having difficulty accessing a base station can be achieved.

Note that in FIG. 27, the frame configurations of the modulated signals transmitted by the fifth devices disposed at circles 2701-1, 2701-2, 2701-3, 2701-4, 2701-5, 2701-6, 2701-7, 2701-8, 2701-8, 2701-9, and 2701-10 may all be the same as illustrated in FIG. 26, the frame configurations of the modulated signals transmitted by the fifth devices may be mutually different, and two or more of the fifth devices may transmit modulated signals having the same frame configuration.

Moreover, in this embodiment, the terminal connects to the base station or access point in a wireless LAN using radio waves, but the device that the terminal connects to may be any device that the terminal can connect to using radio waves, and is not limited to a base station or access point in a wireless LAN. For example, the device may be a base station such as a mobile phone, or a relay station. Moreover, in this embodiment, an example is given in which information on an SSID is included in the modulated signal, but the SSID is merely one non-limiting example. In other words, the information included in the modulated signal may be any information from which a secure base station to which the terminal may connect to can be identified; the information is not limited to including an SSID. Moreover, the terminal may be any device that has the functions that terminal 1050 in FIG. 22 has, and may, for example, may be a vehicle itself or be a device including transmitting and receiving functions that is included in a vehicle.

Embodiment 7 Summary

As described above, the transmission device according to this embodiment is, for example, device 1000 described above, and includes light source 104 and transmitter 102 that that generates a modulated signal based on an input signal and transmits the modulated signal from light source 104 as visible light by changing the luminance of light source 104 in accordance with the modulated signal. The modulated signal includes a plurality of items of information related to service set identifiers (SSIDs) of a plurality of mutually different access points in a wireless local area network (LAN).

Here, the modulated signal may include a plurality of frame groups respectively corresponding to the plurality of mutually different access points and each including one or more frames, and each of the one or more frames included in the plurality of frame groups may include the information related to the SSID of the access point corresponding to the frame group including the frame.

Moreover, the time required to transmit one of the plurality of frame groups may be longer than the time required to image one frame of a moving or still image by the reception device that receives the modulated signal.

Alternatively, the modulated signal may include a plurality of frames respectively corresponding to the plurality of mutually different access points, and each of the plurality of frames may include one or more items of the information related to the SSID of the access point corresponding to the frame. The time required to transmit one of the plurality of frames may be longer than the time required to image one frame of a moving or still image by the reception device that receives the modulated signal.

Moreover, transmitter 102 may transmit the plurality of frame groups respectively corresponding to the plurality of mutually different access points in random order along a time or frequency axis.

Alternatively, transmitter 102 may transmit the plurality of frame groups respectively corresponding to the plurality of mutually different access points in a regular order along a time or frequency axis.

The reception device according to the present embodiment is terminal 1050 that, for example, receives modulated signal transmitted as visible light from the transmission device. More specifically, the reception device includes: light receiver 151 that receives a modulated signal transmitted as visible light from a transmission device; data analyzer 155 that outputs analysis information by analyzing data based on the modulated signal; and a radio unit configured to, based on the analysis information, connect to an access point in a wireless local area network (LAN) using radio waves. For example, the radio unit is radio device 453. Here, the modulated signal includes a plurality of items of information related to service set identifiers (SSIDs) of a plurality of mutually different access points in the wireless LAN. Data analyzer 155 selects any one of the plurality of items of the information related to the SSIDs of the plurality of mutually different access points included in the modulated signal, and outputs, as the analysis information, the information related to the SSID selected. The radio unit connects to, using radio waves, the access point corresponding to the information related to the SSID output from data analyzer 155, from among the plurality of mutually different access points.

Here, the modulated signal may include a plurality of frame groups respectively corresponding to the plurality of mutually different access points and each including one or more frames, and each of the one or more frames included in the plurality of frame groups may include the information related to the SSID of the access point corresponding to the frame group including the frame.

The time required to receive one of the plurality of frame groups by light receiver 151 may be longer than the time required to image one frame of a moving or still image by light receiver 151.

Alternatively, the modulated signal may include a plurality of frames respectively corresponding to the plurality of mutually different access points, and each of the plurality of frames may include one or more items of the information related to the SSID of the access point corresponding to the frame. The time required to receive one of the plurality of frames by light receiver 151 may be longer than the time required to image one frame of a moving or still image by light receiver 151.

Moreover, light receiver 151 may receive the plurality of frame groups respectively corresponding to the plurality of mutually different access points in random order along a time or frequency axis.

Alternatively, light receiver 151 may receive the plurality of frame groups respectively corresponding to the plurality of mutually different access points in a regular order along a time or frequency axis.

The communication system according to the present embodiment includes a transmission device and a plurality of mutually different access points in a wireless local area network (LAN). The transmission device is, for example, device 1000, and the plurality of access points include, for example, base station #1 470-1, base station #2 470-2, and base station #3 470-3. The transmission device includes: light source 104; and transmitter 102 that generates a modulated signal based on an input signal and transmits the modulated signal from light source 104 as visible light by changing the luminance of light source 104 in accordance with the modulated signal. The modulated signal includes a plurality of items of information related to service set identifiers (SSIDs) of the plurality of mutually different access points, and at least one of the plurality of mutually different access points connects, using radio waves, to a reception device that received the modulated signal, and transmits information to the reception device.

Moreover, the transmission method according to the present embodiment includes: generating a modulated signal based on an input signal; and transmitting the modulated signal from a light source as visible light by changing a luminance of the light source in accordance with the modulated signal. The modulated signal includes a plurality of items of information related to service set identifiers (SSIDs) of a plurality of access points on mutually different wireless local area networks (LANs).

The reception method according to the present embodiment includes: receiving a modulated signal transmitted as visible light from a transmission device; outputting analysis information by analyzing data based on the modulated signal; and based on the analysis information, connecting to an access point in a wireless local area network (LAN) using radio waves. Here, the modulated signal includes a plurality of items of information related to service set identifiers (SSIDs) of a plurality of mutually different access points in the wireless LAN. The outputting of analysis information includes: selecting any one of the plurality of items of the information related to the SSIDs of the plurality of mutually different access points included in the modulated signal; and outputting, as the analysis information, the item of information related to the SSID selected. The connecting to the access point in the wireless LAN includes connecting to, using radio waves, the access point corresponding to the item of information related to the SSID output via the analyzing, from among the plurality of mutually different access points.

Moreover, the communication method according to the present embodiment includes: generating a modulated signal based on an input signal; and transmitting the modulated signal from a light source as visible light by changing a luminance of the light source in accordance with the modulated signal. The modulated signal includes a plurality of items of information related to service set identifiers (SSIDs) of a plurality of mutually different access points in a local area network (LAN). At least one of the plurality of mutually different access points connects, using radio waves, to a reception device that received the modulated signal, and transmits information to the reception device.

Supplemental Information 1 for Above Embodiments

Note that at least one of the field programmable gate array (FPGA) and central processing unit (CPU) may be configured to be able to download all or part of software required for implementing the communication method described in the present disclosure via wireless or wired communication, and moreover may be configured to be able to download all or part of software for receiving updates via wireless or wired communication. The downloaded software may be stored in storage, and the digital signal processing described in the present disclosure may be implemented by operating at least one of the FPGA and CPU based on the stored software.

Here, a device including at least one of the FPGA and CPU may be connected to a telecommunications modem via a wireless or wired connection, and the communication method described in the present disclosure may be implemented by the device and the telecommunications modem.

For example, a communication device, such as the base station, AP, terminal described in the present specification may include at least one of an FPGA and a CPU, and may include an interface for obtaining software for operating the at least one of an FPGA and a CPU from an external source. Furthermore, the communication device may include storage for storing software obtained from an external source, and may implement the signal processing described in the present disclosure by operating the FPGA and/or CPU based on the stored software.

The transmission device described in the present specification may be included in a first automobile or vehicle, and the reception device described in the present specification may be included in a second automobile or vehicle, and the transmission and receiving of data may be implemented under such a configuration.

The transmission device or part of the functions of the transmission device described in the present specification may be connected to the first automobile or vehicle via an interface, and the reception device or part of the functions of the reception device described in the present specification may be connected to the second automobile or vehicle via an interface, and the transmission of data may be implemented via transmission and reception thereby.

The transmission device described in the present specification may be included in a first automobile or vehicle, and the transmission and receiving of data between this transmission device and the reception device described in the present specification may be implemented under such a configuration.

The reception device described in the present specification may be included in a second automobile or vehicle, and the transmission and receiving of data between this reception device and the transmission device described in the present specification may be implemented under such a configuration.

Furthermore, the transmission device or part of the functions of the transmission device described in the present specification may be connected to the first automobile or vehicle via an interface, and the transmission and receiving of data between this string of transmission devices and the reception device described in the present specification may be implemented under such a configuration.

The reception device or part of the functions of the reception device described in the present specification may be connected to the second automobile or vehicle via an interface, and the transmission and receiving of data between this string of reception devices and the transmission device described in the present specification may be implemented under such a configuration.

When the automobile or vehicle includes the transmission device or part of the transmission device described in the present specification, or when the automobile or vehicle and the transmission device described in the present specification or part of the functions of the transmission device described in the present specification are connected via an interface, the light source included in the transmission device described in the present specification may be a light source included in the automobile or vehicle.

Figure 29:
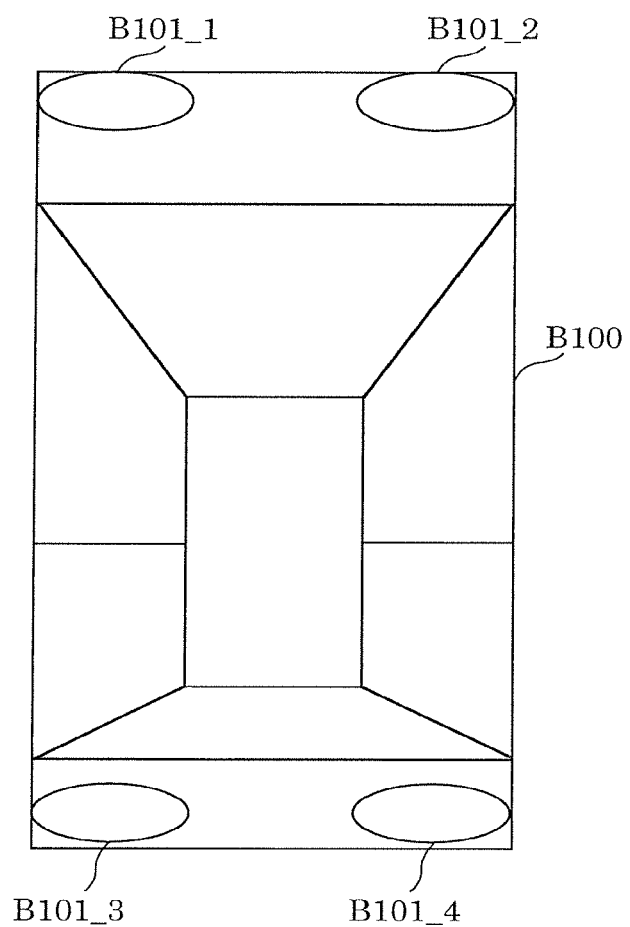
FIG. 29 illustrates one example of an automobile including a light source.

For example, automobile B100 illustrated in FIG. 29 includes light sources B101_1, B101_2, B101_3, and B101_4, and one or more of these light sources may be the light source to be used by the transmission device according to the present specification for transmitting the optical modulated signal.

Moreover, the function for selecting which light source among the plurality of light sources included in automobile B100 the transmission device according to the present specification uses for transmitting the optical modulated signal may be included in the transmission device or a device connected to the transmission device. Moreover, the brightness of the light source, the angle of emission of the light source, the positioning of the light source may be configurable.

When the automobile or vehicle includes the reception device or part of the reception device described in the present specification, or when the automobile or vehicle and the reception device described in the present specification or part of the functions of the reception device described in the present specification are connected via an interface, the light receiver included in the reception device described in the present specification may be a light receiver included in the automobile or vehicle (for example, an image sensor or photodiode).

Figure 30:
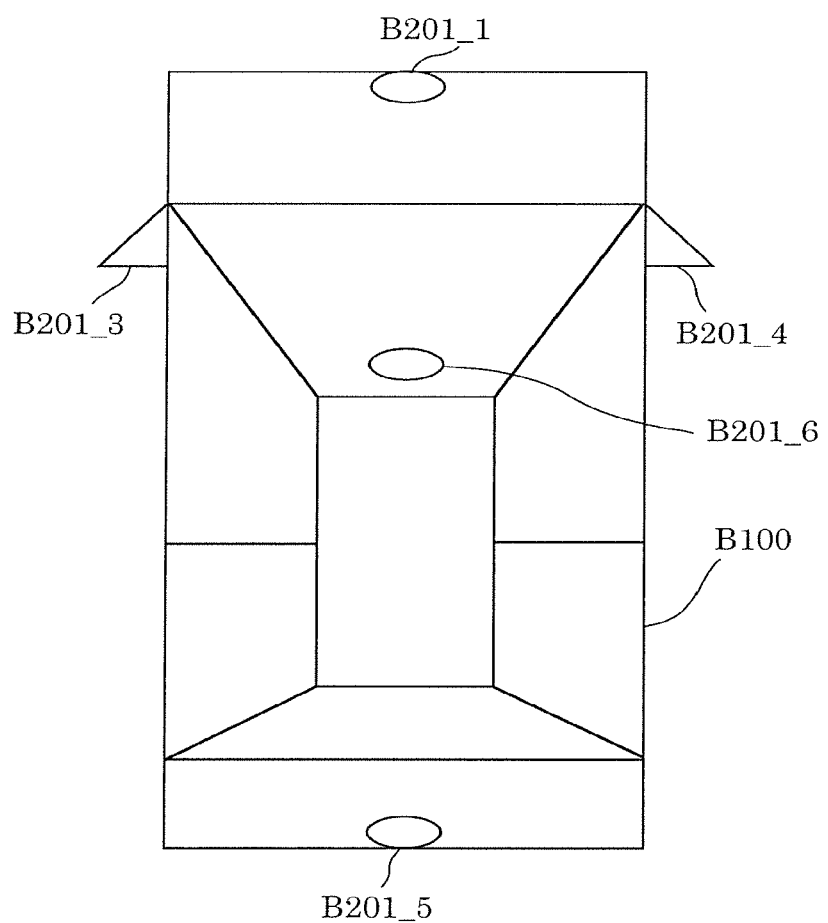
FIG. 30 illustrates one example of an automobile including a light receiver.

For example, automobile B100 illustrated in FIG. 30 includes light receivers B201_1, B201_3, B201_4, and B201_5, and one or more of these light receivers may be the light receiver to be used by the reception device according to the present specification for receiving the optical modulated signal.

Moreover, the function for selecting which light receiver among the plurality of light receivers included in automobile B100 the reception device according to the present specification uses for receiving the optical modulated signal may be included in the reception device or a device connected to the reception device. Moreover, the angle of the light receiver and the positioning of the light receiver may be configurable.

Furthermore, the reception device described in the present specification may display, on the front panel included in the automobile or in the cockpit of the vehicle, a notification indicating that data has been received. Moreover, the reception device described in the present specification may notify a user that data has been received by vibrating the steering wheel of, for example, the automobile, or vibrating a vibrator included on the steering wheel.

Moreover, an automobile including the reception device according to the present specification and the terminal may be connected via an interface, and data obtained from the reception device may be stored in storage included in the terminal. Moreover, the automobile may also include a storage, and the automobile may store received data therein. Moreover, the storage included in the terminal and the storage included in the automobile may both store received information.

In the present specification, a server may provide an application related to processes pertaining to the reception device, and the functions of the reception device according to the present specification may be implemented by the terminal installing the application. Note that the application may be provided to the terminal by the communication device including in the transmission device according to the present specification connecting to a server over a network, and may be provided to the terminal by a communication device including a different transmission function connecting to a server over a network.

Similarly, in the present specification, a server may provide an application related to processes pertaining to the transmission device, and the functions of the transmission device according to the present specification may be implemented by the terminal installing the application. Note that a method in which the application is provided to a different communication device by the communication device connecting to a server over a network is conceivable.

Moreover, a server may provide software related to the light source included in the transmission device and the light receiver included in the reception device, and transmission and reception of the optical modulated signal by the light source included in the transmission device and the light receiver included in the reception device, respectively, may be supported by obtaining this software.

Furthermore, the transmission device according to the present specification may function as a server, and an application included in the transmission device may be provided to the communication device using some communication means, and the reception device according to the present specification can be implemented by the application obtained by the communication device downloading the application.

Note that in the present specification, there is reference to a "lamp" and a "light source", but the method may be a method of a projector displaying, for example, a still picture, moving picture, or advertisement, and the optical modulated signal being included in that light. In other words, the "lamp" and a "light source" may include functions other than the emission of light. Moreover, the "lamp" and a "light source" may comprise a plurality of lamps and light sources.

Furthermore, the transmission method used by the communication device that generates an optical modulated signal and emits light may be a method other than the transmission method described in the present specification. Moreover, the optical modulated signal may include information other than what is described in the present specification.

Moreover, the lamp and/or light source, such as an LED lamp and/or light source, may itself include the functions of the transmission device described in the present specification.

Furthermore, the device that generates the optical transmission modulated signal may not include a lamp or light source, and may be connected to a lamp and/or light source via an interface.

Figure 31:
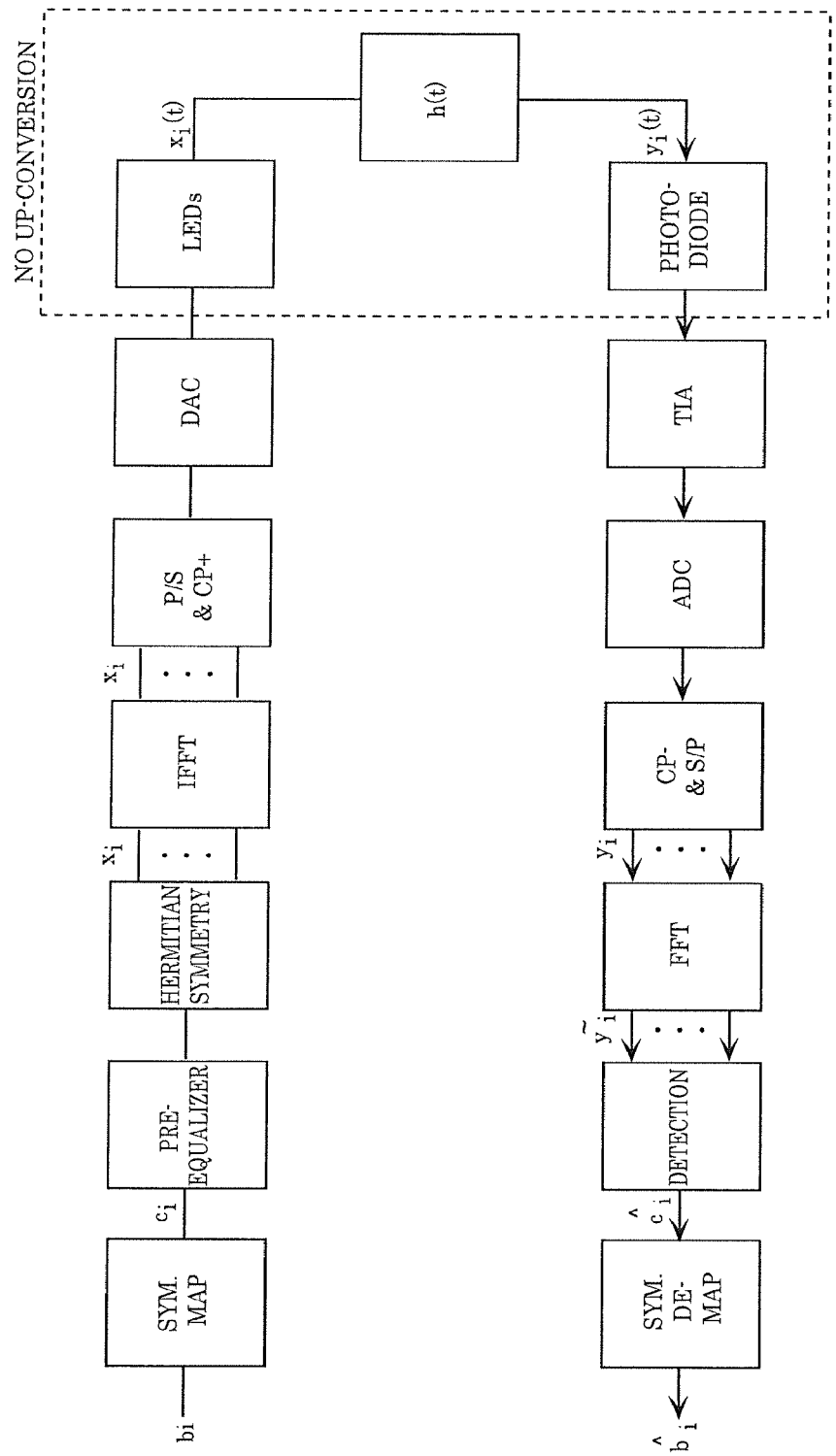
FIG. 31 illustrates another example of a communication method.

The communication method between the transmission device and the reception device described in the present specification and the present embodiment may be the communication method illustrated in FIG. 31. Hereinafter, FIG. 31 will be described.

The symbol mapper receives an input of transmission data, performs mapping based on a modulation scheme, and outputs a symbol sequence (ci).

The pre-equalizer receives an input of the symbol sequence, performs pre-equalizing processing on the symbol sequence to reduce the equalizing processes on the reception-side, and outputs a pre-equalized symbol sequence.

The Hermitian symmetry processor receives an input of the pre-equalized symbol sequence, allocates sub-carriers to the pre-equalized symbol sequence to secure Hermitian symmetry, and outputs parallel signals.

The inverse (fast) Fourier transformer receives inputs of the parallel signals, applies an inverse (fast) Fourier transform to the parallel signals, and outputs inverse (fast) Fourier transformed signals.

The parallel serial and cyclic prefix adder receives an input of the inverse (fast) Fourier transformed signals, performs parallel conversion and adds cyclic prefix, and outputs the signal-processed signal.

The digital-to-analog converter receives an input of the signal-processed signal, performs digital-to-analog conversion, outputs an analog signal, and the analog signal is emitted as light from, for example, one or more LEDs.

Note that the pre-equalizer and the Hermitian symmetry processor need not be included. In other words, there may be instances in which the pre-equalizer and the Hermitian symmetry processor do not perform their respective processes.

The photodiode receives an input of light, and obtains a reception signal via a transimpedance amplifier (TIA).

The analog-to-digital converter performs an analog-to-digital conversion on the reception signal, and outputs a digital signal.

The cyclic prefix subtractor and serial parallel converter receives an input of the digital signal, subtracts the cyclic prefix, and then performs serial parallel conversion, and receives an input of parallel signals.

The (fast) Fourier transformer receives inputs of the parallel signals, applies a (fast) Fourier transform to the parallel signals, and outputs (fast) Fourier transformed signals.

The detector receives inputs of the (fast) Fourier transformed signals, performs detection, and outputs a series of reception symbols.

The symbol demapper receives an input of the series of reception symbols, performs demapping, and obtains a series of reception data.

In this way, even when such a transmission device that transmits the optical modulated signals and such a reception device that receives the optical modulated signals are applied to the amendments according to the present specification, the embodiments can be implemented in the same manner.

Moreover, the communication method between the transmission device and the reception device described in the present embodiment may be the following communication method.

Line Scan Sampling

An image sensor such as a complementary metal oxide semiconductor (CMOS) sensor is included in a smartphone or digital camera or the like. For example, the entire scene in a single image captured by the CMOS sensor is not captured at a single instant, but rather, for example, captured line by line using a rolling shutter method, whereby the sensor reads out the amount of light received line by line. Accordingly, the amount of time required for the reading out is calculated, and exposure start and end times are controlled for each line by implementing a time delay. In other words, images captured by the CMOS sensor are constructed from a plurality of lines captured with a slight time lag between each line.

This exploits the rolling shutter effect of the CMOS sensor to allow for an improvement in visible light signal reception speeds.

Figure 32:
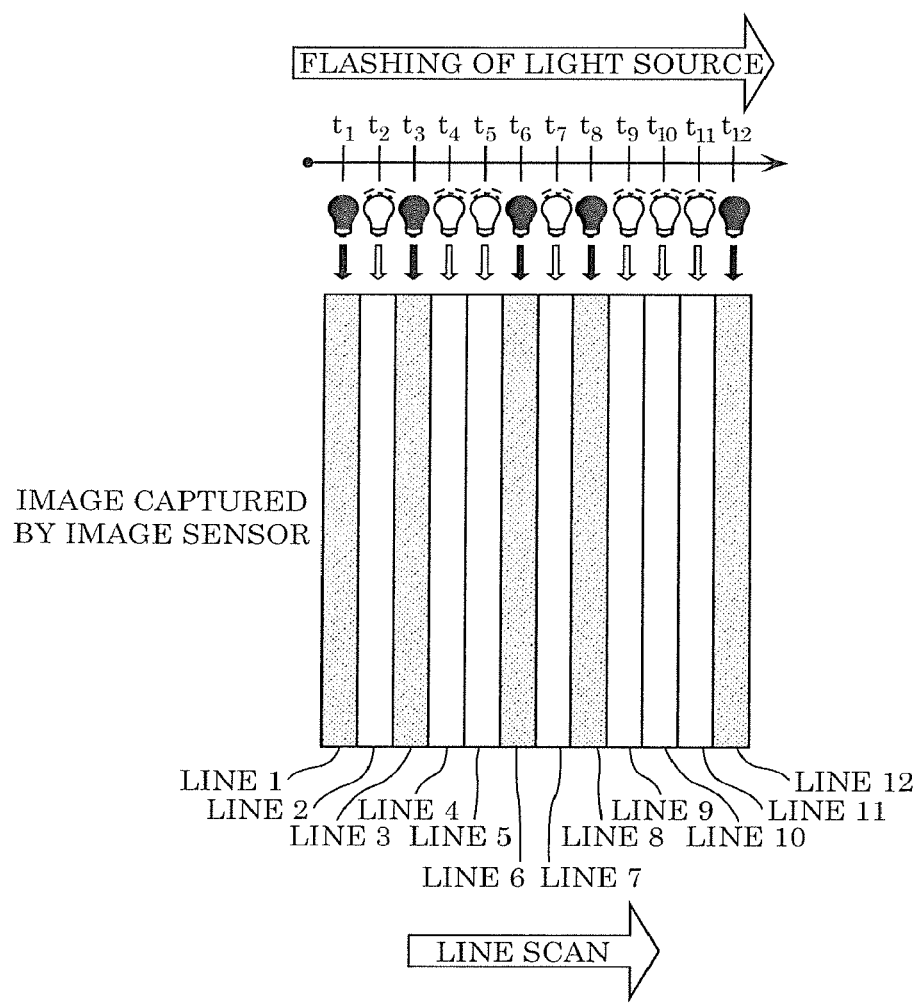
FIG. 32 illustrates one example of line scan sampling.

In other words, in a first example of a visible light communication scheme, as illustrated in FIG. 32, utilizing the slight time lag between the exposure period of each line, the luminance and color of the light source across a plurality of points in time can be calculated line by line from a single image (image captured by the image sensor), making it possible to capture a signal modified faster than the frame rate of the image sensor.

This sampling method is referred to as "line scan sampling", and a single row of pixels exposed at the same time is referred to as an "exposure line".

Note that line scan sampling can be implemented using the rolling shutter effect of a CMOS sensor, but even when the rolling shutter effect is implemented using a sensor other than a CMOS sensor, such as a charge-coupled device (CCD) sensor or an organic CMOS sensor, the line scan sampling can be implemented in the same manner.

Figure 33:
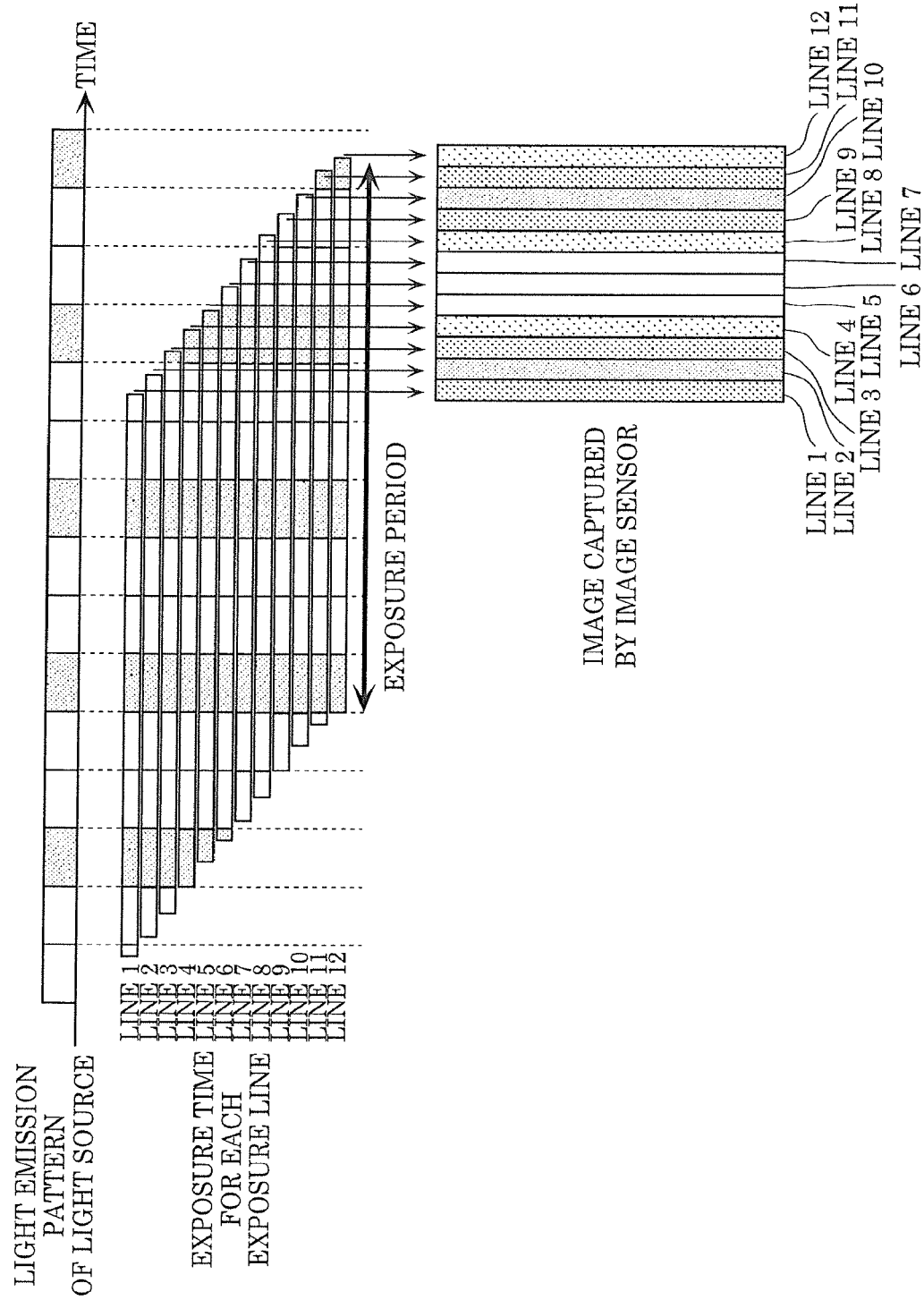
FIG. 33 illustrates an example of a captured image in which a striped pattern does not appear.

However, in the settings used when capturing an image in the camera functions (capturing functions for moving or still images), even if a rapidly flashing light source is captured, the flashing will not appear as a striped pattern extending along the exposure lines. This is because, with this setting, the exposure period is sufficiently longer than the flash cycle of the light source, so, as illustrated in FIG. 33, the changes in luminance resulting from the flashing (light emission pattern) of the light source are uniform, resulting in a substantially small variation in pixel values between exposure lines, producing an approximately uniform image.

Figure 34:
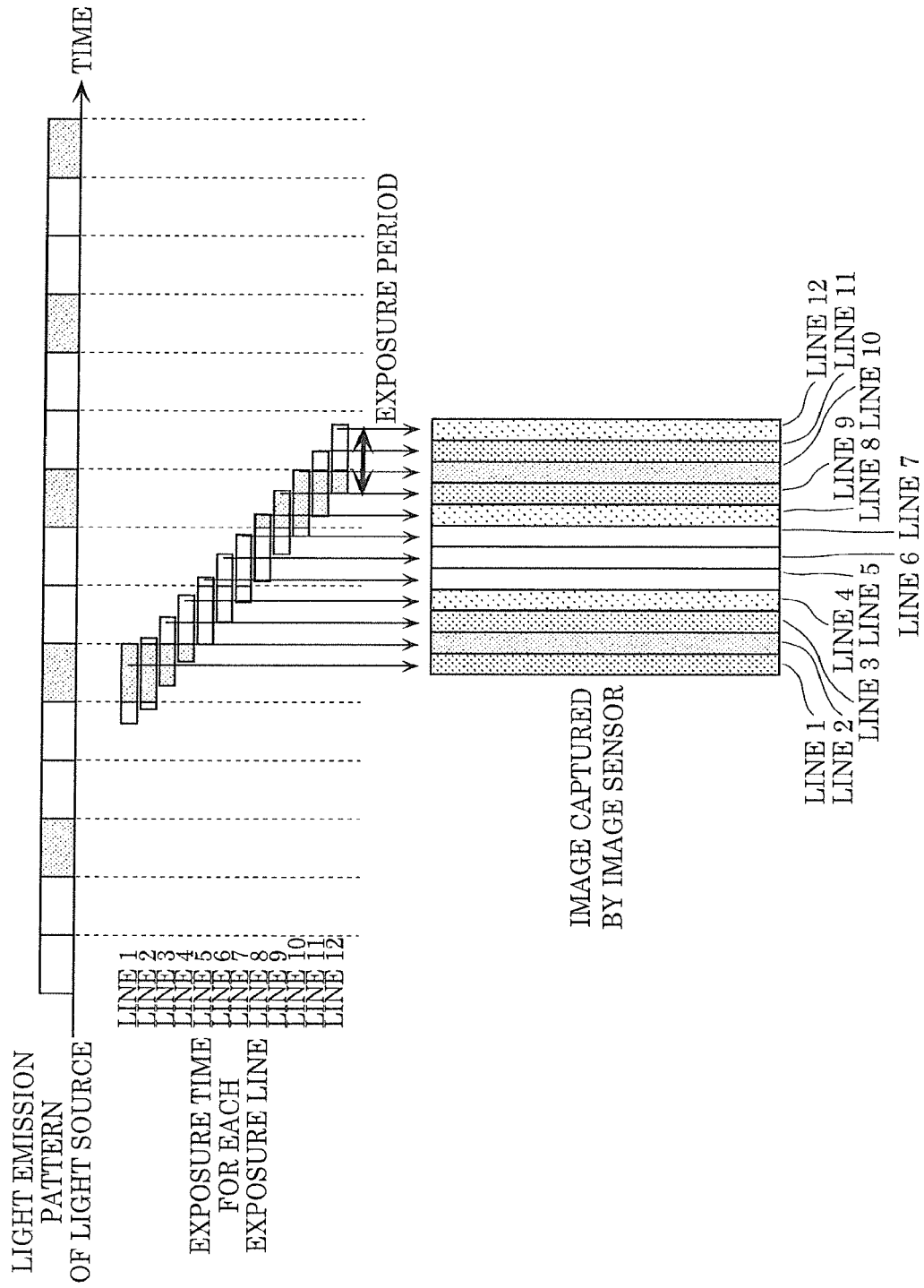
FIG. 34 illustrates an example of a captured image in which a striped pattern appears.

In contrast, as illustrated in FIG. 34, by setting the exposure period equal to or slower than the flash cycle of the light source, the state (light emission pattern) of the flashing of the light source can be observed as variations in luminance between exposure lines.

For example, the exposure lines are designed to extend parallel lengthwise relative to the image sensor. In such cases, as one example, assuming the frame rate is 30 frames per second (fps), when the resolution is 1920×1080, at least 32400 samples are obtained per second, and when the resolution is 3840×2160, at least 64800 samples are obtained per second.

Line Scan Sampling Application Example

Note that the above described line scan sampling in which a signal indicating an amount of light received per line is read out, but methods of sampling an optical signal using an image sensor such as a CMOS sensor are not limited to this example. A variety of methods that can obtain a sampled signal at a sampling rate that is higher than the frame rate used to capture a normal moving picture, can be used as the sampling method to be used to receive the optical signals. For example, a method of controlling the exposure time per pixel and reading out a signal or a method of controlling the exposure time per group of pixels arranged in a shape other than a line and reading out a signal may be used by utilizing a global shutter method that has a shutter function for each pixel. Moreover, a method of reading out signals a plurality of times from the same pixel in a period equivalent to one frame in the frame rate used in the capture of a normal moving picture may be used.

Frame Sampling

Furthermore, with a frame rate method that gives a shutter method for each non-pixel, it is possible to sample optical signals even in a method by which the frame rate is sped up.

For example, the present specification can be implemented in any of the line scan sampling, line scan sampling application example, and frame sampling methods described above.

Light Source and Modulation Scheme

With visible light communication, for example, a light emitting diode (LED) can be used as a transmitter. LEDs are commonly used in lamps and in backlit light sources in displays, and can flash at high speeds.

However, light sources that are used as visible light communication transmitters cannot be allowed to flash uncontrolled when performing visible light communication. If the changes in luminance made for visible light communication are recognizable to the human eye, the original functionality of a light source as a lamp will be lost. Accordingly, the transmission signal needs to be emitted at a desired brightness and needs to be imperceptible to the human eye.

Figure 35A:
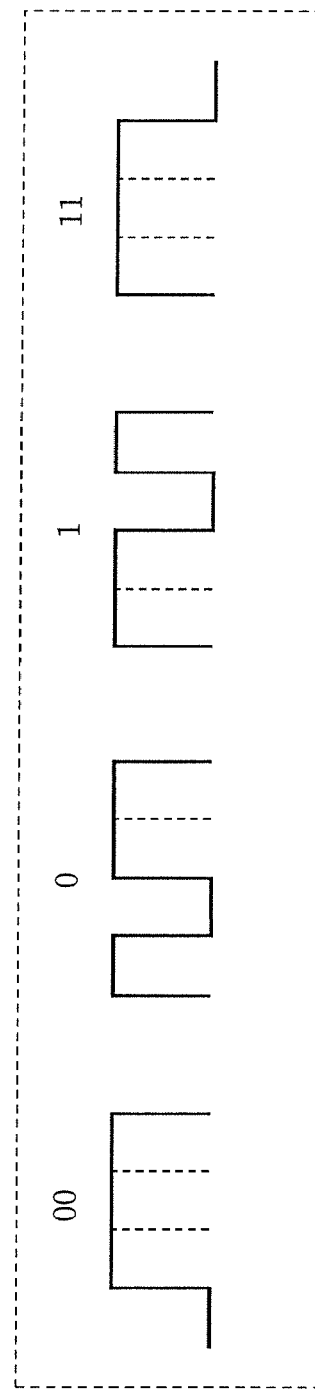
FIG. 35A illustrates one example of a 4 PPM modulation scheme.

One modulation scheme that meets these requirements is 4-pulse position modulation (4 PPM). As illustrated in FIG. 35A, 4 PPM is a scheme in which two bits are represented by a group of four time slots each indicating either bright or dark light emitted by a light source. Moreover, as illustrated in FIG. 35A, in 4 PPM, each group of the four time slots includes three light slots and one dark slot. Accordingly, regardless of the content of the signal, the average brightness (average luminance) is ¾=75%.

Figure 35B:
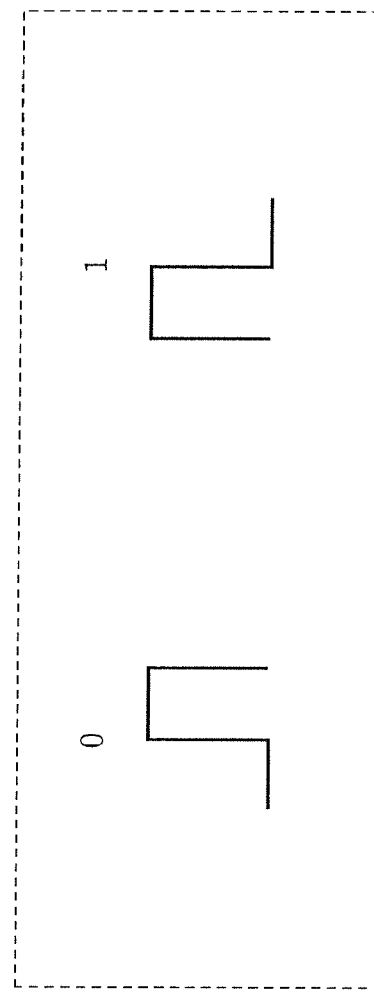
FIG. 35B illustrates one example of a Manchester coding scheme.

For comparison, as a similar scheme, consider the Manchester coding scheme illustrated in FIG. 35B. In the Manchester coding scheme, one bit is expressed with two states, and the modulation efficiency is 50%, which is the same as 4 PPM, but among the two states, one is bright and one is dark, so the average luminance is ½=50%. In other words, 4 PPM is more suitable than the Manchester coding scheme as a visible light communication scheme. However, since communication capability is not adversely affected by changes in luminance from visible light communication that are recognizable to the human eye, depending on the application, there may be no problem in using a method in which the changes in luminance are recognizable to the human eye. Accordingly, the transmitter (light source) may use, for example, an amplitude shift keying (ASK) method, a phase shift keying (PSK) method, or a pulse amplitude modulation (PAM) method to generate the modulated signal and pulse the light source to emit light.

Note that the communication method between the transmission device and the reception device described in the present specification is not limited to the above example. Even frequency-based wireless communication methods such as optical, visible light, infrared, ultraviolet methods can be implemented in the same manner. Moreover, in the above description, an example is given in which optical modulated signals are received via an image sensor, but a photodiode may be used in place of the image sensor to receive the optical modulated signals. Alternatively, a device other than an image sensor or photodiode may be used to receive the optical modulated signals.

In the present specification, a symbol related to location or position information, a symbol related to time information, a symbol related to an SSID, a symbol related to an access destination, and a symbol related to an encryption key are described using the terminology "symbol", but these may be referred to as "data" or "information" or "field" or "bit" or "region" instead of "symbol", and the embodiments can be implemented in the same manner. They may be referred to as something other than "data" or "information" or "field" or "bit" or "region" as well. Moreover, the transmission device may transmit any type of symbol configuration, such as a symbol related to location or position information, a symbol related to time information, a symbol related to an SSID, a symbol related to an access destination, and a symbol related to an encryption key. What is important is that data related to location or position information, data related to time information, data related to an SSID, data related to an access destination, data related to an encryption key is transmitted to the communication partner.

In the present specification, in the transmission device that includes, for example, a light source and/or lamp, the light source may be comprised of a plurality of light sources, and/or the lamp may be comprised of a plurality of lamps.

Supplemental Information 2 for Above Embodiments

It goes without saying that the embodiments described in the present specification may be combined with other aspects.

Moreover, the embodiments are merely examples. For example, while a modulation scheme, an error correction coding method (error correction code, code length, encode rate, etc., to be used), control information, etc., are exemplified, it is possible to carry out the present disclosure with the same configuration even when other types of a modulation scheme, an error correction coding method (error correction code, code length, encode rate, etc., to be used), control information, etc., are applied.

Regarding the modulation schemes, even when a modulation scheme other than the modulation schemes described herein is used, it is possible to carry out the embodiments and the other subject matter described herein. For example, amplitude phase shift keying (APSK) (such as 16APSK, 64APSK, 128APSK, 256APSK, 1024APSK and 4096APSK), pulse amplitude modulation (PAM) (such as 4PAM, 8PAM, 16PAM, 64PAM, 128PAM, 256PAM, 1024PAM and 4096PAM), phase shift keying (PSK) (such as BPSK, QPSK, 8PSK, 16PSK, 64PSK, 128PSK, 256PSK, 1024PSK and 4096PSK), and quadrature amplitude modulation (QAM) (such as 4QAM, 8QAM, 16QAM, 64QAM, 128QAM, 256QAM, 1024QAM and 4096QAM) may be applied, or in each modulation scheme, uniform mapping or non-uniform mapping may be performed. Moreover, a method for arranging 2, 4, 8, 16, 64, 128, 256, 1024, etc., signal points on an I-Q plane (a modulation scheme having 2, 4, 8, 16, 64, 128, 256, 1024, etc., signal points) is not limited to a signal point arrangement method of the modulation schemes described herein.

In the present specification, conceivable devices that include the radio device described in the present specification include a communications and broadcast apparatus, such as a broadcast station, a base station, an access point, a terminal or a mobile phone, or a communication apparatus such as a television, a radio, a terminal, a personal computer, a mobile phone, an access point, or a base station. Moreover, the radio device described in the present specification is conceivably a device having communication functions that is connectable via some interface to a device for executing an application in, for example, a television, a radio, a personal computer or a mobile phone.

In the present specification, conceivable devices that include the receiver described in the present specification include a communications and broadcast apparatus, such as a broadcast station, a base station, an access point, a terminal or a mobile phone, or a communication apparatus such as a television, a radio, a terminal, a personal computer, a mobile phone, an access point, or a base station.

Moreover, in the radio-wave communication radio device according to this embodiment, symbols other than data symbols, such as pilot symbols (preamble, unique word, post-amble, reference symbol, etc.) or symbols for control information, may be arranged in any way in a frame. Here, the terms "pilot symbol" and "control information symbol" are used, but the naming of such symbols is not important; the functions that they perform are.

A pilot symbol may be a known symbol that is modulated using PSK modulation in a transceiver (alternatively, a symbol transmitted by a transmitter can be known by a receiver by the receiver being periodic), and the receiver detects, for example, frequency synchronization, time synchronization, and a channel estimation (channel state information (CSI)) symbol (of each modulated signal) by using the symbol.

Moreover, the symbol for control information is a symbol for transmitting information required to be transmitted to a communication partner in order to establish communication pertaining to anything other than data (such as application data) (this information is, for example, the modulation scheme, error correction encoding scheme, or encode rate of the error correction encoding scheme used in the communication, or settings information in an upper layer).

Note that the present disclosure is not limited to each exemplary embodiment, and can be carried out with various modifications. For example, in each embodiment, the present disclosure is described as being performed as a communication device. However, the present disclosure is not limited to this case, and this communication method can also be used as software.

Note that a program for executing the above-described communication method may be stored in read only memory (ROM) in advance to cause a central processing unit (CPU) to operate this program.

Moreover, the program for executing the communication method may be stored in a computer-readable storage medium, the program stored in the recording medium may be recorded in random access memory (RAM) in a computer, and the computer may be caused to operate according to this program.

Each configuration of each of the above-described embodiments, etc., may be realized as a large scale integration (LSI) circuit, which is typically an integrated circuit. These integrated circuits may be formed as separate chips, or may be formed as one chip so as to include the entire configuration or part of the configuration of each embodiment. LSI is described here, but the integrated circuit may also be referred to as an integrated circuit (IC), a system LSI circuit, a super LSI circuit or an ultra LSI circuit depending on the degree of integration. Moreover, the circuit integration technique is not limited to LSI, and may be realized by a dedicated circuit or a general purpose processor. After manufacturing of the LSI circuit, a field programmable gate array (FPGA) or a reconfigurable processor which is reconfigurable in connection or settings of circuit cells inside the LSI circuit may be used. Further, when development of a semiconductor technology or another derived technology provides a circuit integration technology which replaces LSI, as a matter of course, functional blocks may be integrated by using this technology. Adaption of biotechnology, for example, is a possibility.

Note that in the present specification, for example, in Embodiments 4, 5, 6, and 7, an encryption key for a terminal to connect to a base station over radio waves is described, but the encryption key is not limited to an encryption key for connection over radio waves.

For example, assume the base station is connected to a network and the terminal communicates with the network via the base station. In such cases, the encryption key may be an encryption key for the terminal to connect to the network. Accordingly, information on an encryption key is included in the optical modulated signal described in the present specification, and even in this cases, the embodiments can be implemented in the same way, and the same advantageous effects can be achieved.

Moreover, the optical modulated signal may include at least one of an encryption key for connecting with a base station (for example, an encryption key for an SSID) and an encryption key for connecting to a network.

Although only some exemplary embodiments have been described above, the scope of the Claims of the present application is not limited to these embodiments. Those skilled in the art will readily appreciate that various modifications may be made in these exemplary embodiments and that other embodiments may be obtained by arbitrarily combining the structural elements of the embodiments without materially departing from the novel teachings and advantages of the subject matter recited in the appended Claims. Accordingly, all such modifications and other embodiments are included in the present disclosure.

INDUSTRIAL APPLICABILITY

The present disclosure is applicable to a wide range of communication systems that transmit and receive optical modulated signals.

The invention claimed is:

1. A receiving method comprising:

receiving a light signal transmitted from a light transmission device;

demodulating the light signal to obtain an access information associated with an access point for a map data and an identifier of the light transmission device; and obtaining the map data from the access point via a wireless signal that is not a light signal, based on the access information, wherein the map data includes a location of the light transmission device and the identifier of the light transmission device, and the map data indicates an arrangement of constituent elements, the location of the light transmission device being indicated as a constituent element at a specific position on the map data.

2. A receiving apparatus comprising:

a light signal receiver that receives a light signal transmitted from a light transmission device and demodulates the light signal to obtain an access information associated with an access point for a map data and an identifier of the light transmission device; and a processor that obtains the map data from the access point via a wireless signal that is not a light signal, based on the access information, wherein the map data includes a location of the light transmission device and the identifier of the light transmission device, and the map data indicates an arrangement of constituent elements, the location of the light transmission device being indicated as a constituent element at a specific position on the map data.

* * * * *